US010344288B2

(12) United States Patent
Miller et al.

(10) Patent No.: US 10,344,288 B2
(45) Date of Patent: Jul. 9, 2019

(54) GLUCOAMYLASE-MODIFIED YEAST STRAINS AND METHODS FOR BIOPRODUCT PRODUCTION

(71) Applicant: CARGILL, INCORPORATED, Wayzata, MN (US)

(72) Inventors: Christopher K. Miller, Andover, MN (US); Ana Negrete-Raymond, Chanhassen, MN (US); Jon Veldhouse, Plymouth, MN (US); Amit Vas, Minneapolis, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/562,266

(22) PCT Filed: Mar. 25, 2016

(86) PCT No.: PCT/US2016/024249
§ 371 (c)(1),
(2) Date: Sep. 27, 2017

(87) PCT Pub. No.: WO2016/160584
PCT Pub. Date: Oct. 6, 2016

(65) Prior Publication Data
US 2018/0094269 A1  Apr. 5, 2018

Related U.S. Application Data

(60) Provisional application No. 62/139,312, filed on Mar. 27, 2015.

(51) Int. Cl.
*C12N 9/34* (2006.01)
*C12N 15/81* (2006.01)
*C12P 7/10* (2006.01)

(52) U.S. Cl.
CPC ............... *C12N 15/81* (2013.01); *C12P 7/10* (2013.01); *C12Y 302/01003* (2013.01); *Y02E 50/16* (2013.01); *Y02E 50/17* (2013.01)

(58) Field of Classification Search
CPC ..................... C12N 9/2428; C12Y 302/01003
USPC .............................................. 435/205, 254.2
See application file for complete search history.

(56) References Cited

U.S. PATENT DOCUMENTS

| | | | |
|---|---|---|---|
| 4,546,082 A | 10/1985 | Kurjan et al. |
| 4,870,008 A | 9/1989 | Brake |
| 5,024,941 A | 6/1991 | Maine et al. |
| 5,422,267 A | 6/1995 | Yocum et al. |
| 5,521,086 A | 5/1996 | Scott et al. |
| 5,587,290 A | 12/1996 | Klionsky et al. |
| 6,214,577 B1 | 4/2001 | Yocum |
| 7,785,872 B2 | 8/2010 | Chang et al. |
| 8,394,622 B2 | 3/2013 | Haefele et al. |
| 8,664,475 B2 | 3/2014 | Puzio et al. |
| 8,733,149 B2 | 5/2014 | Yu et al. |
| 8,733,321 B2 | 5/2014 | Cohn et al. |
| 8,735,544 B1 | 5/2014 | Hammond et al. |
| 2007/0065905 A1 | 3/2007 | Branduardi et al. |
| 2007/0117186 A1 | 5/2007 | Sahara et al. |
| 2007/0166788 A1 | 7/2007 | Jin et al. |
| 2010/0317078 A1 | 12/2010 | Villa-Garcia et al. |
| 2011/0033907 A1 | 2/2011 | Forrester et al. |
| 2011/0229968 A1 | 9/2011 | Sohn et al. |
| 2012/0064591 A1 | 3/2012 | Gasch et al. |
| 2013/0137181 A1 | 5/2013 | Choi et al. |
| 2013/0149760 A1 | 6/2013 | Forrester et al. |
| 2013/0323822 A1 | 12/2013 | Brevnova et al. |

FOREIGN PATENT DOCUMENTS

| | | |
|---|---|---|
| EP | 123544 A2 | 10/1984 |
| EP | 228254 A2 | 7/1987 |
| EP | 2734490 A1 | 5/2014 |
| EP | 2735301 A1 | 5/2014 |
| WO | 03105889 A1 | 12/2003 |
| WO | 2004/042036 A2 | 5/2004 |
| WO | 2009037279 A1 | 3/2009 |
| WO | 2011153516 A2 | 12/2011 |
| WO | 2013011208 A1 | 1/2013 |
| WO | 2013092840 A1 | 6/2013 |
| WO | 2014029808 A1 | 2/2014 |
| WO | 2014078920 A1 | 5/2014 |
| WO | 2014081803 A1 | 5/2014 |
| WO | 2015023989 A1 | 2/2015 |
| WO | 2016127083 A1 | 8/2016 |
| WO | 2016160584 A1 | 10/2016 |

OTHER PUBLICATIONS

Das R C, et al., "Chapter 10: Host cell control of heterologous protein production in *Saccharomycescerevisiae*", Marcel Dekker, Inc., New York / Basel, XP008179956, 1990, 311-342.

Eva Hostinová, et al., "Molecular cloning and 3D structure prediction of the first raw-starch-degrading glucoamylase without a separate starch-binding domain", XP055266201, Archives of Biochemistry and Biophysics, Mar. 1, 2003 Academic Press, US—ISSN 0003-9861, vol. 411, Issue 2, Mar. 15, 2003, 189-195.

Eva Hostinová, et al., "Yeast glucoamylases: molecular-genetic and structural characterization", Biologia, Sap-Slovak Academic Press, Bratislava, SK, vol. 65 No. 4, Aug. 1, 2010, 559-568.

(Continued)

*Primary Examiner* — Tekchand Saidha

(57) ABSTRACT

Genetically engineered yeast with a heterologous glucoamylase and fermentation methods are described. The engineered yeast can have multiple exogenous nucleic acid sequences which each have a different sequence, but that encode the same or a similar glucoamylase protein that is heterologous to the yeast. The engineered yeast exhibit desirable bioproduct production profiles during a fermentation process. A fermentation medium with a starch material can be fermented with the engineered yeast to provide high ethanol titers, low glycerol titers, or both.

20 Claims, 3 Drawing Sheets

Specification includes a Sequence Listing.

(56) References Cited

OTHER PUBLICATIONS

I. Ballesteros et al., "Optimization of the simultaneous saccharification and fermentation process using thermotolerant yeasts", Applied Biochemistry and Biotechnology, Spring 1993, vol. 39-40, Issue 1,, 1993, 201-211.

Luo Jinxian, et al., "Expression and secretion of alpha-amylase and glucoamylase in *Saccharomyces cerevisiae*", Chinese Journal of Biotechnology, Allerton Press, vol. 10, No. 4, 1994, 241-248.

Nakamura, et al., "Alcohol fermentation of starch by a genetic recombinant yeast having glucoamylase activity", Biotechnology and Bioengineering, Wiley etc—ISSN 0006-3592, DOI: http://dx.doi.org/10.1002/(SICI)1097-0290(19970105)53:1<21::AIT-BIT4>3.0.CO;2-0, vol. 53, Jan. 1, 1997, 21-25.

Punt P J, et al., "Intracellular and extracellular production of proteins in Aspergillus under the control of expression signals of the highly expressed Aspergillus nidulans gpdA gene", Journal of Biotechnology, Elsevier Science Publishers, Amsterdam, NL—ISSN 0168-1656, vol. 17, Nr:1, Jan. 1, 1991, 19-33.

Shi-Hwei Liu, et al., "Improved secretory production of glucoamylase in Pichia pastoris by combination of genetic manipulations", Biochemical and Biophysical Research Communications, Elsevier, 2005, 817-824.

Tang Guomin, et al., "Integration of glucoamylase gene from *Aspergillus niger* into *Saccharomyces cerevisiae* genome and its stable expression", Chinese Journal of Biotechnology, Allerton Press, vol. 11 (4), 1995, 237-241.

Tetsuya Itoh, et al., "Nucleotide sequence of the glucoamylase gene GLU1 in the yeast Saccharomycopsis fibuligera", Journal of Bacteriology, Sep. 1987 vol. 169 No. 9, Sep. 1, 1987, 4171-4176.

Accession E9P9V2. Apr. 5, 2011 (Year: 2011).

Accession Q8TFE5. Jun. 1, 2002 (Year: 2002).

Accession U3N160. Dec. 11, 2013 (Year: 2013).

Brake, Anthony J., et al., "a-Factor-directed synthesis and secretion of mature foreign proteins in *Saccharomyces cerevisiae*", Prov. Natl. Acad. Sci., vol. 81, pp. 4642-4646, Aug. 1984 Biochemistry.

Chica, Roberto A., et al., "Semi-rational approaches to engineering enzyme activity: combining the benefits of directed evolution and rational design", Curr Opin Biotechnol. 16(4), Aug. 2005, 378-84.

Flessel, Monica C., et al., "The MFa1 Gene of *Saccharomyces cerevisiae*: Genetic Mapping and Mutational Analysis of Promoter Elements", Genetics 121: 223-236 (Feb. 1989).

Lau, W.T. Walter, et al., "A Genetic Study of Signaling Processes for Repression of PH05 Transcription in *Saccharomyces cerevisiae*", Genetics Society of America 150: 1349-1359 (Dec. 1998).

Li, Jincai , et al., "Impediments to Secretion of Green Fluorescent Protein and Its Fusion from *Saccharomyces cerevisiae*", Biotechnol. Prog. 2002, 18, 831-838.

Liu, Zengran , et al., "Integrative Expression of Glucoamylase Gene in a Brewer's Yeast *Saccharomyces pastorianus* Strain", Food Technol. Biotechnol. 46 (1) 32-37 (2008.

Sidhu, Rajinder Singh, et al., "Selection of secretory protein-enoding genes by fusion with PH05 in *Saccharomyces cerevisiae*", Gene, 107 (1991) 111-118.

Singh, Raushan Kumar, et al., "Protein Engineering Approaches in the Post-Genomic Era", Curr Protein Pept Sci. 18, 2017, 1-11.

GLUCOAMYLASE-MODIFIED YEAST STRAINS AND METHODS FOR BIOPRODUCT PRODUCTION

CROSS-REFERENCE TO RELATED APPLICATIONS

This application is a National Phase Application of International Application No. PCT/US2016/024249, filed Mar. 25, 2016, and entitled "GLUCOAMYLASE-MODIFIED YEAST STRAINS AND METHODS FOR BIOPRODUCT PRODUCTION", which claims the benefit of U.S. Provisional Application No. 62/139,312, filed on Mar. 27, 2015, entitled "GLUCOAMYLASE-MODIFIED YEAST STRAINS AND METHODS FOR BIOPRODUCT PRODUCTION", both of which are hereby incorporated by reference herein in their entirety.

SEQUENCE LISTING

This application contains a Sequence Listing which has been submitted electronically in ASCII text file format, entitled "N00294_ST25.txt," created on Sep. 27, 2017, and having a size of 79 kilobytes, which is hereby incorporated by reference in its entirety.

FIELD OF THE INVENTION

The current invention relates to genetically modified yeast having multiple nucleic acids encoding a heterologous glucoamylase gene, fermentations methods for producing a bioproduct, such as ethanol, and also reduced glycerol production.

BACKGROUND

Ethanol production by fermentation is a well know industrial process. However increasing ethanol yields can be technically difficult. There are various factors that make it challenging for microorganisms to grow in fermentation conditions designed for increased ethanol production. For example, the fermentation media may have higher substrate concentrations to promote ethanol production, but these conditions can have a negative impact on cell growth. Also, increased ethanol concentration and accumulation of undesirable byproducts can also be detrimental to cell health. Yeast strains have been selected for tolerance to these conditions, which can result in improved ethanol yields. In particular, the ethanol tolerant strains of the yeast *Saccharomyces cerevisiae* have been used in industrial settings as a workhorse microorganism for producing ethanol.

Molecular techniques have led to the identification of genes that are associated with ethanol tolerance. For example, Kajiwara (Appl. Microbiol. Biotechnol. 2000; 53:568-74) reports that overexpression of the OLE1 gene which is involved in unsaturated fatty acid (UFA) synthesis resulted in higher unsaturated fatty acid levels in the cell and higher ethanol production. Other research has found that accumulation of trehalose by disruption of the trehalose-hydrolyzing enzyme, acid trehalase (ATH) (Kim et al., Appl. Environ. Microbiol. 1996; 62:1563-1569) or accumulation of proline L-proline by a strain carrying a PRO1 gamma-glutamyl kinase mutation (Takagi, et al., Appl. Environ. Microbiol. 2005; 71:8656-8662) improves ethanol tolerance in yeast. Ergosterol is closely associated with ethanol tolerance of *Saccharomyces cerevisiae* (Inoue, et al., Biosci. Biotechnol. Biochem. 2000; 64:229-236). While advancements have been made in this area, use of genetically modified strains that demonstrate ethanol tolerance may not alone be sufficient to provide desired levels of ethanol during a fermentation process.

In addition to the genetic profile of the fermentation microorganism, the components of the fermentation media can have a significant impact on ethanol production. In fermentation processes, a carbohydrate or carbohydrate mixture is present in the media. Starch is a widely available and inexpensive carbohydrate source. It is available from a wide variety of plant sources such as corn, wheat, rice, barley, and the like. Many organisms are not capable of metabolizing starch directly, or else metabolize it slowly and inefficiently.

Accordingly, it is common to treat starch before feeding it into the fermentation process, in order to break it down into monosaccharides that the organism can ferment easily. Usually, starch is hydrolyzed to form a mixture containing mainly glucose (i.e., dextrose). However, the pre-treatment of a starch composition in preparation for fermentation can be expensive and labor intensive as it commonly involves the addition of purified starch-degrading enzymes to the starch material and requires additional steps prior to carrying out fermentation. Further, complete hydrolysis to glucose adds significant cost, so most commercially available glucose products tend to contain a small amount of various oligomeric polysaccharides.

A significant portion of the cost to produce starch based ethanol is the enzymes that break down the starch into fermentable sugars. Various molecular techniques have been attempted in *Saccharomyces cerevisiae* to reduce or eliminate the need to add amylolytic enzymes to the fermentation media, but these approaches have yielded varying degrees of success. A potential limiting factor affecting the commercial viability of engineered strains is the ability of *Saccharomyces cerevisiae* to secrete large amounts of foreign protein.

SUMMARY OF THE INVENTION

The invention relates to fermentation methods for producing a bioproduct including an engineered yeast having a heterologous glucoamylase. In one aspect, the current invention relates to engineered yeast strains expressing a heterologous glucoamylase, or two or more heterologous glucoamylases with high sequence identity to each other, wherein the one or more glucoamylase(s) is encoded by multiple exogenous nucleic acids which are different from each other. The engineered yeast strain expresses the heterologous glucoamylase and is able to produce high levels of a bioproduct, such as ethanol, in a fermentation product.

In one aspect, the invention provides an engineered yeast comprising at least first, second, third, and fourth exogenous nucleic acids. In some cases, each exogenous nucleic acid can includes a sequence encoding a common glucoamylase polypeptide that is heterologous to the yeast species, and the first, second, third, and fourth exogenous nucleic acids have nucleic acid sequences that are different from one another. In other cases, the first, second, third, and fourth exogenous nucleic acids have nucleic acid sequences that are different and encode two or more glucoamylase polypeptides heterologous to the yeast species and which have sequence identity to each other of greater than 90%. Optionally, the microorganism can include additional nucleic acids (fifth, sixth, etc.) that encode a common glucoamylase polypeptide or two or more glucoamylase polypeptides with high identity. In aspects, the engineered yeast is a species of *Saccharomyces*.

In exemplary aspects, the glucoamylase polypeptide is, or glucoamylase polypeptides are, at least 90% identical to SEQ ID NO:11, which in a glucoamylase of a strain of the yeast *Saccharomycopsis fibuligera*. In some aspects, the first, second, third, and fourth exogenous nucleic acids differ from each other by at least 10%, for example, by an amount in the range of 10% to 30%. In some aspects, the first, second, third, and fourth exogenous nucleic acids are unique codon-optimized sequences that code for a glucoamylase enzyme and provide efficient expression of the nucleic acids in the host cell.

In some aspects, the first and second nucleic acids are integrated into a first allele, and the third and fourth nucleic acids are integrated into a second allele, of a non-essential gene in the yeast, such as CYB2 in a *Saccharomyces* species. In some aspects, two more sets of the nucleic acid (e.g., the first and third, and/or the second and fourth nucleic acids) are under the control of a common promoter, such as a TDH3 or a PGK promoter.

In some aspects, the invention provides a method for producing a bioproduct, the method comprising fermenting a liquid media comprising a starch material and an engineered yeast comprising the at least first, second, third, and fourth exogenous nucleic acids. In some aspects, the bioproduct is ethanol, and the method of fermenting provides an ethanol concentration of about 90 g/L or greater in the liquid media, such as an amount in the range of about 90 g/L to about 170 g/L. In some aspects, the invention provides a fermentation media comprising the engineered microorganism having any of the genetic modifications as described herein.

In some aspects, the invention provides engineered yeast and methods for fermentation, wherein the cells produce less glycerol in a fermentation method than a parent strain. The engineered yeast can include one or more genetic modifications of the disclosure that results in the cell producing less glycerol than a parent strain that does not include the one or more genetic modification(s).

In some aspects, the method of producing a bioproduct also includes reducing the amount of glycerol produced in a fermentation method, wherein the method comprises culturing a microorganism having one or more genetic modifications of the disclosure that produces less glycerol than a parent strain that does not include the genetic modifications.

In some aspects, the invention provides a nucleic acid having 85% or greater sequence identity to any one of the following sequences: SEQ ID NO: 5-8. The invention also provides nucleic acids having a promoter, terminator, or both, operationally linked to the nucleic acid sequence, and as well as vectors comprising the nucleic acids.

The invention also provides a engineered microorganism that is a species of *Saccharomyces* comprising at least first, second, third, and fourth exogenous nucleic acids, that encode a glucoamylase polypeptide that is heterologous to the *Saccharomyces* species, wherein the glucoamylase polypeptide has a modified N-terminus that includes a *Saccharomyces cerevisiae* mating factor alpha 2 (ScMFα2) secretion signal or a *Saccharomyces cerevisiae* repressible acid phosphatase (ScPHO5) secretion signal.

In another aspect, the invention provides a fermentation method for producing ethanol. In the method a fermentation medium that includes a partially hydrolyzed starch (such as partially hydrolyzed corn starch) and an engineered yeast is provided. Throughout the fermentation period, a liquid medium comprising hydrolyzed starch is added to the fermentation medium. The engineered yeast includes at least one genetic modification providing a heterologous glucoamylase that is secreted into the medium, the at least one genetic modification being stable over the fermentation period. The fermentation period is for a period of time of five days or greater. In the fermentation method the heterologous glucoamylase facilitates the production of ethanol to a concentration of 130 g/L or greater in the fermentation medium.

In another aspect, the invention provides methods and compositions that can be used to prepare feed compositions. The feed compositions which fermentation medium co-products obtained from a fermentation medium include the engineered yeast of the disclosure. For example, after a fermentation process has been completed, some or all of a bioproduct can be removed from the fermentation medium to provide a refined composition comprising non-bioproduct solids. The non-bioproduct solids can include the engineered yeast, feedstock material in the medium that is not utilized by the yeast, as well as fermentation by-products. The refined composition can be used to form a feed composition, such as a livestock feed composition. The refined composition comprising non-bioproduct solids can provide carbohydrate and protein supplements to improve the nutritional content of a feed composition.

DETAILED DESCRIPTION

Figure 1:
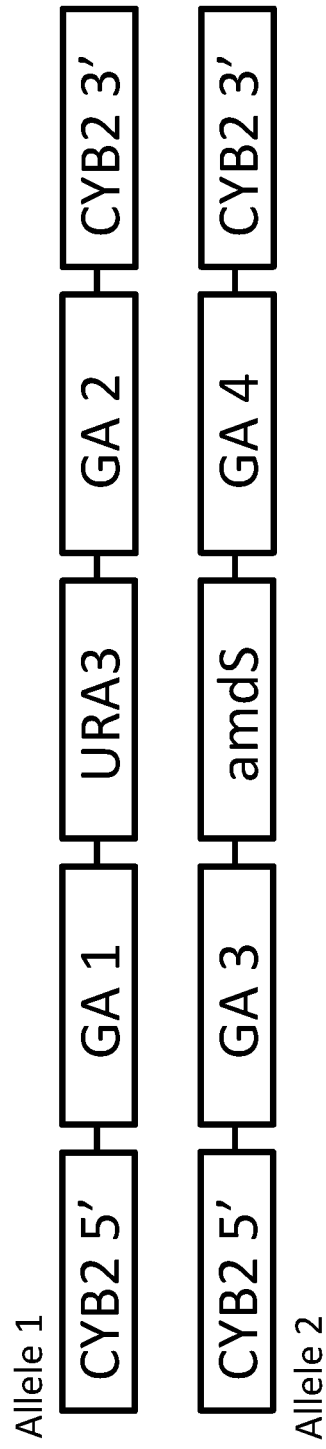
FIG. 1 is a schematic diagram of an engineered CYB2 loci showing arrangement of four unique codon optimized nucleic acids sequences encoding Sf GA and marker genes (Strain 1-5).

The aspects of the present invention described below are not intended to be exhaustive or to limit the invention to the precise forms disclosed in the following detailed description. Rather a purpose of the aspects chosen and described is so that the appreciation and understanding by others skilled in the art of the principles and practices of the present invention can be facilitated.

Aspects of the invention relate to engineered yeast strains expressing a heterologous glucoamylase, or two or more heterologous glucoamylases, wherein the glucoamylase is encoded by multiple exogenous nucleic acids which are different from each other. The engineered yeast strain is able to produce high levels of a bioproduct, such as ethanol, in a fermentation process. Further, the engineered yeast strain is able to produce lower levels of glycerol in a fermentation process.

The glucoamylase enzyme can be secreted from the cell to a fermentation media where the enzyme can have amylolytic activity on glucose polymers present in the fermentation media. In turn, the enzyme can cause degradation of the glucose polymers to glucose, which can enter the cell and be used as a carbon source for the production of a target compound, such as ethanol.

Nucleic acids that are templates for the expression of these enzymes are also aspects of the invention, as well as constructs including these nucleic acids.

The term "exogenous" as used herein, means that a molecule, such as a nucleic acid, or an activity, such as an enzyme activity, is introduced into the host organism. An exogenous nucleic acid can be introduced in to the host organism by well-known techniques and can be maintained external to the hosts chromosomal material (e.g., maintained on a non-integrating vector), or can be integrated into the host's chromosome, such as by a recombination event. An exogenous nucleic acid can encode an enzyme, or portion thereof, that is either homologous or heterologous to the host organism.

The term "heterologous" (e.g., "non-native") refers to a molecule or activity that is from a source that is different than the referenced molecule or organism. Accordingly, a gene or protein that is heterologous to a referenced organism is a gene or protein not found in that organism. In the context of the disclosure, a "heterologous glucoamylase" refers to a glucoamylase polypeptide that is different from a glucoamylase polypeptide native to the host organism. For example, a specific glucoamylase gene found in a first fungal species and exogenously introduced into a second fungal species that is the host organism is "heterologous" to the second fungal organism.

Glucoamylases (E.C. 3.2.1.3) are amylolytic enzymes that hydrolyze 1,4-linked α-D-glucosyl residues successively from the nonreducing end of oligo- and polysaccharide chains with the release of D-glucose. Glucoamylases can also cleave α-1,6 bonds on amylopectin branching points. As used herein, the term "amylolytic activity" with reference to the heterologous glucoamylase pertains to these enzymatic mechanisms. A glucoamylase polypeptide can be a variant of a naturally occurring glucoamylase, or a portion of a naturally occurring glucoamylase (such as a glucoamylase that is truncated at its N-terminus, its C-terminus, or both), with the glucoamylase polypeptide retaining amylolytic activity.

Alternative names for glucoamylases include amyloglucosidase; γ-amylase; lysosomal α-glucosidase; acid maltase; exo-1,4-α-glucosidase; glucose amylase; γ-1,4-glucan glucohydrolase; acid maltase; 1,4-α-D-glucan glucohydrolase.

Most glucoamylases are multidomain enzymes. Many glucoamylases include a starch-binding domain connected to a catalytic domain via an O-glycosylated linker region. The starch-binding domain may fold as an antiparallel beta-barrel and may have two binding sites for starch or beta-cyclodextrin. However, some glucoamylases do not include a starch binding domain (e.g., see Hostinova et al., Archives of Biochemistry and Biophysics, 411:189-195, 2003), or include a non-canonical starch binding domain. For example, the *Rhizopus oryzae* glucoamylase possesses an N-terminal raw starch binding domain, and the *Saccharomycopsis fibuligera* IFO 0111 glucoamylase lacks a clear starch binding domain (Hostinova et al., supra).

Glucoamylases may also have a catalytic domain having a configuration of a twisted (alpha/alpha)(6)-barrel with a central funnel-shaped active site. Glucoamylases may have a structurally conserved catalytic domain of approximately 450 residues. In some glucoamylases the catalytic domain is generally followed by a linker region consisting of between 30 and 80 residues that are connected to a starch binding domain of approximately 100 residues.

Glucoamylase properties may be correlated with their structural features. A structure-based multisequence alignment was constructed using information from catalytic and starch-binding domain models (see, e.g., Coutinho, P. M., and Reilly, P. J., 1994. Protein Eng. 7:393-400 and 749-760). It has been shown that the catalytic and starch binding domains are functionally independent based on structure-function relationship studies, and there are structural similarities in microbial glucoamylases. From other studies, specific glucoamylase residues have been shown to be involved in directing protein conformational changes, substrate binding, thermal stability, and catalytic activity (see, for example, Sierks, M. R., et al. 1993. Protein Eng. 6:75-79; and Sierks, M. R., and Svensson, B. 1993. Biochemistry 32:1113-1117). Therefore, the correlation between glucoamylase sequence and protein function is understood in the art, and one of skill could design and express variants of amylolytically active glucoamylases having one or more amino acid deletion(s), substitution(s), and/or additions.

In a preferred aspect of the disclosure the host *Saccharomyces* has at least first, second, third, and fourth exogenous nucleic acids (and which are different from one another) each including a sequence encoding at least one glucoamylase polypeptide that has at least 90% identity to the Glm glucoamylase from the yeast strain *Saccharomycopsis fibuligera* IFO 0111. Hostinova et al. (Archives of Biochemistry and Biophysics, 411:189-195, 2003) describes the nucleotide sequence of the glucoamylase gene Glm in the yeast strain *Saccharomycopsis fibuligera* IFO 0111 (i.e., a "Sf GA" polypeptide). According to Hostinova et al., the *Saccharomycopsis fibuligera* Glm gene is transcribed into a 1.7 kb RNA transcript that codes for a 515 amino acid protein, and is represented by SEQ ID NO:11. In the 515 amino acid-long polypeptide chain 26 N-terminal amino acid residues constitute the signal peptide and subsequent 489 amino acid residues constitute the mature protein. Mature Glm, which lacks the signal sequence and is 489 amino acids long, has a predicted molecular weight of 54,590 Da in deglycosylated form. In an alignment with other glucoamylases, Glm was shown to have homology in the catalytic domain (e.g., see the glutamic acids at positions 239 and 493 of SEQ ID NO:1).

Itoh et al. (J. Bacteriol. 169:4171-4176) describes the nucleotide sequence of another glucoamylase gene, GLU1, in the yeast *Saccharomycopsis fibuligera*. The *Saccharomycopsis fibuligera* GLU1 gene is transcribed into a 2.1 kb RNA transcript that codes for a 519 amino acid protein and has a molecular weight of 57,000 Da. GLU1 has four potential glycosylation sites (for asparagine-linked glycosides having a molecular weight of 2000 Da). GLU1 has four potential glycosylation sites (for asparagine-linked glycosides having a molecular weight of 2000 Da). GLU1 has a natural signal sequence for secretion that is cleaved off, likely during export of the protein. The cleaved site is preceded by the basic amino acids Lys-Arg, thought to be a proteolytic processing signal to yield mature protein.

Itoh et al. (supra) also describes alignment of amino acid sequences of glucoamylases from yeast and fungi. *Saccharomycopsis fibuligera*, *A. niger*, *Rhizopus oryzae*, and *Saccharomyces diastaticus*, and *Saccharomyces cerevisiae* were aligned showing five highly homologous segments (S1-S5). These parts of the respective conserved segments were shown to be conformationally similar to each other. The S5 segment, generally located at the carboxy termini, appears to be nonessential to amylolytic activities, since glucoamylases from *Saccharomyces* species lack this region.

In this regard, the invention also contemplates variants and portions of Sf GA having glucoamylase activity. Tables 1 and 2 presents a list of various fungal and bacterial glucoamylase genes, including the amino acid location of the native signal sequence, and in some sequences, the propeptide, of the glucoamylase polypeptide.

TABLE 1

| | | Fungal Glucoamylases | | | |
|---|---|---|---|---|---|
| Name | Accession | Organism | Signal peptide | Pro-peptide | Chain |
| GAMP (AMYG_AMORE) | Q03045 | *Amorphotheca resinae* (Creosote fungus) (*Hormoconis resinae*) | 1-29 | | 30-616 |
| GLAA (AMYG_ASPNG) | P69328 | *Aspergillus niger* | 1-18 | 19-24 | 25-640 |
| STA1 (AMYH_YEASX) | P04065 | *Saccharomyces cerevisiae* | 1-21 | | 22-767 |
| STA2 (AMYI_YEASX) | P29760 | *Saccharomyces cerevisiae* | 1-21 | | 22-768 |
| GLAA (AMYG_ASPAW) | P69327 | *Aspergillus awamori* (Black koji mold) | 1-18 | 19-24 | 25-640 |
| glaA (AMYG_ASPOR) | P36914 | *Aspergillus oryzae* (strain ATCC 42149/RIB 40) (Yellow koji mold) | 1-19 | 20-25 | 26-612 |
| GAA (AMYG_BLAAD) | P42042 | *Blastobotrys adeninivorans* (Yeast) (*Arxula adeninivorans*) | 1-18 | | 19-624 |
| GAM1 (AMYG_SCHOC) | P22861 | *Schwanniomyces occidentalis* (Yeast) (*Debaryomyces occidentalis*) | 1-22 | | 23-958 |
| gaI (AMYG_ASPKA) | P23176 | *Aspergillus kawachii* (White koji mold) (*Aspergillus awamori* var. *kawachi*) | 1-18 | 19-24 | 25-639 |
| glaA (AMYG_ASPSH) | P22832 | *Aspergillus shirousami* | 1-18 | 19-24 | 25-639 |
| GAM1 (AMYG_CANAL) | O74254 | *Candida albicans* (strain SC5314/ATCC MYA-2876) | 1-20 | | 21-946 |
| AMYG_RHIOR | P07683 | *Rhizopus oryzae* (Mucormycosis agent) (*Rhizopus arrhizus* var. *delemar*) | 1-25 | | 26-604 |
| meu17 (mAMYG_SCHPO) | O60087 | *Schizosaccharomyces pombe* (strain 972/ATCC 24843) (Fission yeast) | 1-16 | 17-28 | 29-450 |
| | I2K2N7 | *Brettanomyces bruxellensis* AWRI1499 | 1-21 | | 22-575 |
| SGA1 | A0A0H5C3I6 | *Cyberlindnera jadinii* (Torula yeast) (*Pichia jadinii*) | 1-16 | | 17-577 |
| GLA1 (AMYH_SACFI) | P26989 | *Saccharomycopsis fibuligera* (Hostinova et al. 2001) | 1-27 | | 28-519 |
| GLU1 AMYG_SACFI | P08017.1 | *Saccharomycopsis fibuligera* (Itoh et al. 1987) | 1-27 | | 28-519 |
| Glm SEQ ID NO: 11 | CAC83969 | *Saccharomycopsis fibuligera* IFO 0111 (Hostinova et al. 2003) | 1-26 | | 27-515 |

TABLE 2

Bacterial Glucoamylases

| Amylase gene | Accession | Organism | Signal peptide | Pro-peptide | Chain |
|---|---|---|---|---|---|
| SusB (SUSB_BACTN) | G8JZS4 | Bacteroides thetaiotaomicron (strain ATCC 29148/DSM 2079/NCTC 10582/E50/VPI-5482) | 1-21 | | 22-738 |
| cga (AMYG_CLOS0) | P29761 | Clostridium sp. (strain G0005) | 1-21 | | 22-702 |

Any polypeptide sequence(s) of a functional glucoamylase can be expressed by the four or more different glucoamylase nucleic acid sequences. In some aspects, the glucoamylase nucleic acid sequences can encode for one or more native ("wild type") sequence(s) of a glucoamylase polypeptide (i.e., the glucoamylase polypeptide sequence(s) do not differ from the native sequence at any amino acid position). In other aspects, the sequence of the glucoamylase polypeptide differs from the native sequence at one or more amino acid position(s) (e.g., a "variant" of a native glucoamylase polypeptide). The difference can be, for example, (a) the removal of one or more amino acids from the wild type sequence, (b) the addition of one or more amino acids to the wild type sequence, (c) the substitution of the wild type sequence, a combination of (a) and (c), or a combination of (b) and (c).

In some aspects, the glucoamylase nucleic acids introduced into the Saccharomyces species encode one (i.e., a common glucoamylase), or more than one, glucoamylase polypeptide that has about 90% or greater sequence identify to SEQ ID NO:11 (Glm glucoamylase from Saccharomycopsis fibukgera IFO 0111). In more specific aspects, the glucoamylase nucleic acids introduced into the Saccharomyces species encode one, or more than one, glucoamylase polypeptide that has 95% or greater, 96% or greater, 97% or greater, 98% or greater, or 99% or greater sequence identity to SEQ ID NO:11. The difference in identity with SEQ ID NO:11 can be due to one or more amino acid substitutions in one or more region(s) of the polypeptide, for example, in regions outside of those understood to be important for enzyme activity and/or outside of conserved regions based on alignment with one or more other glucoamylase(s).

For example, with reference to SEQ ID NO:11, in one aspect the one or more substitutions are at any of the following locations, which represent amino acid positions having a lower degree of identity between SEQ ID NO:11 and other glucoamylases. For example, an alignment of SEQ ID NO:11 with other glucoamylases is illustrated in a primary structure alignment provided in Hostinova and Gasperik (Biologia 65:559-568; 2010). The substitution locations according to SEQ ID NO:11 are: 1M-5T, 7F, 9T, 10A, 15V, 16A, 18C, 19V, 21V, 22E, 24D, 27N-30H, 32Q, 36G, 38T, 40A, 42S-50E, 52P, 53A, 56W, 64D, 71K-74K, 77V, 79V, 86E, 90F, 97T, 103S-106A, 108V, 111H, 112S, 114S, 121V, 127S-129T, 131T, 135V, 141N, 144S, 145P, 148D, 157V, 159D, 160T, 164A, 165S, 187A, 189A-191H, 193N, 197L, 199A-203G, 205P, 206Y, 209A, 210S, 214W, 215K, 222Q, 223H, 225S-227H, 229S-231S, 242T, 247A, 251L, 255S, 257G-261S, 263T-265N, 267P, 268P, 270T-272W, 274E-270A, 281N, 284I-286S, 292S-295K, 300S, 302Q, 304S, 307G, 316A, 317A, 319I, 325D-329Y, 333N, 337S, 341N, 343L, 345Y, 348V, 352N, 355K, 356I, 358G, 359N, 361K, 366V, 377V, 379T, 386Q, 393, G, 395T, 396F, 398T, 402N-411V, 413E, 415L, 419L, 420Y, 422S, 423F, 425A, 429K, 431D, 433S, 435A, 437K, 440L, 442L-444Y, 448N-451N, 453I-455S, 457L, 458Q, 465K, 467L, 472D, 474N, 476Q, 478T, 480E, 481I, 487F-489A, 492V, 500S, 503S, 505N, 507A, 511L-513E, and 515L.

If the glucoamylase polypeptide sequence differs from the wild type sequence the glucoamylase polypeptide can include, for example, up to about 5, 10, 15, 20, 25, 30, 35, 40, 45, or 50 amino acid substitutions at any of the low identity locations as listed with reference to SEQ ID NO:11. In some cases, the substitution can be a conservative substitution, such as where one amino acid of a particular type (e.g., polar, non-polar/aliphatic, positively charged/basic, negatively charged/acidic) is replaced with an amino acid of the same type.

If the four (or more) exogenous nucleic acid sequences encode two or more glucoamylase polypeptides that are different from one another, then the two or more glucoamylase polypeptides can also have substitutions, such as described herein, and about 90% or greater sequence identify to SEQ ID NO:11. That is, the exogenous nucleic acid sequences, which have different sequences, can encode glucoamylases that also have distinct sequences but that are close enough in identity to function similarly, having glucoamylase activity.

In other aspects, the glucoamylase sequence optionally comprises additional sequence that is not present in the native glucoamylase polypeptide. The additional sequence can provide functionality to the glucoamylase that is not present in the native polypeptide. Additional functionalities include, for example, protease sites or binding sites for other proteins or materials.

An example of an additional sequence that may not be present in the native glucoamylase polypeptide, but that can be added, is a tag sequence. A tag sequence can be located at the C-terminus of the glucoamylase sequence, and such proteins can be annotated as follows: [GA]-[T], wherein "T" denotes one or more amino acids that provide the tag sequence. Exemplary peptide tags include up to 5, 10, 15, or 20 amino acids. The peptide tag can be useful for any one or more of a variety of purposes. For example, the tag can allow purification of the enzyme from the media by the ability of a tag-binding member to specifically interact with the tag. The tag can also allow detection or identification of the protein using a tag-binding member with a detectable label. Exemplary short peptide tags are poly-Arg, FLAG, poly-His, c-myc, S, and Strep II.

Glucoamylase polypeptides of the disclosure can also have deletions to one or more regions of the native glucoamylase polypeptide, wherein the deletions do not affect the polypeptides' amylolytic activity. The deletions can be based on known information regarding the structure and function of native glucoamylases, including mutational studies and sequence alignments (e.g., see Coutinho, supra, and Sierks, supra.). In some aspects the glucoamylase polypeptide has up to 1%, up to 2%, up to 4%, up to 6%, up to 8%, up to 10%, up to 12%, up to 14%, up to 16%, up to 18%, up to 20%, or up to 25% of its amino acid sequence deleted. For example, in some aspects, the glucoamylase polypeptide can have a deletion of a portion of the C-terminus corresponding to the native glucoamylase polypeptide.

Truncated forms of glucoamylase have been generated and have been shown to have enzymatic activity. For example Evans et al. (Gene, 91:131; 1990) generated a series of truncated forms of glucoamylase to investigate how much of the O-glycosylated region was necessary for the activity or stability of GAII, a fully active form of the enzyme lacking the raw starch-binding domain. It was found that a significant portion of the C-terminus could be deleted from GAII with insignificant effect on activity, thermal stability, or secretion of the enzyme.

Various amino acids substitutions associated with causing a change in glucoamylase activity are also known in the art. Substitution(s) of amino acid(s) at various locations in the glucoamylase sequence have been shown to affect properties such as thermostability, starch hydrolysis activity, substrate usage, and protease resistance. As such, the current disclosure contemplates a host cell having multiple unique exogenous nucleic acids, each expressing a glucoamylase sequence that includes one or more amino acid(s) substitution(s) in the glucoamylase portion of the polypeptide, wherein the substitutions differ from the wild type sequence of the glucoamylase.

For example, U.S. Pat. No. 8,809,023 describes a method for reducing the ratio between isomaltose synthesis and starch hydrolysis activity (IS/SH ratio) during the hydrolysis of starch. In particular a *Trichoderma reesei* glucoamylase (Tr GA) is described (total length of 632 amino acids having an N-terminal having a signal peptide) that is modified at with amino acid positions as follows: D44R and A539R; or D44R, N611, and A539R. This glucoamylase variant is reported to exhibit a reduced IS/SH ratio compared to said parent glucoamylase during the hydrolysis of starch. As an example, the current disclosure contemplates amino acid substitutions corresponding to the D44R and A539R; or D44R, N611 and A539R substitutions of the modified Tr GA. In a broader sense, the disclosure provides a host cell having multiple unique exogenous nucleic acids, each expressing a glucoamylase variant having amino acid substitutions: D44R and A539R; or D44R, N611 and A539R, the positions corresponding to the respective position in the TrGA sequence, wherein said glucoamylase variant has at least 90% amino acid sequence identity to the entire length of the TrGA sequence. The corresponding "respective position" of a template glucoamylase sequence to the TrGA sequence can be understood by a sequence alignment of, for example, known glucoamylase polypeptide sequences (the template for construction of a glucoamylase gene), to the TrGA sequence.

As another example, U.S. Pat. No. 8,592,194 describes glucoamylase variants with increased thermo stability compared to wild type glucoamylase variants. Also described in this disclosure is the *Trichoderma reesei* glucoamylase but instead one or more amino acid substitutions to the native Tr GA sequence at positions 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, and 418. As an example, the current disclosure contemplates a Sf GA sequence that further has any one or more of the amino acid substitutions that are demonstrated to provide increased thermostability. In a broader sense, the disclosure provide a host cell having multiple unique exogenous nucleic acids, each expressing having with a glucoamylase variant having amino acid substitutions providing increased thermo stability, the positions corresponding to the respective position in the Tr GA sequence.

The determination of "corresponding" amino acids from two or more glucoamylases can be determined by alignments of all or portions of their amino acid sequences. Sequence alignment and generation of sequence identity include global alignments and local alignments, which typically use computational approaches. In order to provide global alignment, global optimization forcing sequence alignment spanning the entire length of all query sequences is used. By comparison, in local alignment, shorter regions of similarity within long sequences are identified.

As used herein, an "equivalent position" means a position that is common to the two sequences (e.g., a Sf GA sequence and a GA sequence having the desired substitution(s)) that is based on an alignment of the amino acid sequences of one glucoamylase or as alignment of the three-dimensional structures. Thus either sequence alignment or structural alignment, or both, may be used to determine equivalence.

In some modes of practice, the BLAST algorithm is used to compare and determine sequence similarity or identity. In addition, the presence or significance of gaps in the sequence which can be assigned a weight or score can be determined. These algorithms can also be used for determining nucleotide sequence similarity or identity. Parameters for to determine relatedness are computed based on art known methods for calculating statistical similarity and the significance of the match determined. Gene products that are related are expected to have a high similarity, such as greater than 50% sequence identity. Exemplary parameters for determining relatedness of two or more sequences using the BLAST algorithm can be as follows.

In some modes of practice, an alignment is performed using BLAST (National Center for Biological Information (NCBI) Basic Local Alignment Search Tool) version 2.2.29 software with default parameters. A sequence having an identity score of XX % (for example, 80%) with regard to a reference sequence using the BLAST version 2.2.29 algorithm with default parameters is considered to be at least XX % identical or, equivalently, have XX % sequence identity to the reference sequence. A global alignment can be used to align sequences with significant identity to, for example, the *S. fibuligera* Glm glucoamylase (SEQ ID NO:11) in order to determine which corresponding amino acid position(s) in the target sequence (e.g., a glucoamylase ortholog) can be substituted with the one or more of the amino acid if a glucoamylase variant is used.

As noted herein and in Tables 1 and 2, glucoamylases enzymes from various fungal and bacterial species also generally include a native "signal sequence." Various other terms may be used to indicate a "signal sequence" as known in the art, such as where the word "signal" is replaced with "secretion" or "targeting" or "localization" or "transit" or leader," and the word "sequence" is replaced with "peptide" or "signal." Generally, a signal sequence is a short amino acid stretch (typically in the range of 5-30 amino acids in length) that is located at the amino terminus of a newly synthesized protein. Most signal peptides include a basic N-terminal region (n-region), a central hydrophobic region (h-region) and a polar C-terminal region (c-region) (e.g., see von Heijne, G. (1986) Nucleic Acids Res. 14, 4683-4690). A signal sequence can target the protein to a certain part of the cell, or can target the protein for secretion from the cell. For example, it has been shown that the native N-terminal signal sequence of the *S. diastaticus* Glucoamylase STAI gene can target it to the endoplasmic reticulum of the secretory apparatus (for example, see Yamashita, I. et al., (1985) J. Bacteriol. 161, 567-573).

In some aspects, the exogenous nucleic acids introduced into the host cell encode a heterologous glucoamylase enzyme with a Sc MFα2 or a Sc PHO5 secretion signal. In such aspects, the enzymes can be referred to as "fusion proteins" as they include portions from two different polypeptides, and can be annotated as follows: [Sc MFα2-SS]-[GA] and [Sc PHO5-SS]-[GA].

The *Saccharomyces cerevisiae* mating factor alpha 2 (Sc MFα2) secretion signal is described in U.S. Pat. No. 4,546,082 (Kurjan et al.). The Sc MFα2 SS sequence is as follows: MKFISTFLTFILAAVSVTA (SEQ ID NO: 12). The Sc MFα2 sequence is from the gene YGL089C (YGL089C), whereas MFα1 is coded by the gene YPL187W MFα1 and MFα2 are pheromones secreted by MATa cells. In some aspects, the disclosure provides a host cell having multiple exogenous nucleic acids of different sequences, each exogenous nucleic acid encoding a glucoamylase fusion protein comprising a secretion signal sequence that has 90% or greater identity to SEQ ID NO: 12.

The *Saccharomyces cerevisiae* repressible acid phosphatase (Sc PHO5) secretion signal is described in U.S. Pat. No. 5,521,086 (Scott et al.) and Meyhack et al. (EMBO J. 6:675-680, 1982) and has an amino acid sequence as follows: MFKSVVYSILAASLANA (SEQ ID NO. 13). The Sc PHO5 sequence is from PHO5 which is a structural gene that encodes a *S. cerevisiae* acid phosphatase, which is regulated by the concentration or inorganic phosphate ($P_i$) in the medium.

In some aspects, the disclosure provides a host cell having multiple exogenous nucleic acids of different sequences, each exogenous nucleic acid encoding a glucoamylase fusion protein comprises a secretion signal sequence that has 90% or greater identity to SEQ ID NO. 13. For example, one amino acid of SEQ ID NO. 13 can be substituted with an amino acid, such as a conservative amino acid.

Molecular techniques can be performed to create a nucleic acid sequence that is a template for the expression of a Sc MFα2 SS or a Sc PHO5 SS-glucoamylase gene (if the glucoamylase protein/nucleotide sequences are known in the art). Unique nucleic acids (four or more) can be prepared to encode a protein comprising the Sc PHO5 SS- or Sc MFα2 SS sequence and a glucoamylase sequence. That is, these nucleic acid sequences are different from one another, but still code for the same Sc PHO5 SS- or Sc MFα2 SS-glucoamylase polypeptide, the differences, for example, being based on the degeneracy of codons in the coding region of nucleic acid sequences.

For example, in one aspect the native sequence of the glucoamylase can be altered at its N-terminus prior to adding the Sc MFα2 SS or the Sc PHO5 SS sequence. In some aspects, all or a portion of the native glucoamylase signal sequence is removed prior to attaching the Sc MFα2 SS or the Sc PHO5 SS sequence. For example, a portion of a native leader sequence of the glucoamylase can be altered by deletion of one or more, but not all, amino acids of the native secretion signal (e.g., deletion of up to 50%, 60%, 70%, 80, 90%, or 95% of the native leader sequence). Such deletion of a portion of the native leader sequence may cause the native glucoamylase leader to lose its native functionality, which is replaced with the functionality provided by the Sc MFα2 or Sc PHO5 secretion signal. In other aspects, all of the native secretion signal can be removed from the glucoamylase polypeptide and replaced with the Sc MFα2 SS or the Sc PHO5 SS sequence.

For example, and with reference to Table 1, in preparing a fusion protein construct, the first 18 amino acids of the *S. fibuligera* IFO 0111 glucoamylase (Glm), which corresponds to the predicted leader sequence using the CBS prediction server (i.e., amino acids 1-18 of SEQ ID NO:11), is removed. Therefore, a portion of the *S. fibuligera* glucoamylase native secretion signal is replaced with the Sc MFα2 SS sequence (SEQ ID NO:12; 19 amino acids) or with the Sc PHO5 SS sequence (SEQ ID NO:13; 17 amino acids) which can then be attached directly or indirectly to the remaining portion of the *S. fibuligera* glucoamylase polypeptide (e.g., amino acids 19-515 of SEQ ID NO:11). This provides a Sc MFα2 SS-Sf GA of 516 amino acids (SEQ ID NO:14) or a Sc PHO5 SS-Sf GA of 514 amino acids (SEQ ID NO:15). After the desired amino acid sequence is known, unique nucleic acid sequences coding for the polypeptide can be prepared.

An additional sequence that may not be present in the native glucoamylase polypeptide, or either the Sc PHO5 SS- or Sc MFα2 SS sequences, can be added as a linker or spacer sequence. A linker sequence can be located between the Sc PHO5 SS- or Sc MFα2 SS sequence and the glucoamylase sequence. Such fusion polypeptides can be annotated as follows: [Sc MFα2-SS]-[L]-[GA] and [Sc PHO5-SS]-[L]-[GA], wherein "L" denotes one or more amino acids that link the signal sequence to the glucoamylase. Exemplary linkers include up to 5, 10, 15, 20, 25, 30, 35, or 40 amino acids. A linker can include amino acids that cause the linker to be rigid and prevent interactions between the secretion signal and other portions of the glucoamylase. Rigid linkers may include residues such as Pro, Arg, Phe, Thr, Glu, and Gln. Alternatively, the fusion polypeptide can include a flexible linker. Flexible linkers can include glycine residues and connect the signal sequence to the glucoamylase portion of the fusion protein without interfering with their respective functions. In some aspects the polypeptide includes a linker having a protease cleavage sequence. Exemplary protease cleavage sequences include those for thrombin, factor Xa, rhinovirus 3C, TEV protease, Ssp DnaB, intein, Sce VMA1 intein, enterokinase, and KEX2 (see, for example, Waugh, D. S., Protein Expr Purif. 80(2): 283-293, 2011; Zhou et al., Microbial Cell Factories 13:44, 2014; and Bourbonnais et al., J. Bio. Chem. 263(30):15342, 1988)

Exogenous nucleic acids that are templates for a common glucoamylase polypeptide can be introduced into a host cell. At least four nucleic acids, each having a different nucleic acid sequence but that encode the same glucoamylase polypeptide, are provided and introduced into a host cell for expression. In other words, none of the exogenous glucoamylase genes have the same nucleic acid sequence even though they may, in some aspects, code for the same polypeptide. In other aspects, at least four polypeptides, each having a different nucleic acid sequence and that encode two or more glucoamylase polypeptides, preferably ones that have a high degree of identity to each other (e.g., at least 90%, and preferably more than 95%).

The difference in nucleic acid sequences can be based at least on degeneracy of the amino acid code. That is, the difference in nucleic acid sequences between the versions of the glucoamylase genes are a result of changes in the second and/or third nucleotide in at least one codon triplet in the glucoamylase sequence. Preferably, the differences in the nucleic acid sequences are based on differences in multiple codons in the sequences.

The differences is nucleic acid sequences can be expressed as the percent difference in the number of nucleic acids between two different glucoamylase nucleic acid sequences, or can be expressed as the percent difference between the number of codons that are different between two different glucoamylase nucleic acid sequences. For example, if there is a 175 nucleotide difference between two specific glucoamylase nucleotide sequences, $GA_1$ and $GA_2$, each having 1545 nucleotides and encoding a common GA polypeptide, the percent nucleotide sequence difference would be approximately 11.3% (or conversely, the percent identity would be 88.7%). In some aspects, the first, second, third, and fourth exogenous nucleic acids differ from each other by at least 10%.

When each pairing provides a different sequence difference, the differences can be expressed as a range. For example, the range can be approximately an amount of the smallest difference to an amount of the largest difference. Therefore, in some aspects the first, second, third, and fourth exogenous nucleic acids can differ from each other by an amount in the range about 10% to about 30%, about 15% to about 30%, about 17% to about 27%, about 18% to about 25%, or about 19% to about 23%.

The following Table 3 is an example of the percentage of sequence differences for four glucoamylase-coding exogenous nucleic acids, $GA_1$-$GA_4$. The table details the percent difference in nucleotides between every possible pairing of nucleic acids. In some aspects, the percent difference is different for every nucleic acid pairing, and in other aspects the percent difference is the same for two or more nucleic acid pairings.

TABLE 3

Exemplary Sequence Differences

|     | $GA_1$ | $GA_2$ | $GA_3$ | $GA_4$ |
| --- | --- | --- | --- | --- |
| $GA_1$ | 0 | 22 | 19 | 20 |
| $GA_2$ | 22 | 0 | 22 | 22 |
| $GA_3$ | 19 | 22 | 0 | 23 |
| $GA_4$ | 20 | 22 | 23 | 0 |

Alternatively, the relationship between the first, second, third, and fourth exogenous nucleic acids can be explained as percent identity. Percent identity is 1% sequence difference, e.g., 1−0.22=78% sequence identity.

In yet other ways, the relationship between the first, second, third, and fourth exogenous nucleic acids can be explained as percent difference of percent identity between codons. For example, if there is a 100 codon difference (e.g., resulting from a change of 175 nucleotides between two specific glucoamylase nucleotide sequences, $GA_1$ and $GA_2$, each having 1545 nucleotides and encoding a common GA polypeptide, the percent codon difference would approximately be 6.5% (or conversely, the percent identity would be 93.5%).

Nucleic acids sequences encoding the glucoamylase polypeptide, as well as any regulatory sequence (e.g., terminator, promoter, etc.) and vector sequence (e.g., including a selection marker, integration marker, replication sequence, etc.) can, in some modes of practice, be prepared using known molecular techniques. General guidance for methods for preparing DNA constructs can be found in Sambrook et al Molecular Cloning, A Laboratory Manual, Cold Spring Harbor Laboratory Press, Cold Spring Harbor, N.Y., 1989; and Ausubel et al. Current Protocols in Molecular Biology, Greene Publishing and Wiley-Interscience, New York, N.Y., 1993.

Small amounts of glucoamylase template DNA can be used as starting material in PCR, to generate relatively large quantities of a specific DNA fragment that includes the glucoamylase gene, optionally with any additional desired sequences.

PCR techniques can be used for amplifying or modifying a native glucoamylase nucleic acid sequence to add optional heterologous sequences, such a Sc MFα2 SS or the Sc PHOS SS sequences, or to introduce one or more mutations in the glucoamylase nucleic acid sequence to provide a variant. PCR techniques are described in, for example, Higuchi, (1990) in PCR Protocols, pp. 177-183, Academic Press; Ito et al. (1991) Gene 102:67-70; Bernhard et al. (1994) Bioconjugate Chem. 5:126-132; and Vallette et al. (1989) Nuc. Acids Res. 17:723-733. The techniques may optionally include site-directed (or oligonucleotide-mediated) mutagenesis, PCR mutagenesis, and cassette mutagenesis of an earlier prepared DNA encoding a glucoamylase polypeptide.

Alternatively, nucleic acid molecules can be generated by custom gene synthesis providers such as DNA2.0 (Menlo Park, Calif.) or GeneArt (Life Technologies, Thermo Fisher Scientific).

An expression vector can be constructed to include one or more glucoamylase nucleic acid sequence(s) operably linked to expression control sequences functional in the host organism. The vectors can include selection sequences or markers operable for stable integration into a host chromosome. Additionally, the vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art.

In some aspects, the nucleic acid can be codon optimized. Nucleic acid templates used for the glucoamylase coding region can be the native DNA sequence that codes for the glucoamylase, or the template can be a codon-optimized version that is optimized for expression in a desired host cell. In some aspects, the glucoamylase sequences are codon-optimized for the expression in a *Saccharomyces* species, such as *Saccharomyces cerevisiae*. Databases that provide information on desired codon uses in particular host organisms are known in the art.

In some aspects, the glucoamylase coding regions are codon-optimized for the expression in *Saccharomyces cerevisiae* and have the following sequences: SEQ ID NO:5, SEQ ID NO:6, SEQ ID NO:7, and SEQ ID NO:8.

According to one aspect of the disclosure, a DNA construct comprising a-glucoamylase is operably linked to a promoter sequence, wherein the promoter sequence is functional in a host cell of choice. In some aspects, the promoter shows transcriptional activity in a fungal host cell and may be derived from genes encoding proteins either homologous or heterologous to the host cell. In some aspects the promoter is useful for expression in *S. cerevisiae*. Examples of well-known constitutive promoters include, but are not limited to the cytochrome c promoter (pCYC), translational elongation factor promoter (pTEF), glyceraldehyde-3-phosphate dehydrogenase promoter (pGPD) (also referred to as the TDH3 [triose phosphate dehydrogenase] promoter), phosphoglycerate kinase promoter (PGK), and alcohol dehydrogenase promoter (pADH1). Optionally, an additional factor that controls expression such as an enhancer or the like may also be included on the vector.

In some aspects a particular promoter species ($promoter_1$) provides expression control for two or more glucoamylase nucleic acid sequences. For example, organisms of the disclosure can include two DNA constructs, one construct having a glucoamylase gene under the control a first promoter (e.g., -[$promoter_a$]-[$GA_1$]-) and another construct having another glucoamylase gene also under the control a first promoter (e.g., -[$promoter_a$]-[$GA_3$]-), wherein $GA_1$ and $GA_3$ encode a common glucoamylase, but have different nucleic acid sequences. In some aspects, the promoter for $GA_1$ and $GA_3$ is selected from the glyceraldehyde-3-phosphate dehydrogenase (TDH3) promoter and a phosphoglycerate kinase (PGK) promoter. In some aspects, one of the DNA constructs (-[$promoter_a$]-[$GA_1$]-) is integrated at one allele ($geneX_1$) in the organisms genome, and the other construct (-[$promoter_a$]-[$GA_3$]-) is integrated at the corresponding allele ($geneX_2$) in the organisms genome.

In some aspects a particular promoter species ($promoter_1$) provides expression control for two or more glucoamylase nucleic acid sequences, and another particular promoter species ($promoter_2$) provides expression control for another two or more glucoamylase nucleic acid sequences. For example, organisms of the disclosure can include four DNA constructs, one construct having a glucoamylase gene under the control a first promoter (e.g., -[$promoter_a$]-[$GA_1$]-), another construct having another glucoamylase gene also under the control a first promoter (e.g., -[$promoter_a$]-[$GA_3$]-), another construct having a glucoamylase gene under the control a second promoter (e.g., -[$promoter_b$]-[$GA_2$]-), and another construct having another glucoamylase gene also under the control a second promoter (e.g., -[$promoter_b$]-[$GA_4$]-), wherein $GA_1$, $GA_2$, $GA_3$, and $GA_4$ encode a common glucoamylase, but have different nucleic acid sequences. In some aspects, the promoter for $GA_1$ and $GA_3$ is the glyceraldehyde-3-phosphate dehydrogenase (TDH3) promoter and the promoter for $GA_2$ and $GA_4$ is the phosphoglycerate kinase (PGK) promoter. In some aspects, two of the DNA constructs (-[$promoter_a$]-[$GA_1$]-, and -[$promoter_b$]-[$GA_2$]-) are integrated at one allele ($geneX_1$) in the organisms genome, and the other two DNA constructs (-[$promoter_a$]-[$GA_3$]-, and -[$promoter_b$]-[$GA_4$]-) are integrated at the corresponding allele ($geneX_2$) in the organisms genome.

An expression construct including the glucoamylase gene can also include any termination sequence functional in the host cell. For example, the termination sequence and the promoter sequence can be from the same gene, or the termination sequence is heterologous to the promoter sequence (i.e., from a different gene). In some modes of practice, the terminator comprises a ribosomal protein L3 (RPL3) terminator or a cytochrome C (CYC1) terminator.—

In some aspects a particular promoter and terminator species ($promoter_a$-$terminator_c$) pair that is heterologous to each other provides expression control for two or more glucoamylase nucleic acid sequences, and another particular promoter and terminator species ($promoter_b$-$terminator_d$) pair that are heterologous to each other provides expression control for another two or more glucoamylase nucleic acid sequences. For example, organisms of the disclosure can include four DNA constructs, one construct having a glucoamylase gene under the control a first promoter and first terminator (e.g., -[$promoter_a$]-[$GA_1$]-[$terminator_c$]), another construct having another glucoamylase gene also under the control a first promoter and first terminator (e.g., -[$promoter_a$]-[$GA_3$]-[$terminator_c$]), another construct having a glucoamylase gene under the control a second promoter and second terminator (e.g., -[$promoter_b$]-[$GA_2$]-[$terminator_d$]), and another construct having another glucoamylase gene also under the control a second promoter and second terminator (e.g., -[$promoter_b$]-[$GA_4$]-[$terminator_d$]), wherein $GA_1$, $GA_2$, $GA_3$, and $GA_4$ encode a common glucoamylase, but have different nucleic acid sequences. In some aspects, the promoter and terminator for $GA_1$ and $GA_3$ is the glyceraldehyde-3-phosphate dehydrogenase (TDH3) promoter and the cytochrome C (CYC1) terminator, and the promoter and terminator for $GA_2$ and $GA_4$ is the phosphoglycerate kinase (PGK) promoter and the ribosomal protein L3 (RPL3) terminator. In some aspects, two of the DNA constructs (-[$promoter_a$]-[$GA_1$]-[$terminator_c$], and -[$promoter_b$]-[$GA_2$]-[$terminator_d$]) are integrated at one allele ($geneX_1$) in the organisms genome, and the other two DNA constructs (-[$promoter_1$]-[$GA_3$]-[$terminator_c$], and -[$promoter_2$]-[$GA_4$]-[$terminator_d$]) are integrated at the corresponding allele ($geneX_2$) in the organisms genome, wherein the organism is diploid.

The DNA constructs may be introduced into a host cell using a vector. The vector may be any vector which when introduced into a host cell is stably introduced. In some aspects, the vector is integrated into the host cell genome and is replicated. Vectors include cloning vectors, expression vectors, shuttle vectors, plasmids, phage particles, cassettes and the like. In some aspects, the vector is an expression vector that comprises regulatory sequences operably linked to the glucoamylase coding sequence.

The DNA construct comprising a glucoamylase gene can further include a selectable marker, thereby facilitating the selection in a host cell. For example, the selectable marker can be for transformed yeast. Examples of yeast selectable marker include markers commonly used for selecting for transformed yeast cells. Auxotrophic markers can be used using a gene that controls an auxotrophy, meaning that the gene enables yeast to produce a nutrient required for the growth of the yeast. Examples genes that control auxotrophies include leucine auxotrophy (LEU2), histidine auxotrophy (HISS), uracil auxotrophy (URA3, LIRAS), and tryptophan auxotrophy (TRP1).

The DNA construct may be one which is integrated into the genome and replicated together with the chromosome(s) into which it has been integrated. For example, a fungal cell may be transformed with the DNA construct encoding the glucoamylase, and integrating the DNA construct in the host chromosome(s). This integration is generally considered to be an advantage, as the DNA sequence is more likely to be stably maintained. In methods of the disclosure, the integrated glucoamylase construct can be stably maintained over the course of a fermentation period, meaning that the construct is not lost from its integration site. Accordingly, the integrated glucoamylase is able to constantly produce and secrete glucoamylase into the fermentation medium where it can act on a hydrolyzed starch substrate. Integration of the DNA constructs into the host chromosome may be performed according to conventional methods, such as by homologous or heterologous recombination.

In one mode of practice, one or more DNA construct(s) comprising the glucoamylase genes is integrated at genetic locus, wherein the integration does not have a significant adverse effect on the health of the cell. For example, the integration can be at a locus of the genome that is not known to have any polypeptide coding sequence, or at a locus of the genome that has a gene that is not essential for function under desired growth conditions, such as under fermentation conditions using a starch or a starch-derived product as the energy source. For example, in *Saccharomyces cerevisiae*, a large amount of information is available about the essentiality of open reading frames (ORFs) in its genome. See, for example, http://www-sequence.stanford.edu/group/yeast_deletion_project/deletions3.html. Given information known in the art, one of skill can choose one or more non-essential genes as targets for integrations of the one or more DNA construct(s) comprising the glucoamylase genes. Whether or not a gene is "essential" can be determined in growth conditions using rich media with glucose.

In some aspects, one or more DNA construct(s) comprising the glucoamylase genes is integrated at the non-essential gene is L-lactate cytochrome-c oxidoreductase (CYB2).

In some modes of practice the first and second nucleic acids ($GA_1$ and $GA_2$) are first integrated into a first allele, and the third and fourth nucleic acids ($GA_3$ and $GA_4$) are integrated into a second allele, of a non-essential gene in the *Saccharomyces* species. In some modes of practice both alleles of the CYB2 gene are disrupted with the exogenous glucoamylase genes.

In some aspects the integration strategy uses co-transformation of two different DNA constructs, a first construct carrying the $GA_1$ gene, and second construct carrying the $GA_2$ gene, into a one allele of a gene. This is followed by another co-transformation of another two different DNA constructs, a third construct carrying the $GA_3$, gene, and a fourth carrying the $GA_4$ gene. The first construct includes a portion of the gene targeted for integration ("GTI"; e.g., a portion of the CYB2 gene), preferably located at the 5' end of the construct; the $GA_1$ gene, flanked by desired promoter and terminator sequences; and a selectable marker gene, such as URA3. The second construct includes the selectable marker gene (e.g., URA3) preferably located at the 5' end of the construct; the $GA_2$ gene, flanked by desired promoter and terminator sequences that are different than the $GA_1$ gene; a portion of the gene targeted for integration (GTI; e.g., a portion of the CYB2 gene). The third and fourth DNA constructs can be arranged similarly to the first and second DNA constructs, but use a different selectable marker (e.g., the amdS gene from *Aspergillus* instead of URA3). Additionally, the selectable marker can be truncated in so that neither of the two transformation fragments that are co-transformed can produce a functional gene by themselves, but through homologous recombination can produce a full length functional selectable marker.

An exemplary first DNA construct has the following arrangement of genetic elements: 5'-[GTI portion]-[promoter$_a$]-[$GA_1$]-[terminator$_c$]-[selectable marker$_1$]-3'. An exemplary second DNA construct has the following arrangement of genetic elements: 5'-[selectable marker$_1$]-[promoter$_b$]-[$GA_2$]-[terminator$_d$]-[GTI portion]-3'. An exemplary third DNA construct has the following arrangement of genetic elements: 5'-[GTI portion]-[promoter$_a$]-[$GA_3$]-[terminator$_c$]-[selectable marker$_2$]-3'. An exemplary fourth DNA construct has the following arrangement of genetic elements: 5'-[selectable marker$_2$]-[promoter$_b$]-[$GA_4$]-[terminator$_d$]-[GTI portion]-3'.

Various host cells can be transformed with a DNA construct including one or more glucoamylase genes. In some aspects the DNA construct is present in a bacterial cell which can be used, for example, for propagation of the nucleic acid sequence or for production of quantities of the polypeptide.

In other aspects, the host cell is a eukaryotic cell, such as a fungal cell. In aspects of the disclosure, the some aspects the glucoamylase nucleic acids can be engineered in a yeast strain. For example, the yeast can be a species of *Saccharomyces, Issatchenkia, Candida, Pichia, Yarrowia*, or *Kluyveromyces*. Exemplary yeast species include *Saccharomyces cerevisiae, Issatchenkia orientalis, Candida utilis, Pichia Stipitis, Yarrowia lipolytica, Kluyveromyces marxiannus*, and *Kluyeromyces lactis*. Engineered cells of these species have been described in the art (e.g., see WO 2007032792; Tamakawa, H. et al. (2011) Biosci Biotechnol Biochem. 75:1994-2000; Ilmen, M., et al. (2007) Appl Environ Microbiol. 73:117-123; Xie, D., et al. (2015) Appl Microbiol Biotechnol. 99: 1599-1610; Zhang, J. et al. (2014) Bioresour Technol. 152:192-201; and Gonzalez-Siso, M. I., et al. (2015) Microb Biotechnol. 8:319-330).

In some aspects the host cell has tolerance to a higher amount of a bioderived product, such as ethanol, in the fermentation media. In some aspects, the host cell is an "industrial yeast" which refers to any yeasts used conventionally in ethanol fermentation. Examples include sake yeasts, shochu yeasts, wine yeasts, beer yeasts, baker's yeasts, and the like. Sake yeasts demonstrate high ethanol fermentability and high ethanol resistance and genetic stability. Typically, an industrial yeast has high ethanol resistance and preferably is viable at ethanol concentrations of 10% or greater.

In exemplary aspects, the host cell is *S. cerevisiae*. Some *S. cerevisiae* have high tolerance to ethanol. Various strains of ethanol tolerant yeast are commercially available, such as RED START™ and ETHANOL RED™ yeast (Fermentis/Lesaffre, USA), FALI™ (Fleischmann's Yeast, USA), SUPERSTART™ and THERMOSACC™ yeast (Ethanol Technology, Wis., USA), BIOFERM™ AFT and XR™ (NABC—North American Bioproducts Corporation, GA, USA), GERT STRAND™ (Gert Strand AB, Sweden), and FERMIOL™ (DSM Specialties).

Industrial yeasts are typically prototrophic and therefore do not have an auxotrophic marker suitable for selecting for a transformant. If the host cell does not have the genetic background that would otherwise facilitate selection or retention of the glucoamylase genes within the cell upon transformation, the host cell can be engineered to introduce one or more genetic mutation(s) to establish use of a marker gene in association with and to maintain the glucoamylase genes in the cell. For example, a commercially available ethanol tolerant yeast cell can be genetically modified prior to introducing the glucoamylase genes in the cell.

A marker for a different auxotrophy can be provided by disrupting the gene that controls the auxotrophy. In one mode of practice, an ethanol tolerant strain of yeast is engineered to disrupt copies of one or more genes that control auxotrophies, such as LYS2, LEU2, HISS, URA3, URA5, and TRP1. In the case of providing uracil auxotrophy, for example, a normal ura3 gene of an ethanol tolerant yeast can be replaced with an ura3 fragment obtained from a uracil auxotrophic mutant (for example, a *Saccharomyces cerevisiae* MT-8 strain) to disrupt the normal URA3 gene. In the case of a URA3-disrupted strain, the presence/absence of a marker can be easily identified or selected by taking advantage of the fact that a URA3 gene-disrupted strain is able to grow in a medium containing 5-fluoroorotic acid (5-FOA) while a normal URA3 strain (wild-type yeast or usual industrial yeast) is not able to grow. In the case of a LYS2 gene-disrupted strain, the presence/absence of a marker can be easily identified or selected by taking advantage of the fact that a LYS2-disrupted strain is able to grow in a medium containing α-aminoadipic acid while a normal LYS2 strain (wild-type yeast or usual industrial yeast) is not able to grow. Methods for disrupting an auxotrophy-controlling gene and for selectively separating auxotrophy-controlling gene mutants may be used depending on the auxotrophy employed. Alternatively, one can employ dominant selection markers, such as the amdS from *Aspergillus nidulans* (U.S. Pat. No. 5,876,988), which allows for growth on acetamide as the sole nitrogen source; or ARO4-OFP, which allows for growth in the presence of fluoro-phenylalanine (Fukuda et. al.). These markers can be used repeatedly using the recyclable cre-loxP system, or alternatively can be used to create auxotrophic strains that allow additional markers to be utilized.

After the host cell has been engineered to provide a desired genetic background for introduction of the glucoamylases gene, one or more gene construct(s) is introduced into a cell to integrate into the genome, or to be stably maintained and allow for expression. Methods for introducing a gene construct into a host cell include transformation, transduction, transfection, co-transfection, electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the glucoamylase genes can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of the introduced nucleic acid sequences or their corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The engineered yeast of the disclosure can be provided in any suitable form. In some aspects, the engineered yeast is dehydrated to form a dry yeast composition. The dry yeast composition can have increased shelf life over wet compositions.

The engineered yeast strains expressing a heterologous glucoamylase, or two or more heterologous glucoamylases, wherein the glucoamylase is encoded by multiple exogenous nucleic acids which are different from each other, can be used in a fermentation process to make a product. The fermentation product (also referred to herein as "bioproduct") can be any product that can be prepared by enzymatic degradation of a starch material by the glucoamylase, formation of glucose, and fermentation of glucose. In aspects, the fermentation product is selected from the group consisting of: amino acids, organic acids, alcohols, diols, polyols, fatty acids, monacyl glycerides, diacyl glycerides, triacyl glycerides, sweeteners, sophorolipids, and mixtures thereof.

Other exemplary bioproducts that are organic acids or amino acids include lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, and acetic acid and derivatives thereof and salts thereof.

In some modes of practice, the engineered yeast strain having multiple exogenous nucleic acids encoding for the heterologous GA, can be used in a fermentation process to produce lactic acid. In such aspect, the glucoamylase modified yeast strain can be further modified to include a heterologous lactate dehydrogenase (LDH) gene for enhancing the production of lactic acid. Heterologous LDH genes transformed into yeast strains are described in, for example, WO 99/14335, WO 00/71738 and WO 02/42471.

The engineered yeast can also include one or other genetic modifications that are different than the modification of the glucoamylase with heterologous signal sequence. For example, one or more additional modifications can include those that provide a different polysaccharide-degrading enzyme, such as an exogenous or modified alpha-amylase, beta-amylase, pullulanase, isoamylase, or cyclodextrin glycosyltransferases; an exogenous or modified sugar transporter gene (such as an isomaltose transporter); and/or an exogenous or modified gene that converts a low molecular weight non-glucose sugar to glucose, such as an isomaltase.

Fermentation using a host cell expressing the glucoamylase genes can be performed in the presence of a starch and/or sugar containing plant material, referring to a starch and/or sugar containing plant material derivable from any plant and plant part, such as tubers, roots, stems, leaves and seeds. Starch and/or sugar comprising plant material can be obtained from cereal, such as barley, wheat, maize, rye, sorghum, millet, barley, potatoes, cassava, or rice, and any combination thereof. The starch- and/or sugar comprising plant material can be processed, such as by methods such as milling, malting, or partially malting. In some aspects, the starch material is from corn flour, milled corn endosperm, sorghum flour, soybean flour, wheat flour, biomass derived starch, barley flour, and combinations thereof.

In some aspects, the fermentation media includes a treated starch. For example, the fermentation media can include a partially hydrolyzed starch. Partially hydrolyzed starch includes preparations having minimal hydrolysis (e.g., a DE of 5, having little dextrose) to preparations having substantial hydrolysis (e.g., a DE of 95, predominantly dextrose). In some preparations, the partially hydrolyzed starch can include high molecular weight dextrins and high molecular weight maltodextrins. In some modes of practice, a partially hydrolyzed starch product having a dextrose equivalent ("DE") in the range of about 5 to about 95 or more, or in some embodiments about 45 to about 65, is used in the fermentation media. Other DE ranges for partially hydrolyzed starch include 5-25, 15-35, 25-45, 35-55, 55-75, 65-85, and 75-95.

Partially hydrolyzed starches and preparation thereof are well known in the art. Partially hydrolyzed starches can be prepared by heating the starch with an acid such as hydrochloric or sulfuric acid at a high temperature and then neutralizing the hydrolysis mixture with a suitable base such as sodium carbonate. Alternatively, partially hydrolyzed starches can be prepared by an enzymatic process, such as by adding alpha-amylase to a starch preparation. An alpha amylase can cause the endohydrolysis of (1→4)-alpha-D-glucosidic linkages in polysaccharides containing three or more (1→4)-alpha-linked D-glucose units. For example, a partially hydrolyzed corn starch by enzymatic treatment is a liquefied corn starch that has been taken through liquefaction and treated with an alpha amylase. A partially hydrolyzed starch product can be used that have amounts of starch and starch degradation products within desired ranges.

In aspects of the disclosure, given production and secretion of the glucoamylase from the engineered yeast into the fermentation medium, the fermentation method may omit addition of purified or enriched commercial glucoamylase into the medium, or at least allow significantly less commercial glucoamylase to be used in a fermentation method. For example, the engineered yeast of the disclosure can allow addition of commercial glucoamylase to be eliminated or at least reduced by about 50%, 60%, 70%, 80%, 90%, or 95%. Typically amounts of glucoamylase in the range of about 7 units to about 50 units per liter would be used in fermentation methods that do not use a glucoamylase-secreting engineered yeast.

A corn wet milling process can be used to provide steep-water, which can be used for fermentation. Corn kernels can be steeped and then milled, and separated into their major constituent fractions. Light steep water is a byproduct of the steeping process, and contains a mixture of soluble proteins, amino acids, organic acids, carbohydrates, vitamins, and minerals.

The fermentation broth includes water and preferably includes nutrients, such as a nitrogen source (such as proteins), vitamins and salts. A buffering agent can also be present in the fermentation media. Other components may also be present in the fermentation broth after a period of fermentation, such as fermentation products which can accumulate as the fermentation progresses, and other metabolites. Optionally, the fermentation broth can be buffered with a base such as calcium hydroxide or calcium carbonate, ammonia or ammonium hydroxide, sodium hydroxide, or potassium hydroxide in order to maintain a pH at which the organism functions well.

The engineered yeast of the current disclosure can also be described in terms of the engineered yeast's growth rate. The growth rate of yeast can be defined by L=log(numbers) where numbers is the number of yeast cells formed per unit volume (mL), versus T (time).

The fermentation is carried out under conditions so that fermentation can occur. Although conditions can vary depending on the particular organism and desired fermentation product, typical conditions include a temperature of about 20° C. or greater, and more typically in the range of about 30° C. to about 50° C. During fermentation the reaction mixture can be mixed or agitated. In some modes of practice, the mixing or agitation can occur by the mechanical action of sparging gas to the fermentation broth. Alternatively direct mechanical agitation such as by an impellor or by other means can be used during fermentation.

The engineered yeast can be one that has an increased tolerance to growth at temperatures that greater than those in which yeast, such *Saccharomyces cerevisiae*, typically grow at. For example, *S. cerevisiae* typically have optimal growth in the temperature range of 30° C.-33° C. In some aspects, the engineered yeast of the disclosure display improved tolerance to growth at temperatures in the range of 34° C.-40° C.

For example, as compared to reference yeast without the genetic modification, the engineered yeast of the disclosure can have a rate of growth at a temperature in the range of 34° C.-40° C., that is 10%, 20%, 30%, 40%, or 50% greater than the growth rate of a reference yeast without the genetic modification.

In some cases fermentation is carried out in industrial capacity fermenters in order to achieve commercial scale economic benefits and control. In an aspect, the fermentation is carried out in a fermenter that has a capacity of about 10,000 liters or more.

The pH of the fermentation media can be adjusted to provide optimal conditions for glucoamylase activity, cell growth, and fermentation activity to provide a desired product, such as ethanol. For example, pH of the solution can be adjusted to in the range of 3 to 5.5. In one mode of practice, the pH of the fermentation media is in the range of 4 to 4.5.

As noted above, the present fermentation process using genetically modified microorganisms expressing the glucoamylase genes and capable of secreting the enzyme produced into the fermentation media. These enzymes are therefore directly exposed to the broth conditions and affect the carbohydrate composition in the fermentation media. In the fermentation media the glucoamylase can cause hydrolysis and release of D-glucose from the non-reducing ends of the starch or related oligo- and polysaccharide molecules by cleaving alpha-(1,4) and alpha-(1,6) glucosidic bonds.

Starch may also be acted on by one or more other amylases (e.g., alpha-amylase) present in the fermentation media. For example, if alpha-amylase is present in the fermentation media it can cause partial hydrolysis of precursor starch and cause a partial breakdown of the starch molecules by hydrolyzing internal alpha-(1,4)-linkages.

In some modes of practice, the fermentation is carried out as a single batch until completion.

In other modes of practice, the fermentation is carried out as a fed batch fermentation process. In this mode of practice, a first portion of a total amount of starch material to be fermented is added to the fermentation media wherein the glucoamylase enzyme acts on the starch to cause formation of glucose to be used as a substrate for fermentation. Additional starch material is added in one or more portions to provide more substrate for the glucoamylase enzyme in the media. The addition of starch can be regulated and the formation of glucose can be monitored to provide efficient fermentation.

Preferably, the fermentation is carried out in a continuous mode of operation. In this mode, multiple fermenters operate in series in which a starch hydrolysate is supplied in the first fermenter, which is fed to second fermenter and so on until the starch hydrolysate is converted to ethanol. Continuous operation can be operated using between 2-7 fermenters.

In modes of fermenting, a liquid medium including partially hydrolyzed starch can be added "throughout" the fermentation period, meaning that the partially hydrolyzed starch is added more than once during the period. This can be accomplished by the addition of a plurality of batches of liquid medium added periodically to the fermentation medium throughout the period, by continuous addition of liquid medium including the partially hydrolyzed starch throughout the period, or combinations thereof.

In some modes of practice, a portion of the total amount of starch material is added to the fermentation broth using a variable rate addition system. Examples of such systems include a variable speed pump or a metering valve (such as a throttle valve) operably connected to a pump, which pump or valve can be utilized to vary the amount of starch material introduced into the fermentation broth over time. In some modes of practice, during the addition of a portion of the starch material, glucose concentration is monitored by a real-time monitoring system.

Real-time monitoring systems include systems that directly monitor glucose concentration and systems that indirectly monitor glucose concentration. Examples of real-time monitoring systems that typically directly monitor glucose concentration include systems based on infrared (IR) spectroscopy, near-infrared (NIR) spectroscopy systems, Fourier transform infrared (FTIR) systems, systems based on refractive index, automated enzyme based measurement systems such as a YSI 2950 Biochemistry Analyzer sold by YSI Life Sciences systems, high performance liquid chromatography (HPLC) based systems, gas chromatography (GC) based systems, and other real-time monitoring systems known to one of skill in the art. Additionally real-time monitoring systems that indirectly monitor/measure the glucose concentration of a fermentation process can be developed by determining the typical carbon distribution in a particular fermentation process and correlating the glucose concentration present in the fermentation broth to another parameter exhibited by the fermentation, such as, for example, a correlation of the glucose level present in the fermentation broth with a measurement of the carbon dioxide evolution rate and the amount of carbon dioxide present in an off-gas stream from the fermentation vessel. The carbon dioxide can be readily measured through use of a mass spectrometer or other suitable instrumental technique for measuring the components of the off-gas stream. In a preferred aspect, the glucose concentration is monitored by a real-time monitoring system using infrared spectroscopy. In another one aspect, the glucose concentration is monitored by a real-time monitoring system using near-infrared spectroscopy. The real time monitoring systems interface with equipment that controls the introduction of starch material into the fermentation broth to modulate the formation of glucose to a desired concentration in the fermentation broth.

During the fermentation process a sample of the fermentation medium can be taken to determine the amount of glucoamylase activity in the medium. The amount of glucoamylase activity in the medium can be referred to as extracellular glucoamylase activity as it corresponds to glucoamylase secreted from the engineered yeast. In some modes of measuring, the amount of glucoamylase activity in the medium can be determined by the amount of glucoamylase activity per amount of biomass per volume of medium.

As used herein "biomass" refers to the weight of the engineered yeast, which can be measured in grams of dried cell weight per liter of medium (DCW/L).

A unit (U) of GA activity can be defined as the amount of enzyme that catalyzes the release of 1 mg glucose/min from starch. Glucoamylase activity can be measured in concentrated broth by coupling starch hydrolysis to a HXK/G6PDH reaction mix (Sigma G3293) in a two-step end point assay. Broth can be concentrated from a predetermined amount of cells grown using a non-glucose carbon source (i.e. raffinose) to avoid interference with the assay.

The specific activity is equal to the activity in a given volume of broth divided by the wet weight of cells in the same volume of broth. Specific activity has the following units, U of GA activity per gram of biomass (U/g biomass). The amount of biomass used in the assay can be measured by determining the wet cell weight after removing the broth, either by filtration or centrifugation.

A starch solution is prepared by dissolving 1.1 g of corn starch (S4126, Sigma) in 50 mL of near boiling water, then adding 1 mL of 3M sodium acetate pH 5.2. A volume of concentrated broth ($V_b$), typically in the range of 1-20 ul (prepared by using a 10 Kd cutoff column, Millipore #UFC901008) is added to the starch slurry ($V_s$), in a total volume of 200 ul, and allowed to incubate at 37° C. for a specific period of time (T), typically between 5-60 minutes. Parameters are selected such that the glucose formation is linear within a desired time. 20 μL of each sample is added to 2 μL, 0.6N NaOH and mixed well. 200 μL of the HXK/G6PDH mix is then added and incubated at 30° C. for 30 minutes. The absorbance at 340 nm is measured using a spectrophotometer (SpectraMax™ M2). Regression analysis using known glucose standards is used to calculate the amount of glucose released in each sample. The specific enzyme activity per gram of biomass (U/g biomass) can be calculated by obtaining the weight in grams of the sample used prior to concentration. Unit of activity=(mg glucose/T)*(($V_b$+$V_s$)/($V_b$))*(222/20). Specific activity=Unit of activity/g biomass.

In other aspects, an amount of glucoamylase activity in a fermentation medium provided by an engineered yeast of the disclosure can be described relative to a reference yeast. For example, the amount of glucoamylase activity that an engineered yeast expressing heterologous glucoamylase (e.g., having 90% or greater identity to identical to SEQ ID NO:11) encoded by multiple exogenous nucleic acids, can be compared to an otherwise identical yeast without the exogenous nucleic acids.

Measurement of glucoamylase activity in the fermentation medium can be performed at a desired time point during fermentation. For example, a sample from the fermentation media can be taken about $^1/_{10}$, about $^2/_{10}$, about $^3/_{10}$, about $^4/_{10}$, about $^5/_{10}$, about $^6/_{10}$, about $^7/_{10}$, about $^8/_{10}$, about $^9/_{10}$ of the way through the fermentation process, or at the end of the fermentation process, and the sample can be tested for glucoamylase activity.

In some modes of practice, the fermentation period is about 30 hours or greater, about 40 hours or greater, about 50 hours or greater, or about 60 hours or greater, such as a period of time in the range of about 40 to about 160 hours, 50 to about 150 hours, about 60 to about 140 hours, about 60 to about 120 hours, or about 60 to about 120 hours. In modes of practice the fermentation period is for about 5 or about 6 days.

The fermentation product (also referred to herein as a "bio-derived product" or "bioproduct") can be any product that can be prepared by enzymatic degradation of a starch material by the glucoamylase, formation of glucose, and fermentation of glucose. In an aspect, the fermentation product is selected from the group consisting of: amino acids, organic acids, alcohols, diols, polyols, fatty acids, fatty acid alkyl esters (such as fatty acid methyl or ethyl esters (for example C6 to C12 fatty acid methyl esters (preferably C8 to C10 fatty acid methyl esters))), monoacyl glycerides, diacyl glycerides, triacyl glycerides, and mixtures thereof. Preferred fermentation products are organic acids, amino acids, fatty acid alkyl esters (such as fatty acid methyl esters (for example C8 to C12 fatty acid methyl esters (preferably C8 to C10 fatty acid methyl esters))), and their salts thereof, and especially where the organic acid is selected from the group consisting of hydroxyl carboxylic acids (including mono-hydroxy and di-hydroxy mono-, di-, and tri-carboxylic acids), monocarboxylic acids, dicarboxylic acids, and tricarboxylic acids and mixtures thereof. Examples of fermentation products that are prepared by the present process are organic acids or amino acids such as lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, acetic acid, methyl hexanoate, methyl octanoate, methyl nonanoate, methyl decanoate, methyl dodecanoate, ethyl hexanoate, ethyl octanoate, ethyl nonanoate, ethyl decanoate, ethyl dodecanoate, and mixtures thereof and derivatives thereof and salts thereof. In a preferred aspect, a fermentation method of the disclosure produces ethanol as the bioproduct.

In some modes of practice, the fermentation product can be recovered from the fermentation broth. The manner of accomplishing this will depend on the particular product. However, in some modes of practice, the organism is separated from the liquid phase, typically via a filtration step or centrifugation step, and the product recovered via, for example, distillation, extraction, crystallization, membrane separation, osmosis, reverse osmosis, or other suitable technique.

The present process provides the ability to make fermentation products on a production scale level with excellent yields and purity. In an aspect, the process is carried out in fermentation broth quantities of at least 25,000 gallons. In an aspect, the batch process is carried out in to produce batches of at least 25,000 gallons of final fermentation broth. Add continuous process, vessels of at least 200,000 gallons A composition comprising the secreted glucoamylase can optionally be used in combination with any one or in any combination with the following enzymes that are different than the glucoamylase. Exemplary other enzymes include alpha amylases, beta-amylases, peptidases (proteases, proteinases, endopeptidases, exopeptidases), pullulanases, isoamylases, cellulases, hemicellulases, endo-glucanases and related beta-glucan hydrolytic accessory enzymes, xylanases and xylanase accessory enzymes, acetolactate decarboxylases, cyclodextrin glycotransferases, lipases, phytases, laccases, oxidases, esterases, cutinases, granular starch hydrolyzing enzymes and other glucoamylases.

In some aspects, the glucoamylase produced by the recombinant cell can be used for starch conversion processes, such as for the production of dextrose for fructose syrups, specialty sugars and in alcohol and other end-product (e.g., organic acid, ascorbic acid, and amino acids). Production of alcohol from the fermentation of starch substrates using glucoamylases of the disclosure can include the production of fuel alcohol or potable alcohol.

The production of alcohol can be greater when a *Saccharomyces* species having at least four exogenous nucleic acids, each having a different nucleic acid sequence but that encode the same or a similar glucoamylase polypeptide, are used under the same conditions as compared to the parent strain. For example, the increase in alcohol production using the engineered *Saccharomyces* of the disclosure can be 1.1× or greater, 1.2× or greater, 1.3× or greater, 1.4× or greater, 1.5× or greater, 1.6× or greater, 1.7× or greater, 1.7× or greater, 1.8× or greater, 1.9× or greater, 2.0× or greater, 2.1× or greater, 2.2× or greater, 2.3× or greater, 2.4× or greater, or 2.5× or greater that alcohol production in a wild type strain.

In some aspects, the disclosure provides a method for producing ethanol by fermentation, wherein the ethanol is present in the fermentation media at a concentration of 90 g/L or greater. In the method, a liquid media comprising a starch material and an engineered yeast, such as an engineered *Saccharomyces* species having at least four exogenous nucleic acids, each having a different nucleic acid sequence but that encode the same or a similar glucoamylase polypeptide is fermented. Fermentation can provide an ethanol concentration of about 90 g/L or greater in the liquid media, such as in the range of about 90 g/L to about 170 g/L, in the range of about 110 g/L to about 170 g/L, in the range of about 125 g/L to about 170 g/L, in the range of about 130 g/L to about 170 g/L, or in the range of about 140 g/L to about 170 g/L.

In some aspects, the fermentation method uses an engineered yeast with at least one genetic modification providing a heterologous glucoamylase, and throughout the fermentation period, a liquid medium comprising partially hydrolyzed starch is added to the fermentation medium. The heterologous glucoamylase is secreted into the medium, and the genetic modification stable over the fermentation period to provide ethanol at a concentration of 130 g/L or greater in the fermentation medium at a fermentation period of five days or greater.

Strains of the disclosure can also be used in a fermentation process which provides lower amounts of glycerol production as compared to a wild type strain. Glycerol is a significant by-product during anaerobic production of ethanol and minimizing glycerol production is desirable as less sugar feedstock would be diverted from production of desired bioproducts such as ethanol. Surprisingly, strains of the disclosure demonstrate a considerable reduction of glycerol during a fermentation process. For example, in a fermentation process, the strains may produce less than 10 g/L of glycerol, less than about 9 g/L of glycerol, less than about 8 g/L of glycerol, or less than about 7 g/L of glycerol. Glycerol production using an organism of the disclosure can also be expressed relative to one or more bioproducts, such as ethanol, during a fermentation process. For example, in some modes of practice, during a fermentation process the ethanol to glycerol ratio is greater than about 13:1, or greater than about 14:1, such as in the range of about 14:1 to about 25:1.

The method includes fermenting a liquid media comprising a starch material and a engineered yeast comprising a exogenous nucleic acid encoding polypeptide comprising a glucoamylase portion and a signal sequence heterologous to the glucoamylase, wherein said fermentation provides an ethanol concentration of 90 g/L or greater in the liquid media.

The fermentation product may be first treated with one or more agents a treatment system. The treated fermentation product can then be sent to a distillation system. In the distillation system, the fermentation product can be distilled and dehydrated into ethanol. In some aspects, the components removed from the fermentation media include water, soluble components, oil and unfermented solids. Some of these components can be used for other purposed, such as for an animal feed product. Other co-products, for example, syrup can be recovered from the stillage.

Backset is the remaining fermentation broth following the removal of a bioproduct, such as alcohol, during the distillation process. Scrubber water is the liquid collected from a scrubber. Definitions of common terms of the disclosure can be found in *The Alcohol Textbook*, $4^{th}$ Edition. 1995.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a composition as described herein. In another aspect, the invention also relates to a kit comprising a glucoamylase of the current disclosure, or a composition as contemplated herein; and instructions for use of said glucoamylase or composition. The invention also relates to a fermented beverage produced by a method using the glucoamylase.

After the fermentation process is complete, materials present in the fermentation medium can be of use. In some aspects, after a fermentation process has been completed, or while a fermentation process is ongoing, some or all of a bioproduct can be removed from the fermentation medium to provide a refined composition comprising non-bioproduct solids. The non-bioproduct solids contain the engineered yeast, feedstock material in the medium that is not utilized by the yeast, as well as fermentation co-products. These materials can provide sources of carbohydrates and proteins that are useful as supplements to improve the nutritional content of a feed composition. The feed material can be a co-product from a fermentation process such as stillage (whole stillage, thin stillage, etc.) or composition prepared therefrom including dried distillers grains (DDG), distillers dry grains with solubles (DDGS), distillers wet grains (DWG), and distillers solubles (DS).

A fermentation medium, optionally with some or all of the target bioproduct removed, can be further treated, such as to remove water, or to cause precipitation or isolation of the non-bioproduct solids from the medium. In some cases the medium is treated by freeze drying or oven drying. After treatment the refined composition may be in the form of, for example, a liquid concentrate, a semi-wet cake, or a dry solid. The refined composition can be used as a feed composition itself, or an ingredient in the preparation of a feed composition. In preferred preparations, the feed composition is a livestock feed composition such as for sheep, cattle, pigs, etc.

The solids in the fermentation medium can provide a source of one or more amino acids. Introduced into an animal feed, the fermentation co-product can provide an enhanced amino acid content with regard to one or more essential amino acids. Essential amino acids can include histidine, isoleucine, lysine, methionine, phenylalanine, threonine, and tryptophan. These amino acids can be present in the feed composition as free amino acids or can be derived from proteins or peptides rich in the amino acids. The solids in the fermentation medium can provide a source of one prebiotics, which are nondigestible food substances, such as nondigestible oligosaccharides, that selectively stimulate the growth of favorable species of bacteria in the gut, thereby benefiting the host. The solids in the fermentation medium can provide a source of phytases, β-glucanases, proteases, and xylanases.

The feed composition can be used in aquaculture, is the farming of aquatic organisms such as fish, shellfish, or plants. Aquaculture includes the cultivation of both marine and freshwater species and can range from land-based to open-ocean production.

A feed composition, in addition to material obtained from the fermentation media, can include one or more feed additives. Feed additives can be used, for example, to help provide a balanced diet (e.g., vitamins and/or trace minerals), to protect the animals from disease and/or stress (e.g., antibiotics, probiotics) and/or to stimulate or control growth and behavior (e.g., hormones). Additive product ingredients may include, for example: growth promoters, medicinal substances, buffers, antioxidants, enzymes, preservatives, pellet-binding agents, direct-fed microbials, etc. Additive product ingredients may also include, for example, ionophores (e.g. monesin, lasalocid, laidlomycin, etc.), β-agonist (zilpaterol, ractompamine, etc.), antibiotics (e.g., chlortetracycline (CTC), oxytetracycline, bacitrain, tylosin, aureomycin), probiotics and yeast cultures, coccidiostats (e.g., amprollium, decoquinate, lasalocid, monensin), and hormones (e.g., growth hormones or hormones that inhibit estrus and/or ovulation such as melengestrol acetate), pheromones, nutraceuticals, pharmaceuticals, flavanoids, nutritive and non-nutritive supplements, detoxicants, etc. Some commercially available additives are sold under the trade names Rumensin®, Bovatec®, Deccox®, Tylan®, Optaflexx®, and MGA®.

Example 1

Generation of Amylolytic *Saccharomyces cerevisiae* Strains

Strain 1-3: Ura3Δ *Saccharomyces cerevisiae* Base Strain

Strain 1 (Ethanol Red™) was transformed with SEQ ID NO:1. SEQ ID NO:1 contains the following elements: i) an expression cassette for a mutant version of a 3-deoxy-D-arabino-heptulosonate-7-phosphate (DAHP) synthase gene from *Saccharomyces cerevisiae* (ARO4-OFP); and ii) flanking DNA for targeted chromosomal integration into the URA3 locus. Transformants were selected on synthetic complete media containing 3.5 g/L of p-fluorophenylalanine, and 1 g/L L-tyrosine (ScD-PFP). Resulting transformants were streaked for single colony isolation on ScD-PFP. A single colony was selected. Correct integration of SEQ ID NO: 1 into one allele of URA3 was verified by PCR in the single colony. A PCR verified isolate was designated Strain 1-1.

Stain 1-1 was transformed with SEQ ID NO:2. SEQ ID NO:2 contains the following elements: i) an expression cassette for a acetamidase (amdS) gene from *Aspergillus nidulans*; and ii) flanking DNA for targeted chromosomal integration into the URA3 locus. Transformants were selected on Yeast Nitrogen Base (without ammonium sulfate or amino acids) containing 80 mg/L uracil and 1 g/L acetamide as the sole nitrogen source. Resulting transformants were streaked for single colony isolation on Yeast Nitrogen Base (without ammonium sulfate or amino acids) containing 80 mg/L uracil and 1 g/L acetamide as the sole nitrogen source. A single colony was selected. Correct integration of SEQ ID NO 2 into the second allele of locus A was verified by PCR in the single colony. A PCR verified isolate is designated Strain 1-2.

Strain 1-2 was co-transformed with SEQ ID NO:3 and SEQ ID NO:4. SEQ ID NO:3 contains the following elements: i) an open reading frame for a cre recombinase from P1 bacteriophage, and ii) flanking DNA homologous to SEQ ID NO:4. SEQ ID NO:4 contains the following elements: i) a 2µ origin of replication; ii) a URA3 selectable marker from *Saccharomyces cerevisiae*; and iii) flanking DNA containing a PGK promoter and CYC1 terminator from *Saccharomyces cerevisiae*. Transformants were selected on synthetic drop-out media lacking uracil (ScD-Ura). Resulting transformants were streaked for single colony isolation on ScD-Ura. A single colony was selected. The isolated colony was screened for lack of growth on ScD-PFP and Yeast Nitrogen Base (without ammonium sulfate or amino acids) containing 80 mg/L uracil and 1 g/L acetamide as the sole nitrogen source. Loss of the ARO4-OFP and amdS genes was verified by PCR. The PCR verified isolate was streaked to YNB containing 5-FOA to select for loss of the 2µ plasmid. The PCR verified isolate was designated Strain 1-3.

Strain 1-4: *Saccharomyces cerevisiae* Expressing Two Codon Optimized Variants of the *Saccharomycopsis fibuligera* Glucoamylase at One Allele of CYB2

Strain 1-3 was co-transformed with SEQ ID NO:16 and SEQ ID NO:17. SEQ ID NO:16 contains the following elements: i) DNA homologous to the 5' region of the native CYB2 gene; and ii) an expression cassette for a unique codon optimized variant of the *Saccharomycopsis fibuligera* glucoamylase, under control of the TDH3 promoter and CYC1 terminator; and iii) the URA3 promoter as well as a portion of the URA3 gene. SEQ ID NO: 17 contains the following elements: i) a portion of the URA3 gene and terminator; and ii) an expression cassette for a unique codon optimized variant of the *Saccharomycopsis fibuligera* glucoamylase, under control of the PGK promoter and RPL3 terminator; and iii) DNA homologous to the 3' region of the native CYB2 gene. Transformants were selected on ScD-Ura. Resulting transformants were streaked for single colony isolation on ScD-Ura. A single colony was selected. Correct integration of SEQ ID NO:16 and SEQ ID NO:17 at one allele of CYB2 was verified by PCR. The PCR verified isolate was designated Strain 1-4.

Strain 1-5: *Saccharomyces cerevisiae* Expressing Four Codon Optimized Variants of the *Saccharomycopsis fibuligera* Glucoamylase at Both Alleles of CYB2

Strain 1-4 was co-transformed with SEQ ID NO:18 and SEQ ID NO:19. SEQ ID NO:18 contains the following elements: i) DNA homologous to the 5' region of the native CYB2 gene; and ii) an expression cassette for a unique codon optimized variant of the *Saccharomycopsis fibuligera* glucoamylase, under control of the TDH3 promoter and CYC1 terminator; and iii) the TEF1 promoter and a portion of the *Aspergillus nidulans* acetamidase gene (amdS). SEQ ID NO:19 contains the following elements: i) a portion of the *Aspergillus nidulans* acetamidase gene (amdS) and ADH1 terminator; and ii) an expression cassette for a unique codon optimized variant of the *Saccharomycopsis fibuligera* glucoamylase, under control of the PGK promoter and RPL3 terminator; and iii) DNA homologous to the 3' region of the native CYB2 gene. Transformants were selected on Yeast Nitrogen Base (without ammonium sulfate or amino acids) containing 80 mg/L uracil and 1 g/L acetamide as the sole nitrogen source. Resulting transformants were streaked for single colony isolation on Yeast Nitrogen Base (without ammonium sulfate or amino acids) containing 80 mg/L uracil and 1 g/L acetamide as the sole nitrogen source. A single colony was selected. Correct integration of SEQ ID NO:18 and SEQ ID NO:19 at the remaining allele of CYB2 was verified by PCR. The PCR verified isolate was designated Strain 1-5. FIG. 1 is a schematic diagram of the engineered CYB2 loci showing arrangement of the codon optimized GA variants and marker genes.

Strain 1-6: Recycling the URA3 and amdS Markers Via Cre Recombinase in Strain 1-5

Strain 1-5 was transformed with SEQ ID NO:9. SEQ ID NO:9 contains the following elements: i) an expression cassette for a mutant version of a 3-deoxy-D-arabino-heptulosonate-7-phosphate (DAHP) synthase gene from *Saccharomyces cerevisiae* (ARO4-OFP); 2) an expression cassette for a cre recombinase from P1 bacteriophage; 3) an expression cassette containing the native URA3, and 4) the *Saccharomyces cerevisiae* CEN6 centromere. Transformants were selected on synthetic complete media containing 3.5 g/L of p-fluorophenylalanine, and 1 g/L L-tyrosine (ScD-PFP). Resulting transformants were streaked for single colony isolation on ScD-PFP. A single colony was selected. The PCR verified isolate was designated Strain 1-6.

Strain 1-7: Restoring the Native URA3 at the Original Locus in Strain 1-6

Strain 1-6 was transformed with SEQ ID NO:10. SEQ ID NO:10 contains the follow elements: 1) an expression cassette for the native URA3, with 5' and 3' homology to the disrupted URA3 locus in Strain 1-6. Transformants were selected on ScD-ura. Resulting transformants were streaked for single colony isolate on ScD-ura. A single colony was selected. The PCR verified isolate was designated Strain 1-7.

Example 2

Evaluation of Amylolytic *Saccharomyces cerevisiae* Strains Containing Multiple Copies of Unique Codon Optimized Variants of the *Saccharomycopsis fibuligera* Glucoamylase in Simultaneous Saccharification and Fermentation Shake Flask Assays Shake Flask Evaluation Using Partially Hydrolyzed Corn Starch Strain 1-5 and Strain 1 are struck out on a ScD-Ura plate and incubated at 30° C. until single colonies are visible (1-2 days). Cells from the ScD-Ura plate are scraped into 10 mL of sterile water and the optical density ($OD_{600}$) is measured. Optical density is measured at wavelength of 600 nm with a 1 cm path length using a model Genesys20 spectrophotometer (Thermo Scientific).

A shake flask is inoculated with the cell slurry to reach an initial $OD_{600}$ of 0.1-0.3. Immediately prior to inoculating, 50 mL of shake flask medium is added to a 250 mL non-baffled shake flask (Corning 4995-250) fitted with a screw cap containing a gas-permeable seal (corning 1395-45LTMC) The shake flask medium consists of 850 g partially hydrolyzed corn starch, 150 g filtered light steep water, 25 g glucose, and 1 g urea. In a flask that contains Strain 1, 17.5 µl of Dupont Distillase glucoamylase is added immediately after inoculation (approximately 1.7 g enzyme per kilogram of starch).

The inoculated flask is incubated at 30° C. with shaking in an orbital shake at 100 rpm for 67 hours. Samples are taken and analyzed for ethanol concentrations in the broth during fermentation by high performance liquid chromatography with refractive index detector.

Figure 2:
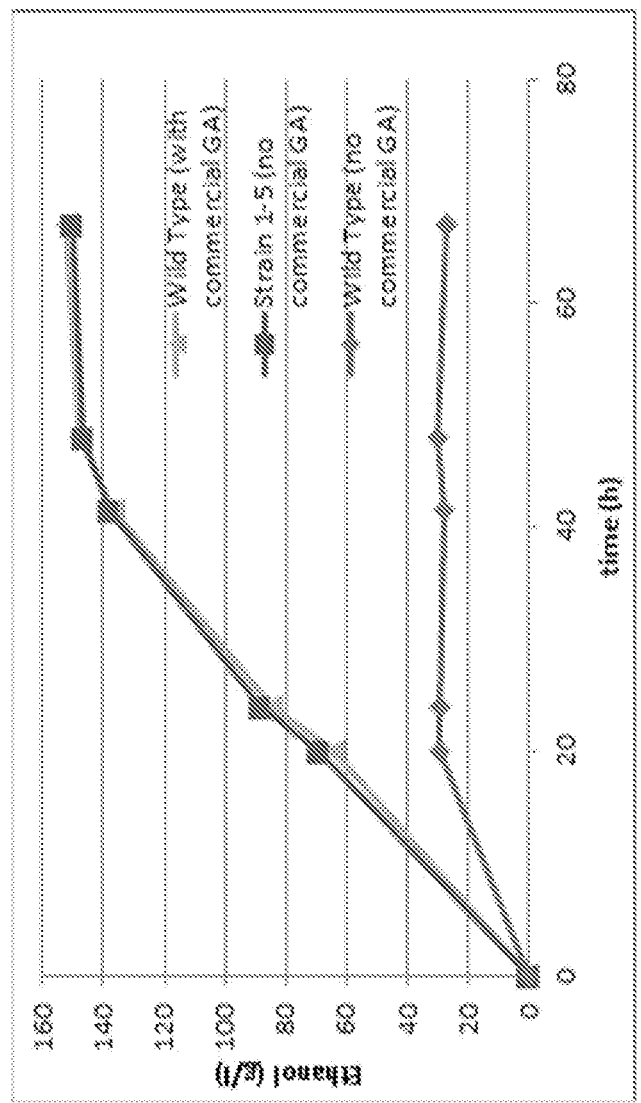
FIG. 2 is graph showing ethanol production from an ethanol tolerant strain having four unique codon optimized nucleic acids sequences encoding Sf GA, as compared to a (non-engineered) parent strain with and without commercial glucoamylase added to the fermentation media.

The results of the shake flask assay, shown in FIG. 2, demonstrate the effectiveness of strain 1-5 having the four unique codon optimized variants of *Saccharomycopsis fibuligera* glucoamylase for providing high ethanol titers, as compared to Strain 1 (i.e., without genetic modifications) without addition of commercial glucoamylase to the medium, and to the Strain 1 with addition of commercial glucoamylase to the medium.

Example 3

Evaluation of URA3 Restored Amylolytic *Saccharomyces cerevisaie* Strains Containing Multiple Copies of Unique Codon Optimized Variants of the *Saccharomycopsis fibuligera* Glucoamylase in Simultaneous Saccharification and Fermentation Shake Flask Assays Shake Flask Evaluation Using Partially Hydrolyzed Corn Starch Strain 1-5 and Strain 1-7 streaked out on a ScD-Ura plate and incubated at 30° C. until single colonies are visible (1-2 days). Cells from the ScD-Ura plate are scraped into 10 mL of sterile water and the optical density ($OD_{600}$) is measured. Optical density is measured at wavelength of 600 nm with a 1 cm path length using a model Genesys20 spectrophotometer (Thermo Scientific).

A shake flask is inoculated with the cell slurry to reach an initial $OD_{600}$ of 0.1-0.3. Immediately prior to inoculating, 50 mL of shake flask medium is added to a 250 mL non-baffled shake flask (Corning 4995-250) fitted with a screw cap containing a gas-permeable seal (corning 1395-45LTMC)

The shake flask medium consists of 850 g partially hydrolyzed corn starch, 150 g filtered light steep water, 25 g glucose, and 1 g urea.

The inoculated flask is incubated at 30° C. with shaking in an orbital shake at 100 rpm for 64 hours. Samples are taken and analyzed for ethanol concentrations in the broth during fermentation by high performance liquid chromatography with refractive index detector.

Figure 3:
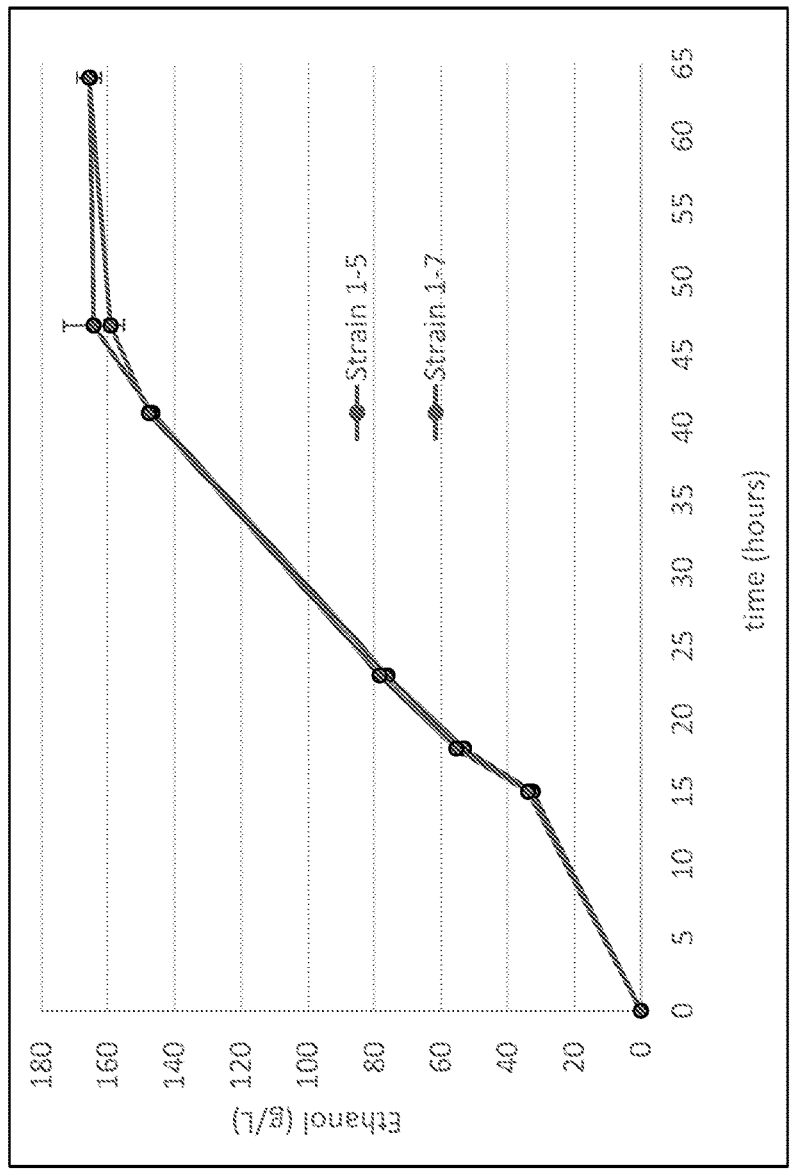
FIG. 3 is graph showing ethanol production of the ethanol tolerant strain having four unique codon optimized nucleic acids sequences encoding Sf GA, as compared to a strain with the same Sf GA sequences, but with URA3 restored at the native locus.

The results of the shake flask, shown in FIG. 3, demonstrate ethanol production profile for Strain 1-5, which contains four unique codon optimized variants of the *Saccharomycopsis fibuligera* glucoamylase with markers at the engineered CYB2 locus compared to Strain 1-7, which contains four unique codon optimized variants of the *Saccharomycopsis fibuligera* glucoamylase with URA3 restored at the native locus.

Example 4

Evaluation of Strain 1 and Strain 1-5 in a Continuous Simultaneous Saccharification and Fermentation System Continuous Saccharification and Fermentation The continuous simultaneous saccharification and fermentation system consisted of a saccharification tank and 4 fermentors run in series (New Brunswick BioFlo 310). The saccharification tank working volume is 2.1-2.3 liters and is held at 60° C., and continuously fed liquefied corn starch hydrolysate (34% dissolved solids, 3% glucose), dosed with glucoamylase (Dextrozyme 1.5×, Novozymes) to obtain the desired dextrose conversion in 7 hours (represented as percentage of starch converted to dextrose by weight). Approximately 60% of the flow from the saccharification tank was fed into the first fermentor (Ferm1), while 40% was directed into a second fermentor (Ferm2). Sterilized light steep water (sLSW, consisting of raw light steep water, backset, and scrubber water) was fed into Ferm1 to obtain a free amino nitrogen (FAN) target of ~600 ppm. Stillage and scrubber water were added as diluent to allow for the system FAN and dextrose targets to be achieved with the set flow rates and retention times. Ferm1 working volume was 2.2 liters, held at 30° C., with an agitation of 100 RPM, and a residence time of 6.7 hours. Ferm1 was supplied with air at a flow rate of 0.25 volume of air per volume of media (VVM), introduced through a ring sparger in the bottom of the fermentor. Ferm1 flowed to Ferm2. Ferm2 working volume was 3.9-4.1 liters, held at 30° C., with an agitation of 100 RPM and a residence time of 8.7-9.1 hours. Ferm2 flowed to fermentor 3 (Ferm3), which had a working volume of 5.4 liters held at 30° C., with an agitation of 100 RPM, and a residence time of 11.8 hours. Ferm3 flowed to fermentor4 (Ferm4), which had a working volume of 13.8 liters held at 30° C., with an agitation of 100 RPM, and a residence time of 30.5 hours.

Strain 1 or Strain 1-5 was grown overnight in a 250 ml erlenmeyer shake flask containing 50 mls of yeast mold (YM) broth, with agitation of 250 RPM and a temperature of 30° C. from a single colony on a PDA plate. To inoculate the continuous system using strain 1-5, broth from the overnight shake flask was added to Ferm1 to reach a starting $OD_{600}$ of 0.2, and operated as a batch (supplemented initially with 50 g/L glucose) until the carbon dioxide evolution rates (CER) reached the highest level and began trending downward, after which the flows were started to begin the continuous operation. To inoculate the continuous system using Strain 1, broth from the overnight shake flask was added to Ferm1 to reach a starting $OD_{600}$ of 0.2. Immediately after inoculation, commercial glucoamylase (Distillase SSF, Dupont) was added to Ferm1 at a rate of 0.5 g/Kg of starch (dry basis) and operated as a batch as described for Strain 1-5. For strain 1-5, no additional GA was added to the fermentation portion of the system. Once parameters had maintained set conditions, the system was allowed to continuously run for at least five days. Samples were collected twice a day for a minimum of five days and analyzed by HPLC (gram per liter) and cell dry weight. (CDW, gram per liter). The results of which are averaged and shown in the following tables.

The results of the fermentations, shown in Tables 4 through 6 demonstrate similar ethanol titers (EtOH), dextrose titers (Dx), and growth (CDW) for Strain 1-5 relative to Strain 1, yet Strain 1-5 produces less glycerol.

TABLE 4

Levels of relevant metabolites in each stage of continuous fermentation for Strain 1 (67% +/− 5% dextrose saccharification material)

|  | Ferm1 | Ferm2 | Ferm3 | Ferm4 |
|---|---|---|---|---|
| Dx (g/L) | 71.4 +/− 11.9 | 74.5 +/− 17.7 | 45.1 +/− 21.4 | 6.0 +/− 3.99 |
| EtOH (g/L) | 46.4 +/− 2.29 | 67.2 +/− 8.83 | 95.0 +/− 2.00 | 127.0 +/− 7.73 |
| Glycerol (g/L) | 6.1 +/− 0.56 | 7.3 +/− 0.74 | 8.8 +/− 0.59 | 10.2 +/− 0.47 |
| CDW (g/L) | 6.8 +/− 1.8 | 7.9 +/− 3.0 | 8.9 +/− 2.1 | 7.3 +/− 1.8 |

TABLE 5

Levels of relevant metabolites in each stage of continuous fermentation for Strain 1-5 (62% +/− 0.5% dextrose saccharification material)

|  | Ferm1 | Ferm2 | Ferm3 | Ferm4 |
|---|---|---|---|---|
| Dx (g/L) | 77.2 +/− 3.00 | 97.3 +/− 2.61 | 65.9 +/− 2.62 | 21.0 +/− 1.91 |
| EtOH (g/L) | 47.3 +/− 1.00 | 67.3 +/− 0.81 | 100.3 +/− 0.81 | 131.8 +/− 1.08 |
| Glycerol (g/L) | 4.4 +/− 0.15 | 6.0 +/− 0.20 | 5.7 +/− 0.21 | 8.8 +/− 0.21 |
| CDW (g/L) | 9.0 +/− 1.8 | 8.9 +/− 0.7 | 9.0 +/− 0.7 | 7.8 +/− 1.0 |

TABLE 6

Levels of relevant metabolites in each stage of continuous fermentation for Strain 1-5 (45% +/− 2% dextrose saccharification material)

| | Ferm1 | Ferm2 | Ferm3 | Ferm4 |
|---|---|---|---|---|
| Dx (g/L) | 28.9 +/− 2.17 | 54.1 +/− 3.61 | 38.1 +/− 4.45 | 5.1 +/− 2.57 |
| EtOH (g/L) | 50.1 +/− 1.73 | 69.4 +/− 3.01 | 101.4 +/− 3.39 | 132.2 +/− 1.30 |
| Glycerol (g/L) | 3.1 +/− 0.15 | 4.6 +/− 0.24 | 5.7 +/− 0.21 | 6.6 +/− 0.34 |
| CDW (g/L) | 9.2 +/− 1.3 | 9.5 +/− 0.7 | 9.8 +/− 0.4 | 7.9 +/− 0.6 |

What is claimed is:

1. An engineered yeast comprising at least first, second, third, and fourth exogenous nucleic acids each comprising a sequence encoding a common glucoamylase polypeptide that is heterologous to the *Saccharomyces* species, or encoding two or more different glucoamylase polypeptides having 90% or greater sequence identity to each other, wherein the first, second, third, and fourth exogenous nucleic acids have nucleic acid sequences that are different from one another and wherein the first, second, third and fourth exogenous nucleic acid sequences are at least 90% identical to SEQ ID NO: 5, SEQ ID NO: 6, SEQ ID NO: 7 and SEQ ID NO: 8.

2. The engineered yeast of claim 1 wherein the glucoamylase polypeptide(s) is from a yeast or fungal organism selected from the group consisting of *Amorphotheca resinae*, *Aspergillus niger*, *Aspergillus awamori*, *Aspergillus oryzae*, *Aspergillus kawachii*, *Aspergillus shirousami*, *Blastobotrys adeninivorans*, *Candida albicans*, *Rhizopus oryzae*, *Schizosaccharomyces pombe*, and *Saccharomycopsis fibuligera*.

3. The engineered yeast of claim 1 wherein the glucoamylase polypeptide has 90% or greater sequence identify to SEQ ID NO:11 and optionally includes one or more amino acid substitutions are at one or more of the following amino acid positions in SEQ ID NO:11: 1M-5T, 7F, 9T, 10A, 15V, 16A, 18C, 19V, 21V, 22E, 24D, 27N-30H, 32Q, 36G, 38T, 40A, 42S-50E, 52P, 53A, 56W, 64D, 71K-74K, 77V, 79V, 86E, 90F, 97T, 103S-106A, 108V, 111H, 112S, 114S, 121V, 127S-129T, 131T, 135V, 141N, 144S, 145P, 148D, 157V, 159D, 160T, 164A, 165S, 187A, 189A-191H, 193N, 197L, 199A-203G, 205P, 206Y, 209A, 210S, 214W, 215K, 222Q, 223H, 225S-227H, 229S-231S, 242T, 247A, 251L, 255S, 257G-261S, 263T-265N, 267P, 268P, 270T-272W, 274E-270A, 281N, 284I-286S, 292S-295K, 300S, 302Q, 304S, 307G, 316A, 317A, 319I, 325D-329Y, 333N, 337S, 341N, 343L, 345Y, 348V, 352N, 355K, 356I, 358G, 359N, 361K, 366V, 377V, 379T, 386Q, 393, G, 395T, 396F, 398T, 402N-411V, 413E, 415L, 419L, 420Y, 422S, 423F, 425A, 429K, 431D, 433S, 435A, 437K, 440L, 442L-444Y, 448N-451N, 453I-455S, 457L, 458Q, 465K, 467L, 472D, 474N, 476Q, 478T, 480E, 481I, 487F-489A, 492V, 500S, 503S, 505N, 507A, 511L-513E, and 515L.

4. The engineered yeast of claim 1 wherein the glucoamylase polypeptide comprises a secretion signal amino acid sequence having 90% or greater identity to SEQ ID NO:12 or SEQ ID NO:13.

5. The engineered yeast of claim 4 wherein the glucoamylase polypeptide comprises a secretion signal amino acid sequence of SEQ ID NO:12 or SEQ ID NO:13.

6. The engineered yeast of claim 1 wherein the first, second, third, and fourth exogenous nucleic acids differ from each other by at least 10%.

7. The engineered yeast of claim 1 wherein the first nucleic acid comprises a nucleic acid having 95% or greater, 98% or greater, 99% or greater, or 100% identity to SEQ ID NO:5.

8. The engineered yeast of claim 1 wherein the second nucleic acid comprises a nucleic acid having 95% or greater, 98% or greater, 99% or greater, or 100% identity to SEQ ID NO:6.

9. The engineered yeast of claim 1 wherein the third nucleic acid comprises a nucleic acid having 95% or greater, 98% or greater, 99% or greater, or 100% identity to SEQ ID NO:7.

10. The engineered yeast of claim 1 wherein the fourth nucleic acid comprises a nucleic acid having 95% or greater, 98% or greater, 99% or greater, or 100% identity to SEQ ID NO:8.

11. The engineered yeast of claim 1 wherein the first and third nucleic acids are under the control of a first common promoter.

12. The engineered yeast of claim 11, wherein the first common promoter comprises a glyceraldehyde-3-phosphate dehydrogenase (TDH3) promoter nucleic acid sequence.

13. The engineered yeast of claim 1 wherein the second and fourth nucleic acids are under the control of a second common promoter.

14. The engineered yeast of claim 13 wherein the second common promoter comprises a phosphoglycerate kinase (PGK) promoter nucleic acid sequence.

15. The engineered yeast of claim 1 selected from the group consisting of *Saccharomyces cerevisiae, Isaatchenkia orientalis, Candida utilis, Pichia Stipitis, Yarrowia lipolytica, Kluyveromyces marxiannus*, and *Kluyeromyces lactis*.

16. An engineered yeast comprising first, second, third, and fourth exogenous nucleic acids each comprising a sequence encoding a polypeptide comprising SEQ ID NO:11, wherein the first nucleic acid comprises SEQ ID NO:5, the second nucleic acid comprises SEQ ID NO:6, the third nucleic acid comprises SEQ ID NO:7, and the fourth nucleic acid comprises SEQ ID NO:8.

17. The engineered yeast of claim 16 that produces less glycerol than a control strain that does not include the nucleic acids under the same fermentation conditions.

18. A method for producing a bioproduct comprising:
fermenting a liquid media comprising a starch material and the engineered yeast of claim 1, wherein said fermenting produces the bioproduct.

19. The method of claim 18 wherein the bioproduct is ethanol and fermenting provides at a concentration of 90 g/L or greater in the liquid media.

20. The method of claim 18 wherein the starch material is present in the liquid media at a concentration in the range of 30 to 37 wt % (dry solids) and the starch material has a dextrose equivalent in the range of 45 to 65.

* * * * *

UNITED STATES PATENT AND TRADEMARK OFFICE
CERTIFICATE OF CORRECTION

PATENT NO. : 10,344,288 B2  
APPLICATION NO. : 15/562266  
DATED : July 9, 2019  
INVENTOR(S) : Christopher K. Miller et al.

Page 1 of 1

It is certified that error appears in the above-identified patent and that said Letters Patent is hereby corrected as shown below:

In the Specification

In Column 9, Line 36, delete "fibukgera" and insert -- fibuligera --, therefor.

In Column 11, Line 38, delete "N611" and insert -- N61I --, therefor.

In Column 11, Line 43, delete "N611" and insert -- N61I --, therefor.

In Column 11, Line 47, delete "N611" and insert -- N61I --, therefor.

In Column 13, Line 34, delete "PHOS" and insert -- PHO5 --, therefor.

In Column 16, Line 13, delete "PHOS" and insert -- PHO5 --, therefor.

In Column 18, Line 43, delete "(HISS)," and insert -- (HIS3), --, therefor.

In Column 18, Line 43, delete "LIRAS)," and insert -- URA5), --, therefor.

In the Claims

In Column 89, Line 64, in Claim 3, delete "257G-2615," and insert -- 257G-261S, --, therefor.

In Column 89, Line 66, in Claim 3, delete "3191," and insert -- 319I, --, therefor.

In Column 89, Line 67, in Claim 3, delete "3561," and insert -- 356I, --, therefor.

In Column 90, Line 32, in Claim 3, delete "393, G," and insert -- 393G, --, therefor.

Signed and Sealed this  
Third Day of December, 2019

Andrei Iancu  
*Director of the United States Patent and Trademark Office*

SEQUENCE LISTING

<160> NUMBER OF SEQ ID NOS: 19

<210> SEQ ID NO 1
<211> LENGTH: 3182
<212> TYPE: DNA
<213> ORGANISM: Artificial Sequence
<220> FEATURE:
<223> OTHER INFORMATION: pAV18 transformation fragment

<400> SEQUENCE: 1

```
cctactgcgc caattgatga caatacagac gatgataaca aaccgaagtt atctgatgta      60
gaaaaggatt aaagatgcta agagatagtg atgatatttc ataaataatg taattctata     120
tatgttaatt acctttttg cgaggcatat ttatggtgaa ggataagttt tgaccatcaa      180
agaaggttaa tgtggctgtg gtttcagggt ccataaagct tttcaattca tcttttttt     240 ttttgttctt ttttttgatt ccggtttctt tgaaattttt ttgattcggt aatctccgag     300
cagaaggaag aacgaaggaa ggagcacaga cttagattgg tatatatacg catatgtggt     360
gttgaagaaa catgaaattg cccagtattc ttaacccaac tgcacagaac aaaaacctgc     420
aggaaacgaa gataaagcgg ccgcataact tcgtataatg tatgctatac gaagttatct     480
gccagtatac agctagcctt gaaagtgatg gaaaacattg tcatcggcac ataaataaaa     540
aaattatgaa tcacgtgatc aacagcaaat tatgtactcg tatatatgca agcgcattcc     600
ttatattgac actctttcat tgggcatgag gctgtgtaaa cataagctgt aacggtctca     660
cggaacactg tgtagttgca ttactgtcag gcagttatgt tgcttaatat aaaggcaaag     720
gcatggcaga atcactttaa aacgtggccc caccgctgc accctgtgca ttttgtacgt     780
tactgcgaaa tgactcaacg atgaaatgaa aaaattttgc ttgaaatttt gaaaaaaga     840 tgtgcgggac gcattgttag ctcattgaat acatcgtgat cgaatccaat caatgtttaa     900
tttcatatta atacagaaac ttttctcat actttcttct tcttttcatt ggtatattat     960
ctatatatcg tgttaattcc tctttcgtca tttttagcat cgttataaga gtaattaaga    1020
ataactagaa gagtctctct ttatattcgt ttatttata tatttaaccg ctaaatttag    1080
taaacaaaag aatctatcag aaatgagtga atctccaatg ttcgctgcca acggcatgcc    1140
aaaggtaaat caaggtgctg aagaagatgt cagaatttta ggttacgacc cattagcttc    1200
tccagctctc cttcaagtgc aaatcccagc cacaccaact tctttggaaa ctgccaagag    1260
aggtagaaga gaagctatag atattattac cggtaaagac gacagagttc ttgtcattgt    1320
cggtccttgt tccatccatg atctagaagc cgctcaagaa tacgctttga gattaaagaa    1380
attgtcagat gaattaaaag gtgatttatc catcattatg agagcatact ggagaagcc    1440 aagaacaacc gtcggctgga aggtctaat taatgaccct gatgttaaca acactttcaa    1500
catcaacaag ggtttgcaat ccgctagaca attgttgtc aacttgacaa atatcggttt    1560
```

```
gccaattggt tctgaaatgc ttgataccat ttctcctaaa tacttggctg atttggtctc   1620
cttcggtgcc attggtgcca gaaccaccga atctcaactg cacagagaat tggcctccgg   1680
tttgtctttc ccagttggtt tcaagaacgg taccgatggt accttaaatg ttgctgtgga   1740
tgcttgtcaa gccgctgctc attctcacca tttcatgggt gttactaagc atggtgttgc   1800
tgctatcacc actactaagg gtaacgaaca ctgcttcgtt attctaagag gtggtaaaaa   1860
gggtaccaac tacgacgcta agtccgttgc agaagctaag gctcaattgc ctgccggttc   1920
caacggtcta atgattgact actctcacgg taactccaat aaggatttca gaaaccaacc   1980
aaaggtcaat gacgttgttt gtgagcaaat cgctaacggt gaaaacgcca ttaccggtgt   2040
catgattgaa tcaaacatca cgaaggtaa  ccaaggcatc ccagccgaag gtaaagccgg   2100
cttgaaatat ggtgtttcca tcactgatgc ttgtataggt tgggaaacta ctgaagacgt   2160
cttgaggaaa ttggctgctg ctgtcagaca aagaagagaa gttaacaaga aatagatgtt   2220
tttttaatga tatatgtaac gtacattctt tcctctacca ctgccaattc ggtattattt   2280
aattgtgttt agcgctattt actaattaac tagaaactca attttaaag gcaaagctcg    2340 ctgacctttc actgatttcg tggatgttat actatcagtt actcttctgc aaaaaaaaat   2400
tgagtcatat cgtagctttg ggattatttt tctctctctc cacggctaat taggtgatca   2460
tgaaaaaatg aaaaattcat gagaaaagag tcagacatcg aaacatacat aagttgatat   2520
tcctttgata tcgacgacta ctcaatcagg ttttaaaaga aaagaggcag ctattgaagt   2580
agcagtatcc agtttaggtt ttttaattat ttacaagtaa agaaaaagag aatgccggtc   2640
gttcacgata acttcgtata atgtatgcta tacgaagtta tgcggccgcg agaagatgcg   2700
gccagcaaaa ctaaaaaact gtattataag taaatgcatg tatactaaac tcacaaatta   2760
gagcttcaat ttaattatat cagttattac ccgggaatct cggtcgtaat gatttctata   2820
atgacgaaaa aaaaaaaatt ggaagaaaa  agcttcatgg cctttataaa aaggaactat   2880
ccaatacctc gccagaacca agtaacagta ttttacgggg cacaaatcaa gaacaataag   2940
acaggactgt aaagatggac gcattgaact ccaaagaaca acaagagttc caaaaagtag   3000
tggaacaaaa gcaaatgaag gatttcatgc gtttgtactc taatctggta gaaagatgtt   3060
tcacagactg tgtcaatgac ttcacaacat caaagctaac caataaggaa caaacatgca   3120
tcatgaagtg ctcagaaaag ttcttgaagc atagcgaacg tgtagggcag cgtttccaag   3180
ag                                                                  3182

<210> SEQ ID NO 2
<211> LENGTH: 3275
<212> TYPE: DNA
<213> ORGANISM: Artificial Sequence
<220> FEATURE:
<223> OTHER INFORMATION: pCM520 transformation fragment

<400> SEQUENCE: 2
cctactgcgc caattgatga caatacagac gatgataaca aaccgaagtt atctgatgta     60
gaaaaggatt aaagatgcta agagatagtg atgatatttc ataaataatg taattctata    120
tatgttaatt acctttttg  cgaggcatat ttatggtgaa gaataagttt tgaccatcaa    180
agaaggttaa tgtggctgtg gtttcagggt ccataaagct tttcaattca tcatttttt    240 tttattcttt ttttgattc  cggtttcctt gaattttttt tgattcggta atctccgaac    300
agaaggaaga acgaaggaag gagcacagac ttagattggt atatatacgc atatgtagtg    360
ttgaagaaac atgaaattgc ccagtattct taacccaact gcacagaaca aaaatctgca    420
```

```
ggaaacgaag ataaagcggc cgcataactt cgtatagcat acattatacg aagttatcgc    480
ctgttaagat ataactgaaa aaagagggga attttagat actgaaatga tatttagaa      540 taaccagact atatataagg ataaattaca aaaaattaac taatagataa gatttaaata    600
taaaagatat gcaactagaa aagtcttatc aatctcctta tggagtgacg acgttaccca    660
acaatttacc gacttcttcg gcgatagcca aagttctctc ttcggacaat cttctaccaa    720
taacttgaac agcaacagga gcaccgtgat aagcctctgg gtcgtattct tcttgaacca    780
aagcatccaa ttcggaaaca gctttaaaag attcgttctt cttatcaata ttcttatcag    840
cgaaagtgac tgggacgaca acagaggtga atccaataa gttaataacg gaggcgtaac     900
cgtagtatct gaattgatcg tgtctgacag cggcggtagg agtaattgga gcgataatag    960
cgtccaattc cttaccagct ttttcttcag cttcacgcca cttttccaag tattccattt    1020
gatagttcca cttttgtaaa tgagtgtccc acaattcgtt catgttaaca gccttaatat    1080
ttgggttcaa caagtcctta atgttaggga tggctggctc accagaggca gaaatgtctc    1140
tcatgacgtc ggcagaacca tcagcagcat agatgtggga aatcaagtca tgaccgaaat    1200
catgcttgta tggagtccat ggagtaacgg tgtgaccagc cttggccaaa gcggcaacgg    1260
tagtttcgac accacgtaaa attggtgggt gtggcaagac gttaccgtcg aaattgtaat    1320
aaccaatgtt caaaccacca ttcttaatct tagaggcaat gatgtcagat tcagattgtc    1380
tccatggcat tgggatgacc ttagagtcgt acttccaagg ttcttgaccc aagacagatt    1440
tggtgaacaa tctcaagtct tcgacggagt gagtgatagg accaacgacg gagtgaacgg    1500
tttcttgacc ttccatagag ttagccattt tagcatatgg caatctaccg tgagatggtc    1560
tcaaaccgta taaaaagttg aaagcagctg ggactctaat ggaaccacca atgtcagtac    1620
cgacaccaat aacaccacct ctaataccaa caatagcacc ttcaccacca aagaaccac     1680 cacaggacca attttttgttt cttggattga cagttctacc aatgatgttg ttgacggttt    1740
cacagaccat caaggtttgt gggacagagg tcttaacgta gaaaacagca ccagcttttc    1800
tcaacatggt ggttaagacg gaatcaccct catcgtattt gtttaaccag gaaatgtaac    1860
ccatggaggt ttcgtaaccc ttaacacgca attggtcctt taaagagatt ggtaaaccgt    1920
gtaatggacc aactggtctc ttatgcttag cgtagtattc atctaattct ctagcttgag    1980
ctaaagcagc atctgggaag aattcgtgag cacagttggt taattgttga gcaatagcag    2040
ctctcttaca aaaagccaaa gtgacttcaa cagaagtcaa ctcaccagcg gccaacttgg    2100
agaccaaatc agcagcagag gcttcggtaa tcttcaattc agcctcagac aaaataccgg    2160
acttctttgg gaaatcaata acggaatctt cggcaggcaa agtttgaacc ttccattcgt    2220
caggaatggt tttagccaaa cgggcacgtt tgtcggcggc caattcttcc caggattgtg    2280
gcattttgta attaaaactt agattagatt gctatgcttt cttttctaatg agcaagaagt    2340 aaaaaaagtt gtaatagaac aagaaaaacg aaactgaaac ttgagaaatt gaagaccatt    2400
tattaactta aatatcaatg ggaggtcatc gaaagagaaa aaaatcaaaa aaaaattttt    2460
tcaagaaaaa gaaacgtgat aaaaatttt attgcctttt tcgacgaaga aaagaaacg     2520 aggcggtctc tttttcttt tccaaacctt tagtacgggt aattaacgcc accctagagg     2580
aagaaagagg ggaaatttag tatgctgtgc ttgggtgttt tgaagtggta cggcgatgcg    2640
cggagtccga aaaatctgg aagagtaaaa aaggagtaga aacatttga agctatggtg      2700 tgtggggat cacttgtggg ggattgggtg tgatgtaagg ataacttcgt atagcataca     2760
```

| | |
|---|---:|
| ttatacgaag ttatgcggcc gcgagaagat gcggccagca aaactaaaaa actgtattat | 2820 |
| aagtaaatgc atgtatacta aactcacaaa ttagagcttc aatttaatta tatcagttat | 2880 |
| tacccgggaa tctcggtcgt aatgattttt ataatgacga aaaaaaaaaa attggaaaga | 2940 |
| aaaagcttca tggcctttat aaaaaggaac catccaatac ctcgccagaa ccaagtaaca | 3000 |
| gtattttacg gggcacaaat caagaacaat aagacaggac tgtaaagatg gacgcattga | 3060 |
| actccaaaga acaacaagag ttccaaaaag tagtggaaca aaagcaaatg aaggatttca | 3120 |
| tgcgtttgta ctctaatctg gtagaaagat gtttttacaga ctgtgtcaat gacttcacaa | 3180 |
| catcaaagct aaccaataag gaacaaacat gcatcatgaa gtgctcagaa aagttcttga | 3240 |
| agcatagcga acgtgtaggg cagcgtttcc aagag | 3275 |

```
<210> SEQ ID NO 3
<211> LENGTH: 1132
<212> TYPE: DNA
<213> ORGANISM: Artificial Sequence
<220> FEATURE:
<223> OTHER INFORMATION: cre PCR fragment

<400> SEQUENCE: 3
```

| | |
|---|---:|
| ctctttttta cagatcatca aggaagtaat tatctacttt ttacaagaat tcatgtctaa | 60 |
| tttacttact gttcaccaaa acttgcctgc attaccagtt gacgcaacct ccgatgaagt | 120 |
| cagaaagaac cttatggata tgtttagaga tagacaagct ttctccgaac atacttggaa | 180 |
| aatgttatta tccgtttgta gatcctgggc cgcttggtgt aaacttaaca atagaaaatg | 240 |
| gtttcctgct gaaccagaag acgtcagaga ttacttactt tacttacaag ctagaggttt | 300 |
| ggctgttaaa actatccaac aacacttagg tcaattgaat atgttacaca gaagatccgg | 360 |
| tttaccaaga ccatccgatt ccaacgcagt ttcccttgtt atgagaagaa ttagaaaaga | 420 |
| aaatgttgac gctggtgaaa gagctaaaca agcattagca tttgaaagaa ccgatttcga | 480 |
| tcaagttaga tccttaatgg aaaattccga tagatgtcaa gatattagaa acttagcttt | 540 |
| cttaggtatt gcttacaaca cattattaag aatcgctgaa attgctagaa ttagagttaa | 600 |
| agatatttca agaaccgatg gcggtagaat gttaatccac attggcagaa caaaaacctt | 660 |
| agtctccaca gcaggcgtcg aaaaagcatt atcattaggt gttactaaat tagttgaacg | 720 |
| ttggattttcc gttccggtg ttgcagatga cccaaacaac tacttattct gtcgtgttag | 780 |
| aaaaaatggt gttgccgctc cttccgctac ctcacaatta tccacaagag cattagaagg | 840 |
| cattttttgaa gctacccaca gacttattta tggtgcaaaa gacgattccg gtcaaagata | 900 |
| tttagcttgg tctggtcatt ccgctagagt tggtgccgca agagacatgg caagagctgg | 960 |
| tgtttctatt cctgaaatta tgcaagccgg tggttggact aatgttaaca ttgttatgaa | 1020 |
| ctatatcaga aacttagatt ccgaaacagg tgctatggtt agattacttg aagacggtga | 1080 |
| ttaagctagc taagatccgc tctaaccgaa aaggaaggag ttagacaacc tg | 1132 |

```
<210> SEQ ID NO 4
<211> LENGTH: 6376
<212> TYPE: DNA
<213> ORGANISM: Artificial Sequence
<220> FEATURE:
<223> OTHER INFORMATION: pGP52 fragment

<400> SEQUENCE: 4
```

| | |
|---|---:|
| ctagctaaga tccgctctaa ccgaaaagga aggagttaga caacctgaag tctaggtccc | 60 |
| tatttatttt tttatagtta tgttagtatt aagaacgtta tttatatttc aaatttttct | 120 |

-continued

| | | | | |
|---|---|---|---|---|
| ttttttttctg | tacagacgcg | tgtacgcatg | taacattata | ctgaaaacct tgcttgagaa | 180 |
| ggttttggga | cgctcgaaga | tccagctgca | ttaatgaatc | ggccaacgcg cggggagagg | 240 |
| cggtttgcgt | attgggcgct | cttccgcttc | ctcgctcact | gactcgctgc gctcggtcgt | 300 |
| tcggctgcgg | cgagcggtat | cagctcactc | aaaggcggta | atacggttat ccacagaatc | 360 |
| aggggataac | gcaggaaaga | acatgtgagc | aaaaggccag | caaaaggcca ggaaccgtaa | 420 |
| aaaggccgcg | ttgctggcgt | ttttccatag | gctccgcccc | cctgacgagc atcacaaaaa | 480 |
| tcgacgctca | agtcagaggt | ggcgaaaccc | gacaggacta | taaagatacc aggcgtttcc | 540 |
| ccctggaagc | tccctcgtgc | gctctcctgt | tccgaccctg | ccgcttaccg gatacctgtc | 600 |
| cgcctttctc | ccttcgggaa | gcgtggcgct | ttctcatagc | tcacgctgta ggtatctcag | 660 |
| ttcggtgtag | gtcgttcgct | ccaagctggg | ctgtgtgcac | gaaccccccg ttcagcccga | 720 |
| ccgctgcgcc | ttatccggta | actatcgtct | tgagtccaac | ccggtaagac acgacttatc | 780 |
| gccactggca | gcagccactg | gtaacaggat | tagcagagcg | aggtatgtag gcggtgctac | 840 |
| agagttcttg | aagtggtggc | ctaactacgg | ctacactaga | aggacagtat ttggtatctg | 900 |
| cgctctgctg | aagccagtta | ccttcggaaa | aagagttggt | agctcttgat ccggcaaaca | 960 |
| aaccaccgct | ggtagcggtg | gtttttttgt | ttgcaagcag | cagattacgc gcagaaaaaa | 1020 |
| aggatctcaa | gaagatcctt | tgatcttttc | tacgggtct | gacgctcagt ggaacgaaaa | 1080 |
| ctcacgttaa | gggattttgg | tcatgagatt | atcaaaaagg | atcttcacct agatcctttt | 1140 |
| aaattaaaaa | tgaagtttta | aatcaatcta | agtatatat | gagtaaactt ggtctgacag | 1200 |
| ttaccaatgc | ttaatcagtg | aggcacctat | ctcagcgatc | tgtctatttc gttcatccat | 1260 |
| agttgcctga | ctccccgtcg | tgtagataac | tacgatacgg | gagggcttac catctggccc | 1320 |
| cagtgctgca | atgataccgc | gagacccacg | ctcaccggct | ccagatttat cagcaataaa | 1380 |
| ccagccagcc | ggaagggccg | agcgcagaag | tggtcctgca | actttatccg cctccatcca | 1440 |
| gtctattaat | tgttgccggg | aagctagagt | aagtagttcg | ccagttaata gtttgcgcaa | 1500 |
| cgttgttgcc | attgctacag | gcatcgtggt | gtcacgctcg | tcgtttggta tggcttcatt | 1560 |
| cagctccggt | tcccaacgat | caaggcgagt | tacatgatcc | cccatgttgt gcaaaaaagc | 1620 |
| ggttagctcc | ttcggtcctc | cgatcgttgt | cagaagtaag | ttggccgcag tgttatcact | 1680 |
| catggttatg | gcagcactgc | ataattctct | tactgtcatg | ccatccgtaa gatgcttttc | 1740 |
| tgtgactggt | gagtactcaa | ccaagtcatt | ctgagaatag | tgtatgcggc gaccgagttg | 1800 |
| ctcttgcccg | gcgtcaatac | gggataatac | cgcgccacat | agcagaactt taaaagtgct | 1860 |
| catcattgga | aaacgttctt | cggggcgaaa | actctcaagg | atcttaccgc tgttgagatc | 1920 |
| cagttcgatg | taacccactc | gtgcacccaa | ctgatcttca | gcatctttta ctttcaccag | 1980 |
| cgtttctggg | tgagcaaaaa | caggaaggca | aaatgccgca | aaaagggaa taagggcgac | 2040 |
| acggaaatgt | tgaatactca | tactcttcct | ttttcaatat | tattgaagca tttatcaggg | 2100 |
| ttattgtctc | atgagcggat | acatatttga | atgtatttag | aaaaataaac aaatagggt | 2160 |
| tccgcgcaca | tttccccgaa | aagtgccacc | tgaacgaagc | atctgtgctt cattttgtag | 2220 |
| aacaaaaatg | caacgcgaga | gcgctaattt | ttcaaacaaa | gaatctgagc tgcattttta | 2280 |
| cagaacagaa | atgcaacgcg | aaagcgctat | ttaccaacg | aagaatctgt gcttcatttt | 2340 |
| tgtaaaacaa | aaatgcaacg | cgagagcgct | aattttttcaa | acaaagaatc tgagctgcat | 2400 |
| ttttacagaa | cagaaatgca | acgcgagagc | gctattttac | caacaaagaa tctatacttc | 2460 |

-continued

```
tttttttgttc tacaaaaatg catcccgaga gcgctatttt tctaacaaag catcttagat    2520
tacttttttt ctcctttgtg cgctctataa tgcagtctct tgataacttt ttgcactgta    2580
ggtccgttaa ggttagaaga aggctacttt ggtgtctatt ttctcttcca taaaaaaagc    2640
ctgactccac ttcccgcgtt tactgattac tagcgaagct gcgggtgcat tttttcaaga    2700
taaaggcatc cccgattata ttctataccg atgtggattg cgcatacttt gtgaacagaa    2760
agtgatagcg ttgatgattc ttcattggtc agaaaattat gaacggtttc ttctattttg    2820
tctctatata ctacgtatag gaaatgttta cattttcgta ttgttttcga ttcactctat    2880
gaatagttct tactacaatt ttttgtcta aagagtaata ctagagataa acataaaaaa     2940
tgtagaggtc gagtttagat gcaagttcaa ggagcgaaag gtggatgggt aggttatata    3000
gggatatagc acagagatat atagcaaaga gatacttttg agcaatgttt gtggaagcgg    3060
tattcgcaat attttagtag ctcgttacag tccggtgcgt ttttggtttt ttgaaagtgc    3120
gtcttcagag cgcttttggt tttcaaaagc gctctgaagt tcctatactt tctagagaat    3180
aggaacttcg gaataggaac ttcaaagcgt ttccgaaaac gagcgcttcc gaaaatgcaa    3240
cgcgagctgc gcacatacag ctcactgttc acgtcgcacc tatatctgcg tgttgcctgt    3300
atatatatat acatgagaag aacggcatag tgcgtgttta tgcttaaatg cgtacttata    3360
tgcgtctatt tatgtaggat gaaaggtagt ctagtacctc ctgtgatatt atcccattcc    3420
atgcggggta tcgtatgctt ccttcagcac tacccttag ctgttctata tgctgccact     3480
cctcaattgg attagtctca tccttcaatg ctatcatttc ctttgatatt ggatcatact    3540
aagaaaccat tattatcatg acattaacct ataaaaatag gctatcacg aggccctttc     3600 gtctcgcgcg tttcggtgat gacggtgaaa acctctgaca catgcagctc ccggagacgg    3660
tcacagcttg tctgtaagcg gatgccggga gcagacaagc ccgtcagggc gcgtcagcgg    3720
gtgttggcgg gtgtcggggc tggcttaact atgcggcatc agagcagatt gtactgagag    3780
tgcaccatac cacagctttt caattcaatt catcatttt ttttttattct tttttttgat    3840 ttcggtttct ttgaaatttt tttgattcgg taatctccga acagaaggaa gaacgaagga    3900
aggagcacag acttagattg gtatatatac gcatatgtag tgttgaagaa acatgaaatt    3960
gcccagtatt cttaacccaa ctgcacagaa caaaaacctg caggaaacga agataaatca    4020
tgtcgaaagc tacatataag gaacgtgctg ctactcatcc tagtcctgtt gctgccaagc    4080
tatttaatat catgcacgaa aagcaaacaa acttgtgtgc ttcattggat gttcgtacca    4140
ccaaggaatt actggagtta gttgaagcat taggtcccaa aatttgttta ctaaaaacac    4200
atgtggatat cttgactgat ttttccatgg agggcacagt taagccgcta aaggcattat    4260
ccgccaagta caatttttta ctcttcgaag acagaaaatt tgctgacatt ggtaatacag    4320
tcaaattgca gtactctgcg ggtgtataca gaatagcaga atgggcagac attacgaatg    4380
cacacggtgt ggtgggccca ggtattgtta gcggtttgaa gcaggcggca gaagaagtaa    4440
caaaggaacc tagaggcctt ttgatgttag cagaattgtc atgcaagggc tccctatcta    4500
ctggagaata tactaagggt actgttgaca ttgcgaagag cgacaaagat tttgttatcg    4560
gctttattgc tcaaagagac atgggtggaa gagatgaagg ttacgattgg ttgattatga    4620
cacccggtgt gggtttagat gacaagggag acgcattggg tcaacagtat agaaccgtgg    4680
atgatgtggt ctctacagga tctgacatta ttattgttgg aagaggacta tttgcaaagg    4740
gaagggatgc taaggtagag ggtgaacgtt acagaaaagc aggctgggaa gcatatttga    4800
gaagatgcgg ccagcaaaac taaaaaactg tattataagt aaatgcatgt atactaaact    4860
```

```
cacaaattag agcttcaatt taattatatc agttattacc ctatgcggtg tgaaataccg    4920
cacagatgcg taaggagaaa ataccgcatc aggaaattgt aaacgttaat attttgttaa    4980
aattcgcgtt aaattttgt taaatcagct cattttttaa ccaataggcc gaaatcggca    5040 aaatcccttta taaatcaaaa gaatagaccg agatagggtt gagtgttgtt ccagtttgga    5100
acaagagtcc actattaaag aacgtggact ccaacgtcaa agggcgaaaa accgtctatc    5160
agggcgatgg cccactacgt gaaccatcac cctaatcaag tttttgggg tcgaggtgcc    5220 gtaaagcact aaatcggaac cctaaaggga gcccccgatt tagagcttga cggggaaagc    5280
cggcgaacgt ggcgagaaag gaagggaaga agcgaaagg agcgggcgct agggcgctgg    5340
caagtgtagc ggtcacgctg cgcgtaacca ccacacccgc cgcgcttaat gcgccgctac    5400
agggcgcgtc cattcgccat tcaggctgcg caactgttgg gaagggcgat cggtgcgggc    5460
ctcttcgcta ttacgccagc tgaattggag cgacctcatg ctatacctga aaagcaacc    5520 tgacctacag gaaagagtta ctcaagaata agaattttcg ttttaaaacc taagagtcac    5580
tttaaaattt gtatacactt attttttta aacttattt aataataaaa atcataaatc    5640
ataagaaatt cgcttattta gaagtgtcaa caacgtatct accaacgatt tgaccctttt    5700
ccatcttttc gtaaatttct ggcaaggtag acaagccgac aaccttgatt ggagacttga    5760
ccaaacctct ggcgaagaat tgttaattaa gccagaaaaa ggaagtgttt ccctccttct    5820
tgaattgatg ttaccctcat aaagcacgtg gcctcttatc gagaaagaaa ttaccgtcgc    5880
tcgtgatttg tttgcaaaaa gaacaaaact gaaaaaaccc agacacgctc gacttcctgt    5940
cttcctattg attgcagctt ccaatttcgt cacacaacaa ggtcctagcg acggctcaca    6000
ggttttgtaa caagcaatcg aaggttctgg aatggcggga aagggtttag taccacatgc    6060
tatgatgccc actgtgatct ccagagcaaa gttcgttcga tcgtactgtt actctctctc    6120
tttcaaacag aattgtccga atcgtgtgac aacaacagcc tgttctcaca cactcttttc    6180
ttctaaccaa gggggtggtt tagtttagta gaacctcgtg aaacttacat ttacatatat    6240
ataaacttgc ataaattggt caatgcaaga aatacatatt tggtcttttc taattcgtag    6300
tttttcaagt tcttagatgc tttctttttc tcttttttac agatcatcaa ggaagtaatt    6360
atctactttt tacaag                                                    6376
```

<210> SEQ ID NO 5
<211> LENGTH: 1548
<212> TYPE: DNA
<213> ORGANISM: Artificial Sequence
<220> FEATURE:
<223> OTHER INFORMATION: Sf GA variant #1

<400> SEQUENCE: 5

```
atgattagat taaccgtatt cctcactgca gttttgcag cagtcgcttc ctgtgttcca     60
gttgaattgg ataagagaaa tacaggccat ttccaagcat attctggtta caccgtagct    120
agatcaaact ttactcaatg gattcacgag caaccagccg tatcatggta ctatttgctt    180
cagaatatag actatccaga aggacaattc aagtctgcca agccaggggt cgttgtggct    240
tccccttcta catccgaacc tgattacttc taccaatgga ctagagatac tgctatcacc    300
ttcttgtcac ttatcgcgga agttgaggat cattcttttt caaatactac actagccaag    360
gtggttgaat actacatctc taatacttac acattacaaa gagtttccaa cccatctggt    420
aacttcgaca gtccaaatca cgacggtttg ggagaaccaa agtttaatgt tgatgataca    480
```

```
gcttatactg catcttgggg tagaccacaa aatgatggcc cagcgttgag agcatacgca    540
atttcaagat accttaacgc agtagcaaaa cacaacaacg gtaagttact gctcgctgga    600
caaaacggta ttccttactc ttcagcttct gatatctact ggaagattat caagccagat    660
cttcaacatg tgtcaaccca ttggtctaca tctggttttg atttgtggga agagaatcag    720
ggaacacatt tctttactgc gttggtccag ctaaaagcac ttagttacgg cattccttta    780
agtaagacct acaacgatcc tggtttcact agttggctag aaaagcaaaa ggatgcttta    840
aactcttata tcaacagctc tggtttcgta aactctggca aaaagcatat agtggagagc    900
cctcaactat cttcaagagg agggttggat agcgccacat acattgcagc cttaatcaca    960
catgatattg gcgacgacga cacttacaca cctttcaacg ttgacaactc ctatgtcttg    1020
aactcactgt attaccttct agtcgataac aaaaaccgtt acaaaatcaa tggtaactac    1080
aaggccggtg ctgctgttgg tagatacccca gaggatgttt acaacggtgt gggacatca    1140 gaaggcaatc catggcaatt agctacagcc tacgccggcc aaacatttta cacactggct    1200
tacaactcat tgaaaaacaa aaaaaactta gtgattgaaa agttgaacta cgacctctac    1260
aattctttca tagcagattt atccaagatc gatagttctt acgcatcaaa agactccttg    1320
actttgacct acggttctga caactacaaa aacgtcataa agtcactatt acagtttgga    1380
gattcattcc tgaaggtctt gctcgatcac attgatgata tggacaatt aacagaagag    1440 atcaatagat acacagggtt ccaggctggt gctgttagtt tgacatggtc ctctggttca    1500
ttactttcag caaaccgtgc gagaaataag ttgattgaac tattgtag              1548

<210> SEQ ID NO 6
<211> LENGTH: 1548
<212> TYPE: DNA
<213> ORGANISM: Artificial Sequence
<220> FEATURE:
<223> OTHER INFORMATION: Sf GA variant #2

<400> SEQUENCE: 6
atgatcagac ttacagtttt cctaacagcc gttttcgccg ccgttgcatc atgtgtccca     60
gtagaattgg ataagagaaa caccggccat ttccaagcat attcaggata caccgttgca    120
cgttctaatt tcacacaatg gattcatgag cagcctgctg tgtcctggta ctacttatta    180
caaaacattg attatcctga gggacaattc aagtcagcga aaccaggcgt tgtggttgct    240
tctccatcca cttcagaacc agactacttc taccagtgga cccgtgacac agcaataact    300
ttcttatctt tgatagcaga agtagaagat cactcatttt caaatacaac tctagctaag    360
gttgtcgaat actacatctc taacacatac accctacaaa gagtttctaa cccatctggt    420
aatttcgata gcccaaatca cgatggtctg ggtgaaccaa agttcaacgt tgacgacact    480
gcttacactg catcatgggg cagacctcaa aacgacggtc cagccttaag agcttacgcg    540
atctcaagat atttgaacgc agttgccaag cataacaacg gtaagctatt gctcgcgggt    600
caaaatggta ttccttactc atctgcatca gatatctact ggaagattat caagccagat    660
ttacaacatg taagtactca ctggagtaca tctggttttg acttatggga agagaatcaa    720
ggtacacatt tctttactgc acttgtccag ttaaaagctc tttcatacgg tataccttg    780 tctaagacat ataacgatcc aggatttact tcttggttgg aaaagcagaa ggatgccttg    840
aactcttaca tcaattccag cggcttcgtc aactccggga aaaagcacat tgtcgaatct    900
cctcaattat ctagtagagg gggtcttgat agcgctactt acatcgctgc tctaattaca    960
catgatattg gtgatgatga tacatacact cctttttaacg tagataattc ttatgtgctg   1020
```

| | |
|---|---|
| aactctttat actatctgct tgtagacaac aaaaacagat acaagatcaa cgggaactac | 1080 |
| aaagcaggag ctgcagttgg tagatacccca gaagatgtgt acaatggagt gggaacctca | 1140 |
| gagggaaacc catggcaatt ggcgacagca tacgccggcc aaaccttta cacactggct | 1200 |
| tacaattctc tcaaaaacaa aaaaaatttg gttattgaga agttgaatta cgatctatac | 1260 |
| aactccttta tagctgactt aagtaagatt gactcctctt acgcttctaa ggattcattg | 1320 |
| acattgacct acggctcaga taactacaaa aatgtcatta agtcacttt acaattcggg | 1380 |
| gattcttct tgaaagtctt gttggaccat attgatgata atggtcagct aacagaggaa | 1440 |
| atcaacagat atacaggttt tcaagctggc gcagtttccc tcacttggag tagtggttca | 1500 |
| ctcttatctg caaacagagc cagaaacaag ttgatcgaat tgctttag | 1548 |

<210> SEQ ID NO 7
<211> LENGTH: 1548
<212> TYPE: DNA
<213> ORGANISM: Artificial Sequence
<220> FEATURE:
<223> OTHER INFORMATION: Sf GA variant #3

<400> SEQUENCE: 7

| | |
|---|---|
| atgatcagac ttactgtttt cctcacagcc gttttgcag cagtagcttc ttgtgttcca | 60 |
| gttgaattgg ataagagaaa tacaggtcat ttccaagctt actctggtta cactgtggct | 120 |
| agatctaact tcacacaatg gattcatgaa cagcctgccg tgagttggta ctatttgcta | 180 |
| caaaacattg attaccctga gggtcaattc aaatcagcta agccaggtgt tgttgtcgcg | 240 |
| agcccatcaa cttctgaacc agattacttc taccaatgga ctagagatac cgcaataacc | 300 |
| ttcttatctc taatcgcaga ggtagaagat cactctttt caaatactac cctggcaaaa | 360 |
| gtggtcgagt actacatctc aaacacatac accttgcaga gagtctcaaa cccatcagga | 420 |
| aacttcgatt ctcctaatca tgacggctta ggagaaccaa agtttaatgt tgacgatacc | 480 |
| gcttatactg catcttgggg tagaccacag aatgatggcc ctgccttacg tgcatacgcc | 540 |
| atttccagat atctcaacgc tgtagcgaag cacaacaacg gtaagctgct tttagctggt | 600 |
| caaaatggga taccatactc ttccgcttca gacatttact ggaagattat caaaccagac | 660 |
| ttgcagcatg tcagtacaca ttggtcaact tctggttttg atttgtggga agagaaccaa | 720 |
| ggcactcact tctttacagc cttggttcaa ctaaaggcat tgtcttacgg aatccctttg | 780 |
| tccaagacat acaatgatcc tggattcact agttggctag aaaagcaaaa ggatgcactg | 840 |
| aactcataca ttaacagttc aggctttgtg aactccggta aaaagcatat tgttgaaagc | 900 |
| ccacaactat ctagcagagg tggtttagat tctgcaacct acatagcagc cttgatcaca | 960 |
| cacgacattg ggatgacga tacatacaca ccattcaacg tcgacaattc atacgttttg | 1020 |
| aatagcttat actacctact ggtagataac aaaaacagat ataagatcaa tggcaactac | 1080 |
| aaggccggtg ctgccgtagg aagataccct gaagatgtct caacggagt tggtacatca | 1140 |
| gaaggtaacc catggcaatt agcaacagca tatgcgggcc agacattta cactttggct | 1200 |
| tacaattcat tgaaaaacaa aaaaaattta gtgatagaaa agcttaacta tgaccttttac | 1260 |
| aactctttca ttgccgattt atccaagatt gattcctcct acgcatcaaa ggactccttg | 1320 |
| acacttacat acggttctga caactacaaa aatgttatca agtctctctt gcaatttggt | 1380 |
| gattcttct tgaaggtttt actcgatcat atcgatgata atggtcaact aactgaggaa | 1440 |
| atcaacagat acactgggtt ccaagctgga gctgtctctt taacatggag ttcagggagt | 1500 |

```
ttgttatctg ctaacagagc gcgtaacaaa cttattgagc ttctgtag          1548
```

```
<210> SEQ ID NO 8
<211> LENGTH: 1548
<212> TYPE: DNA
<213> ORGANISM: Artificial Sequence
<220> FEATURE:
<223> OTHER INFORMATION: Sf GA variant #4

<400> SEQUENCE: 8
atgattagat taacagtatt tcttacagcc gttttcgcag ccgtcgcatc ctgtgttcca    60
gtagaattag ataagcgtaa tacaggacat tttcaagctt actctggcta tacagttgcg   120
agatctaact ttacacaatg gattcacgaa cagccagcag tttcttggta ctatttgctc   180
caaaacatcg actaccctga aggccaattc aagtctgcaa agccaggagt ggtcgtcgct   240
tctcctagta cttcagaacc agattacttc taccagtgga caagagacac tgctattacc   300
ttcctgagct taatcgctga agttgaagat cactcttttt ctaatacaac actggccaaa   360
gtagttgagt actacatctc taacacttac actctacaaa gagtgtcaaa cccttctggg   420
aacttcgaca gcccaaacca tgatggtttg ggggagccaa aattcaacgt tgatgataca   480
gcctacaccg catcttgggg tagaccacaa acgacggaca cagcttttaag agcatacgca   540
atatctcgtt accttaatgc tgttgcaaag cacaataatg gaaagttgtt gttggctggt   600
caaaacggta ttccttactc ttcagcatct gatatctact ggaagattat caagccagat   660
cttcaacacg tatccacaca ttggtcaacc tccggcttcg atttatggga ggaaaatcag   720
ggtacacatt tcttccaccgc tctagtgcaa ttgaaggctt tgagttacgg cattccattg   780
tctaagactt acaacgatcc tggtttcacc tcatggcttg aaaagcagaa ggatgccctg   840
aatagctaca tcaactcatc tggttttgtt aactcaggga aaaagcatat agttgaatcc   900
ccacaactat catcaagagg aggtttagac tccgccacat acattgctgc cttgattaca   960
catgatattg gggatgatga cacatatact ccatttaacg tcgataacag ttatgtcctt  1020
aattccttat actatttgtt ggtcgataac aaaaatagat acaaaatcaa cggcaactac  1080
aaggctggcg cagcggtggg tagatacccct gaggatgttt acaatggtgt aggtacatct  1140
gaaggcaatc catggcaatt agcgactgct tacgctggac aaactttcta cacacttgcg  1200
tacaactcat tgaaaaacaa aaaaaaccta gtcattgaaa agttgaatta cgatctgtac  1260
aactctttca tcgcagacct atcaaagatt gactcatctt atgcaagtaa agattcacta  1320
actttaaccct acggtagtga taactacaaa aacgttatca agtctttact ccagtttggt  1380
gattcattct tgaaggtgtt gttagatcat atagacgaca atggtcaact cacagaggag  1440
ataaacagat acactggttt tcaagcagga gctgtttcac ttacttggtc aagtggttct  1500
ttgctttccg ccaacagagc cagaaacaag ctcatcgaat tactatag              1548
```

```
<210> SEQ ID NO 9
<211> LENGTH: 8719
<212> TYPE: DNA
<213> ORGANISM: Artificial Sequence
<220> FEATURE:
<223> OTHER INFORMATION: pAV47

<400> SEQUENCE: 9
atcacatagg aagcaacagg cgcgttggac ttttaatttt cgaggaccgc gaatccttac    60
atcacaccca atccccacaa agtgatcccc cacacaccat agcttcaaaa tgttttctact  120
ccttttttac tcttccagat tttctcggac tccgcgcatc gccgtaccac ttcaaaacac  180
```

```
ccaagcacag catactaaat ttcccctctt tcttcctcta gggtgtcgtt aattacccgt    240
actaaaggtt tggaaaagaa aaagagacc gcctcgtttc ttttcttcg tcgaaaagg       300 caataaaaat ttttatcacg tttcttttc ttgaaaattt ttttttttga ttttttctc      360 tttcgatgac ctcccattga tatttaagtt aataaacggt cttcaatttc tcaagtttca    420
gtttcatttt tcttgttcta ttacaacttt ttttacttct tgctcattag aaagaaagca    480
tagcaatcta atctaagttt taattacaaa tctagaatga gtgaatctcc aatgttcgct    540
gccaacggca tgccaaaggt aaatcaaggt gctgaagaag atgtcagaat tttaggttac    600
gacccattag cttctccagc tctccttcaa gtgcaaatcc cagccacacc aacttctttg    660
gaaactgcca agagaggtag aagagaagct atagatatta ttaccggtaa agacgacaga    720
gttcttgtca ttgtcggtcc ttgttccatc catgatcttg aagccgctca agaatacgct    780
ttgagattaa agaaattgtc agatgaatta aaaggtgatt tatccatcat tatgagagca    840
tacttggaga agccaagaac aaccgtcggc tggaaaggtc taattaatga ccctgatgtt    900
aacaacactt tcaacatcaa caagggtttg caatccgcta gacaattgtt tgtcaacttg    960
acaaatatcg gtttgccaat tggttctgaa atgcttgata ccatttctcc taaatacttg    1020
gctgatttgg tctccttcgg tgccattggt gccagaacca ccgaatctca actgcacaga    1080
gaattggcct ccggtttgtc tttcccagtt ggtttcaaga acggtaccga tggtaccta    1140 aatgttgctg tggatgcttg tcaagccgct gctcattctc accatttcat gggtgttact    1200
aagcatggtt ttgctgctat caccactact aagggtaacg aacactgctt cgttattcta    1260
agaggtggta aaagggtac caactacgac gctaagtccg ttgcagaagc taaggctcaa    1320
ttgcctgccg gttccaacgg tctaatgatt gactactctc acggtaactc caataaggat    1380
ttcagaaacc aaccaaggt caatgacgtt gtttgtgagc aaatcgctaa cggtgaaaac    1440
gccattaccg gtgtcatgat tgaatcaaac atcaacgaag gtaaccaagg catcccagcc    1500
gaaggtaaag ccggcttgaa atatggtgtt tccatcactg atgcttgtat aggttgggaa    1560
actactgaag acgtcttgag gaaattggct gctgctgtca gacaaagaag agaagttaac    1620
aagaaataga tgttttttta atgatatatg taacgtacat tctttcctct accactgcca    1680
attcggtatt attaattgt gtttagcgct atttactaat taactagaaa ctcaattttt     1740
aaaggcaaag ctcgctgacc tttcactgat ttcgtggatg ttatactatc agttactctt    1800
ctgcaaaaaa aaattgagtc atatcgtagc tttgggatta ttttctctc tctccacggc     1860 taattaggta atcatgaaaa aatgaaaaat tcatgagaaa agagtcagac atcgaaacat    1920
acataagttg atattccttt gatatcgacg actactcaat caggttttaa aagaaaagag    1980
gcagctattg aagtagcagt atccagttta ggttttttaa ttatttacaa gtaaagaaaa    2040
agagaatgcc ggtcgttcac ggcggccgcg ccagaaaaag gaagtgtttc cctccttctt    2100
gaattgatgt taccctcata aagcacgtgg cctcttatcg agaagaaat taccgtcgct     2160 cgtgatttgt ttgcaaaaag aacaaaactg aaaaaaccca gacacgctcg acttcctgtc    2220
ttcctattga ttgcagcttc caatttcgtc acacaacaag gtcctagcga cggctcacag    2280
gttttgtaac aagcaatcga aggttctgga atggcgggaa agggtttagt accacatgct    2340
atgatgccca ctgtgatctc cagagcaaag ttcgttcgat cgtactgtta ctctctctct    2400
ttcaaacaga attgtccgaa tcgtgtgaca acaacagcct gttctcacac actcttttct    2460
tctaaccaag ggggtggttt agtttagtag aacctcgtga aacttacatt tacatatata    2520
```

| | |
|---|---|
| taaacttgca taaattggtc aatgcaagaa atacatattt ggtcttttct aattcgtagt | 2580 |
| ttttcaagtt cttagatgct ttctttttct ctttttttaca gatcatcaac tcttttttac | 2640 |
| agatcatcaa ggaagtaatt atctactttt tacaagaatt catgtctaat ttacttactg | 2700 |
| ttcaccaaaa cttgcctgca ttaccagttg acgcaacctc cgatgaagtc agaaagaacc | 2760 |
| ttatggatat gtttagagat agacaagctt tctccgaaca tacttggaaa atgttattat | 2820 |
| ccgtttgtag atcctgggcc gcttggtgta aacttaacaa tagaaaatgg tttcctgctg | 2880 |
| aaccagaaga cgtcagagat tacttacttt acttacaagc tagaggtttg gctgttaaaa | 2940 |
| ctatccaaca acacttaggt caattgaata tgttacacag aagatccggt ttaccaagac | 3000 |
| catccgattc caacgcagtt tcccttgtta tgagaagaat tagaaaagaa aatgttgacg | 3060 |
| ctggtgaaag agctaaacaa gcattagcat ttgaaagaac cgatttcgat caagttagat | 3120 |
| ccttaatgga aaattccgat agatgtcaag atattagaaa cttagctttc ttaggtattg | 3180 |
| cttacaacac attattaaga atcgctgaaa ttgctagaat tagagttaaa gatatttcaa | 3240 |
| gaaccgatgg cggtagaatg ttaatccaca ttggcagaac aaaaaccttg gtctccacag | 3300 |
| caggcgtcga aaaagcatta tcattaggtg ttactaaatt agttgaacgt tggatttccg | 3360 |
| tttccggtgt tgcagatgac ccaaacaact acttattctg tcgtgttaga aaaaatggtg | 3420 |
| ttgccgctcc ttccgctacc tcacaattat ccacaagagc attagaaggc atttttgaag | 3480 |
| ctacccacag acttatttat ggtgcaaaag acgattccgg tcaaagatat ttagcttggt | 3540 |
| ctggtcattc cgctagagtt ggtgccgcaa gagacatggc aagagctggt gtttctattc | 3600 |
| ctgaaattat gcaagccggt ggttggacta atgttaacat tgttatgaac tatatcagaa | 3660 |
| acttagattc cgaaacaggt gctatggtta gattacttga agacggtgat taagctagct | 3720 |
| aagatccgct ctaaccgaaa aggaaggagt tagacaaccct gaagtctagg tccctattta | 3780 |
| ttttttttata gttatgttag tattaagaac gttatttata tttcaaattt ttctttttttt | 3840 |
| tctgtacaga cgcgtgtacg catgtaacat tatactgaaa accttgcttg agaaggtttt | 3900 |
| gggacgctcg aaggagctcc aattcgccct atagtgagtc gtattacaat tcactggccg | 3960 |
| tcgttttaca acgtcgtgac tgggaaaacc ctggcgttac ccaacttaat cgccttgcag | 4020 |
| cacatccccc cttcgccagc tggcgtaata gcgaagaggc ccgcaccgat cgcccttccc | 4080 |
| aacagttgcg cagcctgaat ggcgaatggc gcgacgcgcc ctgtagcggc gcattaagcg | 4140 |
| cggcgggtgt ggtggttacg cgcagcgtga ccgctacact tgccagcgcc ctagcgcccg | 4200 |
| ctcctttcgc tttcttccct tcctttctcg ccacgttcgc cggctttccc cgtcaagctc | 4260 |
| taaatcgggg gctcccttta gggttccgat ttagtgcttt acggcacctc gaccccaaaa | 4320 |
| aacttgatta gggtgatggt tcacgtagtg gccatcgcc ctgatagacg ttttttcgcc | 4380 |
| ctttgacgtt ggagtccacg ttctttaata gtggactctt gttccaaact ggaacaacac | 4440 |
| tcaaccctat ctcggtctat tcttttgatt tataagggat tttgccgatt tcggcctatt | 4500 |
| ggttaaaaaa tgagctgatt taacaaaaat ttaacgcgaa ttttaacaaa atattaacgt | 4560 |
| ttacaatttc ctgatgcggt attttctcct tacgcatctg tgcggtattt cacaccgcag | 4620 |
| ggtaataact gatataatta aattgaagct ctaatttgtg agtttagtat acatgcattt | 4680 |
| acttataata cagttttttta gttttgctgg ccgcatcttc tcaaatatgc ttcccagcct | 4740 |
| gcttttctgt aacgttcacc ctctaccttag catcccttc cctttgcaaa tagtcctctt | 4800 |
| ccaacaataa taatgtcaga tcctgtagag accacatcat cccacggttct atactgttga | 4860 |
| cccaatgcgt ctcccttgtc atctaaaccc acaccgggtg tcataatcaa ccaatcgtaa | 4920 |

```
ccttcatctc ttccacccat gtctctttga gcaataaagc cgataacaaa atctttgtcg    4980
ctcttcgcaa tgtcaacagt acccttagta tattctccag tagatagggga gcccttgcat    5040 gacaattctg ctaacatcaa aaggcctcta ggttcctttg ttacttcttc tgccgcctgc    5100
ttcaaaccgc taacaatacc tgggcccacc acaccgtgtg cattcgtaat gtctgcccat    5160
tctgctattc tgtatacacc cgcagagtac tgcaatttga ctgtattacc aatgtcagca    5220
aattttctgt cttcgaagag taaaaaattg tacttggcgg ataatgcctt tagcggctta    5280
actgtgccct ccatggaaaa atcagtcaag atatccacat gtgtttttag taaacaaatt    5340
ttgggaccta atgcttcaac taactccagt aattccttgg tggtacgaac atccaatgaa    5400
gcacacaagt ttgtttgctt ttcgtgcatg atattaaata gcttggcagc aacaggacta    5460
ggatgagtag cagcacgttc cttatatgta gctttcgaca tgatttatct tcgtttcctg    5520 caggttttg ttctgtgcag ttgggttaag aatactgggc aatttcatgt ttcttcaaca    5580
ctacatatgc gtatatatac caatctaagt ctgtgctcct tccttcgttc ttccttctgt    5640
tcggagatta ccgaatcaaa aaatttcaa agaaaccgaa atcaaaaaaa agaataaaaa    5700
aaaaatgatg aattgaattg aaaagcgtgg tgcactctca gtacaatctg ctctgatgcc    5760
gcatagttaa gccagccccg acaccgcca acaccgctg acgcgccctg acgggcttgt    5820
ctgctcccgg catccgctta cagacaagct gtgaccgtct ccgggagctg catgtgtcag    5880
aggttttcac cgtcatcacc gaaacgcgcg agacgaaagg gcctcgtgat acgcctattt    5940
ttataggtta atgtcatgat aataatggtt tcttaggacg gatcgcttgc ctgtaactta    6000
cacgcgcctc gtatctttta atgatggaat aatttgggaa tttactctgt gtttatttat    6060
ttttatgttt tgtatttgga ttttagaaag taaataaaga aggtagaaga gttacggaat    6120
gaagaaaaaa aaataaacaa aggtttaaaa aatttcaaca aaaagcgtac tttacatata    6180
tatttattag acaagaaaag cagattaaat agatatacat tcgattaacg ataagtaaaa    6240
tgtaaaatca caggattttc gtgtgtggtc ttctacacag acaagatgaa acaattcggc    6300
attaatacct gagagcagga agagcaagat aaaaggtagt atttgttggc gatcccccta    6360
gagtctttta catcttcgga aaacaaaaac tattttttct ttaatttctt ttttttacttt    6420 ctatttttaa tttatatatt tatattaaaa aatttaaatt ataattattt ttatagcacg    6480
tgatgaaaag gacccaggtg gcacttttcg gggaaatgtg cgcggaaccc ctatttgttt    6540 attttttctaa atacattcaa atatgtatcc gctcatgaga caataaccct gataaatgct    6600
tcaataatat tgaaaaagga agagtatgag tattcaacat ttccgtgtcg cccttattcc    6660 ctttttttgcg gcattttgcc ttcctgtttt tgctcaccca gaaacgctgg tgaaagtaaa    6720
agatgctgaa gatcagttgg gtgcacgagt gggttacatc gaactggatc tcaacagcgg    6780
taagatcctt gagagttttc gccccgaaga acgttttcca atgatgagca cttttaaagt    6840
tctgctatgt ggcgcggtat tatcccgtat tgacgccggg caagagcaac tcggtcgccg    6900
catacactat tctcagaatg acttggttga gtactcacca gtcacagaaa agcatcttac    6960
ggatggcatg acagtaagag aattatgcag tgctgccata accatgagtg ataacactgc    7020
ggccaactta cttctgacaa cgatcggagg accgaaggag ctaaccgctt ttttttcacaa    7080 catggggggat catgtaactc gccttgatcg ttgggaaccg gagctgaatg aagccatacc    7140
aaacgacgag cgtgacacca cgatgcctgt agcaatggca acaacgttgc gcaaactatt    7200
aactggcgaa ctacttactc tagcttcccg gcaacaatta atagactgga tggaggcgga    7260
```

```
taaagttgca ggaccacttc tgcgctcggc ccttccggct ggctggttta ttgctgataa    7320
atctggagcc ggtgagcgtg ggtctcgcgg tatcattgca gcactgggc cagatggtaa      7380 gccctcccgt atcgtagtta tctacacgac gggcagtcag gcaactatgg atgaacgaaa    7440
tagacagatc gctgagatag gtgcctcact gattaagcat tggtaactgt cagaccaagt    7500
ttactcatat atactttaga ttgatttaaa acttcatttt taatttaaaa ggatctaggt    7560
gaagatcctt tttgataatc tcatgaccaa atcccttaa cgtgagtttt cgttccactg      7620
agcgtcagac cccgtagaaa agatcaaagg atcttcttga tccttttt ttctgcgcgt       7680 aatctgctgc ttgcaaacaa aaaaaccacc gctaccagcg gtggtttgtt tgccggatca    7740
agagctacca actcttttc cgaaggtaac tggcttcagc agagcgcaga taccaaatac     7800
tgtccttcta gtgtagccgt agttaggcca ccacttcaag aactctgtag caccgcctac    7860
ataccctgct ctgctaatcc tgttaccagt ggctgctgcc agtggcgata agtcgtgtct    7920 taccggttg gactcaagac gatagttacc ggataaggcg cagcggtcgg gctgaacggg     7980
gggttcgtgc acacagccca gcttggagcg aacgacctac accgaactga gatacctaca    8040
gcgtgagcat tgagaaagcg ccacgcttcc cgaagggaga aaggcggaca ggtatccggt    8100
aagcggcagg gtcggaacag gagagcgcac gagggagctt ccaggggga acgcctggta     8160 tctttatagt cctgtcgggt ttcgccacct ctgacttgag cgtcgatttt tgtgatgctc    8220 gtcaggggg ccgagcctat ggaaaaacgc cagcaacgcg gcctttttac ggttcctggc     8280
cttttgctgg cctttgctc acatgttctt tcctgcgtta tcccctgatt ctgtggataa     8340
ccgtattacc gcctttgagt gagctgatac cgctcgccgc agccgaacga ccgagcgcag    8400
cgagtcagtg agcgaggaag cggaagagcg cccaatacgc aaaccgcctc tccccgcgcg    8460
ttggccgatt cattaatgca gctggcacga caggtttccc gactggaaag cgggcagtga    8520
gcgcaacgca attaatgtga gttacctcac tcattaggca ccccaggctt tacactttat    8580
gcttccggct cctatgttgt gtggaattgt gagcggataa caatttcaca caggaaacag    8640
ctatgaccat gattacgcca agctcggaat taaccctcac taaagggaac aaaagctggg    8700
taccgggccc cccctcgag                                                  8719
```

<210> SEQ ID NO 10
<211> LENGTH: 1632
<212> TYPE: DNA
<213> ORGANISM: Artificial Sequence
<220> FEATURE:
<223> OTHER INFORMATION: pTAN08

<400> SEQUENCE: 10

```
ggcaacggtt catcatctca tggatctgca catgaacaaa caccagagtc aaacgacgtt     60
gaaattgagg ctactgcgcc aattgatgac aatacagacg atgataacaa accgaagtta    120
tctgatgtag aaaaggatta gagatgctaa gagatagtga tgatatttca taaataatgt    180
aattctatat atgttaatta cctttttgc gaggcatatt tatggtgaag ataagttt      240 gaccatcaaa gaaggttaat gtggctgtgg tttcagggtc cataaagctt ttcaattcat    300
cttttttttt tttgttcttt tttttgattc cggtttcttt gaattttttt tgattcggta    360
atctccgagc agaaggaaga acgaaggaag gagcacagac ttagattggt atatatacgc    420
atatgtggtg ttgaagaaac atgaaattgc ccagtattct taaccccaact gcacagaaca    480 aaaacctgca ggaaacgaag ataaatcatg tcgaaagcta catataagga acgtgctgct    540
actcatccta gtcctgttgc tgccaagcta tttaatatca tgcacgaaaa gcaaacaaac    600
```

```
ttgtgtgctt cattggatgt tcgtaccacc aaggaattac tggagttagt tgaagcatta    660
ggtcccaaaa tttgtttact aaaaacacat gtggatatct tgactgattt ttccatggag    720
ggcacagtta agccgctaaa ggcattatcc gccaagtaca attttttact cttcgaagac    780
agaaaatttg ctgacattgg taatacagtc aaattgcagt actctgcggg tgtatacaga    840
atagcagaat gggcagacat tacgaatgca cacggtgtgg tgggcccagg tattgttagc    900
ggtttgaagc aggcggcgga agaagtaaca aggaaccta gaggccttt tgatgttagca    960
gaattgtcat gcaagggctc cctagctact ggagaatata ctaagggtac tgttgacatt   1020
gcgaagagcg acaaagattt tgttatcggc tttattgctc aaagagacat gggtggaaga   1080
gatgaaggtt acgattggtt gattatgaca cccggtgtgg gtttagatga caagggagac   1140
gcattgggtc aacagtatag aaccgtggat gatgtggtct ctacaggatc tgacattatt   1200
attgttggaa gaggactatt tgcaaaggga agggatgcta aggtagaggg tgaacgttac   1260
agaaaagcag gctgggaagc atatttgaga agatgcggcc agcaaaacta aaaaactgta   1320
ttataagtaa atgcatgtat actaaactca caaattagag cttcaattta attatatcag   1380
ttattacccg ggaatctcgg tcgtaatgat ttttataatg acgaaaaaaa aaaaattgga   1440
aagaaaaagc ttcatggcct ttataaaaag gaaccatcca atacctcgcc agaaccaagt   1500
aacagtattt tacggggcac aaatcaagaa caataagaca ggactgtaaa gatgggacgca   1560
ttgaactcca aagaacaaca agagttccaa aaagtagtgg aacaaaagca atgaaggat   1620
ttcatgcgtt tg                                                       1632

<210> SEQ ID NO 11
<211> LENGTH: 515
<212> TYPE: PRT
<213> ORGANISM: Saccharomycopsis fibuligera

<400> SEQUENCE: 11

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
```

```
            180             185              190
Asn Gly Lys Leu Leu Ala Gly Gln Asn Gly Ile Pro Tyr Ser Ser
            195             200              205

Ala Ser Asp Ile Tyr Trp Lys Ile Ile Lys Pro Asp Leu Gln His Val
            210             215              220

Ser Thr His Trp Ser Thr Ser Gly Phe Asp Leu Trp Glu Glu Asn Gln
225             230              235              240

Gly Thr His Phe Phe Thr Ala Leu Val Gln Leu Lys Ala Leu Ser Tyr
            245             250              255

Gly Ile Pro Leu Ser Lys Thr Tyr Asn Asp Pro Gly Phe Thr Ser Trp
            260             265              270

Leu Glu Lys Gln Lys Asp Ala Leu Asn Ser Tyr Ile Asn Ser Ser Gly
            275             280              285

Phe Val Asn Ser Gly Lys Lys His Ile Val Glu Ser Pro Gln Leu Ser
            290             295              300

Ser Arg Gly Gly Leu Asp Ser Ala Thr Tyr Ile Ala Ala Leu Ile Thr
305             310              315              320

His Asp Ile Gly Asp Asp Asp Thr Tyr Thr Pro Phe Asn Val Asp Asn
            325             330              335

Ser Tyr Val Leu Asn Ser Leu Tyr Tyr Leu Leu Val Asp Asn Lys Asn
            340             345              350

Arg Tyr Lys Ile Asn Gly Asn Tyr Lys Ala Gly Ala Ala Val Gly Arg
            355             360              365

Tyr Pro Glu Asp Val Tyr Asn Gly Val Gly Thr Ser Glu Gly Asn Pro
            370             375              380

Trp Gln Leu Ala Thr Ala Tyr Ala Gly Gln Thr Phe Tyr Thr Leu Ala
385             390              395              400

Tyr Asn Ser Leu Lys Asn Lys Asn Leu Val Ile Glu Lys Leu Asn
            405             410              415

Tyr Asp Leu Tyr Asn Ser Phe Ile Ala Asp Leu Ser Lys Ile Asp Ser
            420             425              430

Ser Tyr Ala Ser Lys Asp Ser Leu Thr Leu Tyr Gly Ser Asp Asn
            435             440              445

Tyr Lys Asn Val Ile Lys Ser Leu Leu Gln Phe Gly Asp Ser Phe Leu
            450             455              460

Lys Val Leu Leu Asp His Ile Asp Asp Asn Gly Gln Leu Thr Glu Glu
465             470              475              480

Ile Asn Arg Tyr Thr Gly Phe Gln Ala Gly Ala Val Ser Leu Thr Trp
            485             490              495

Ser Ser Gly Ser Leu Leu Ser Ala Asn Arg Ala Arg Asn Lys Leu Ile
            500             505              510

Glu Leu Leu
        515

<210> SEQ ID NO 12
<211> LENGTH: 19
<212> TYPE: PRT
<213> ORGANISM: Artificial Sequence
<220> FEATURE:
<223> OTHER INFORMATION: MFalpha2 signal sequence

<400> SEQUENCE: 12

Met Lys Phe Ile Ser Thr Phe Leu Thr Phe Ile Leu Ala Ala Val Ser
1               5                   10                  15

Val Thr Ala
```

<210> SEQ ID NO 13
<211> LENGTH: 17
<212> TYPE: PRT
<213> ORGANISM: Artificial Sequence
<220> FEATURE:
<223> OTHER INFORMATION: PHO5 signal sequence

<400> SEQUENCE: 13

Met Phe Lys Ser Val Val Tyr Ser Ile Leu Ala Ala Ser Leu Ala Asn
1               5                   10                  15

Ala

<210> SEQ ID NO 14
<211> LENGTH: 516
<212> TYPE: PRT
<213> ORGANISM: Artificial Sequence
<220> FEATURE:
<223> OTHER INFORMATION: MFalpha2- Sf GA protein

<400> SEQUENCE: 14

Met Lys Phe Ile Ser Thr Phe Leu Thr Phe Ile Leu Ala Ala Val Ser
1               5                   10                  15

Val Thr Ala Val Pro Val Glu Leu Asp Lys Arg Asn Thr Gly His Phe
            20                  25                  30

Gln Ala Tyr Ser Gly Tyr Thr Val Ala Arg Ser Asn Phe Thr Gln Trp
        35                  40                  45

Ile His Glu Gln Pro Ala Val Ser Trp Tyr Tyr Leu Leu Gln Asn Ile
    50                  55                  60

Asp Tyr Pro Glu Gly Gln Phe Lys Ser Ala Lys Pro Gly Val Val Val
65                  70                  75                  80

Ala Ser Pro Ser Thr Ser Glu Pro Asp Tyr Phe Tyr Gln Trp Thr Arg
                85                  90                  95

Asp Thr Ala Ile Thr Phe Leu Ser Leu Ile Ala Glu Val Glu Asp His
            100                 105                 110

Ser Phe Ser Asn Thr Thr Leu Ala Lys Val Val Glu Tyr Tyr Ile Ser
        115                 120                 125

Asn Thr Tyr Thr Leu Gln Arg Val Ser Asn Pro Ser Gly Asn Phe Asp
    130                 135                 140

Ser Pro Asn His Asp Gly Leu Gly Glu Pro Lys Phe Asn Val Asp Asp
145                 150                 155                 160

Thr Ala Tyr Thr Ala Ser Trp Gly Arg Pro Gln Asn Asp Gly Pro Ala
                165                 170                 175

Leu Arg Ala Tyr Ala Ile Ser Arg Tyr Leu Asn Ala Val Ala Lys His
            180                 185                 190

Asn Asn Gly Lys Leu Leu Leu Ala Gly Gln Asn Gly Ile Pro Tyr Ser
        195                 200                 205

Ser Ala Ser Asp Ile Tyr Trp Lys Ile Ile Lys Pro Asp Leu Gln His
    210                 215                 220

Val Ser Thr His Trp Ser Thr Ser Gly Phe Asp Leu Trp Glu Glu Asn
225                 230                 235                 240

Gln Gly Thr His Phe Phe Thr Ala Leu Val Gln Leu Lys Ala Leu Ser
                245                 250                 255

Tyr Gly Ile Pro Leu Ser Lys Thr Tyr Asn Asp Pro Gly Phe Thr Ser
            260                 265                 270

Trp Leu Glu Lys Gln Lys Asp Ala Leu Asn Ser Tyr Ile Asn Ser Ser
        275                 280                 285

Gly Phe Val Asn Ser Lys Lys His Ile Val Glu Ser Pro Gln Leu
            290                 295                 300

Ser Ser Arg Gly Gly Leu Asp Ser Ala Thr Tyr Ile Ala Ala Leu Ile
305                 310                 315                 320

Thr His Asp Ile Gly Asp Asp Thr Tyr Thr Pro Phe Asn Val Asp
            325                 330                 335

Asn Ser Tyr Val Leu Asn Ser Leu Tyr Leu Leu Val Asp Asn Lys
            340                 345                 350

Asn Arg Tyr Lys Ile Asn Gly Asn Tyr Lys Ala Gly Ala Val Gly
            355                 360                 365

Arg Tyr Pro Glu Asp Val Tyr Asn Gly Val Gly Thr Ser Glu Gly Asn
            370                 375                 380

Pro Trp Gln Leu Ala Thr Ala Tyr Ala Gly Gln Thr Phe Tyr Thr Leu
385                 390                 395                 400

Ala Tyr Asn Ser Leu Lys Asn Lys Asn Leu Val Ile Glu Lys Leu
            405                 410                 415

Asn Tyr Asp Leu Tyr Asn Ser Phe Ile Ala Asp Leu Ser Lys Ile Asp
            420                 425                 430

Ser Ser Tyr Ala Ser Lys Asp Ser Leu Thr Leu Thr Tyr Gly Ser Asp
            435                 440                 445

Asn Tyr Lys Asn Val Ile Lys Ser Leu Leu Gln Phe Gly Asp Ser Phe
            450                 455                 460

Leu Lys Val Leu Leu Asp His Ile Asp Asp Asn Gly Gln Leu Thr Glu
465                 470                 475                 480

Glu Ile Asn Arg Tyr Thr Gly Phe Gln Ala Gly Ala Val Ser Leu Thr
            485                 490                 495

Trp Ser Ser Gly Ser Leu Leu Ser Ala Asn Arg Ala Arg Asn Lys Leu
            500                 505                 510

Ile Glu Leu Leu
        515

<210> SEQ ID NO 15
<211> LENGTH: 514
<212> TYPE: PRT
<213> ORGANISM: Artificial Sequence
<220> FEATURE:
<223> OTHER INFORMATION: PHO5 - Sf GA protein

<400> SEQUENCE: 15

Met Phe Lys Ser Val Val Tyr Ser Ile Leu Ala Ala Ser Leu Ala Asn
1               5                   10                  15

Ala Val Pro Val Glu Leu Asp Lys Arg Asn Thr Gly His Phe Gln Ala
            20                  25                  30

Tyr Ser Gly Tyr Thr Val Ala Arg Ser Asn Phe Thr Gln Trp Ile His
        35                  40                  45

Glu Gln Pro Ala Val Ser Trp Tyr Tyr Leu Leu Gln Asn Ile Asp Tyr
    50                  55                  60

Pro Glu Gly Gln Phe Lys Ser Ala Lys Pro Gly Val Val Ala Ser
65                  70                  75                  80

Pro Ser Thr Ser Glu Pro Asp Tyr Phe Tyr Gln Trp Thr Arg Asp Thr
            85                  90                  95

Ala Ile Thr Phe Leu Ser Leu Ile Ala Glu Val Glu Asp His Ser Phe
            100                 105                 110

Ser Asn Thr Thr Leu Ala Lys Val Val Glu Tyr Tyr Ile Ser Asn Thr
        115                 120                 125

Tyr Thr Leu Gln Arg Val Ser Asn Pro Ser Gly Asn Phe Asp Ser Pro
130                 135                 140

Asn His Asp Gly Leu Gly Glu Pro Lys Phe Asn Val Asp Asp Thr Ala
145                 150                 155                 160

Tyr Thr Ala Ser Trp Gly Arg Pro Gln Asn Asp Gly Pro Ala Leu Arg
            165                 170                 175

Ala Tyr Ala Ile Ser Arg Tyr Leu Asn Ala Val Ala Lys His Asn Asn
            180                 185                 190

Gly Lys Leu Leu Leu Ala Gly Gln Asn Gly Ile Pro Tyr Ser Ser Ala
        195                 200                 205

Ser Asp Ile Tyr Trp Lys Ile Ile Lys Pro Asp Leu Gln His Val Ser
210                 215                 220

Thr His Trp Ser Thr Ser Gly Phe Asp Leu Trp Glu Glu Asn Gln Gly
225                 230                 235                 240

Thr His Phe Phe Thr Ala Leu Val Gln Leu Lys Ala Leu Ser Tyr Gly
                245                 250                 255

Ile Pro Leu Ser Lys Thr Tyr Asn Asp Pro Gly Phe Thr Ser Trp Leu
            260                 265                 270

Glu Lys Gln Lys Asp Ala Leu Asn Ser Tyr Ile Asn Ser Ser Gly Phe
        275                 280                 285

Val Asn Ser Gly Lys Lys His Ile Val Glu Ser Pro Gln Leu Ser Ser
290                 295                 300

Arg Gly Gly Leu Asp Ser Ala Thr Tyr Ile Ala Ala Leu Ile Thr His
305                 310                 315                 320

Asp Ile Gly Asp Asp Thr Tyr Thr Pro Phe Asn Val Asp Asn Ser
                325                 330                 335

Tyr Val Leu Asn Ser Leu Tyr Tyr Leu Leu Val Asp Asn Lys Asn Arg
            340                 345                 350

Tyr Lys Ile Asn Gly Asn Tyr Lys Ala Gly Ala Ala Val Gly Arg Tyr
            355                 360                 365

Pro Glu Asp Val Tyr Asn Gly Val Gly Thr Ser Glu Gly Asn Pro Trp
            370                 375                 380

Gln Leu Ala Thr Ala Tyr Ala Gly Gln Thr Phe Tyr Thr Leu Ala Tyr
385                 390                 395                 400

Asn Ser Leu Lys Asn Lys Lys Asn Leu Val Ile Glu Lys Leu Asn Tyr
                405                 410                 415

Asp Leu Tyr Asn Ser Phe Ile Ala Asp Leu Ser Lys Ile Asp Ser Ser
            420                 425                 430

Tyr Ala Ser Lys Asp Ser Leu Thr Leu Thr Tyr Gly Ser Asp Asn Tyr
            435                 440                 445

Lys Asn Val Ile Lys Ser Leu Leu Gln Phe Gly Asp Ser Phe Leu Lys
450                 455                 460

Val Leu Leu Asp His Ile Asp Asp Asn Gly Gln Leu Thr Glu Glu Ile
465                 470                 475                 480

Asn Arg Tyr Thr Gly Phe Gln Ala Gly Ala Val Ser Leu Thr Trp Ser
                485                 490                 495

Ser Gly Ser Leu Leu Ser Ala Asn Arg Ala Arg Asn Lys Leu Ile Glu
            500                 505                 510

Leu Leu

<210> SEQ ID NO 16
<211> LENGTH: 4632
<212> TYPE: DNA

<213> ORGANISM: Artificial Sequence
<220> FEATURE:
<223> OTHER INFORMATION: pTAN29

<400> SEQUENCE: 16

```
cagagcctct tatattcact ctgttcctcc atcgcctatt gagaaacgtt ggaataaaac     60
tctaaaaata tcatctagtt ggttagtttt tattttacca gtacattgtc acttgcggag    120
ggaggatgac ataaagattg agacgcagtc atttaatgaa gtttaaacgc aggtatttga    180
taaagtaata cgatattgaa tcatgacgta taaagtgaaa tgaacaaatg attacgtaaa    240
aaatgtcgat tttctcttga gagactccca tagcctctaa gaggccttct actacgttcc    300
atatatctaa gaatggggcc atatccagtg gaatcccagc aattatttaa ggatcaccta    360
tttctcagcc gatattttag caaaatcact accaatatca gggggcaata gttgatcgcc    420
tactttaaca aaaaatgttg ctcacgtatt aacacaggca acaaaaagga tattacgcaa    480
gaacgtagta tccacatgcc atcctccttg ttgcatcttt ttttttccga atgattccc     540
tttcctgcac aacacgagat ctttcacgca tacatcggaa ggatcacccc ccactcaagt    600
cgttgcattg ctaacatgtg gcattctgcc catttttttc acgaaaattc tctctctata    660
atgaagaccc ttgtgccctg gactctgtaa tacttgaaac tacttcctca ataatcgctt    720
ggagacctac ccccacgctt ttcaaacaag gcgctagcaa aaagcctgcc gatatctcct    780
tgccccctcc ttctgttcga gagaactacg acccgaccaa taataatgtc atacaagaac    840
cgccaagaac caactgctga accttagatc tccaatactt cagttggagt atgtgaatat    900
ataagtacct ggtcgactaa tcttcttgca tcttttcgta ttcttacatc ctatgtcgct    960
aatacagttc ccgcatagag aagaaagcaa acaaagtag tcactcgaga tctcccgagt    1020
ttatcattat caatactgcc atttcaaaga atacgtaaat aattaatagt agtgattttc    1080
ctaactttat ttagtcaaaa aattggcctt ttaattctgc tgtaacccgt acatgcccaa    1140
aataggggc gggttacaca gaatatataa catcataggt gtctgggtga acagtttatt    1200
cctggcatcc actaaatata atggagcccg cttttttta gctggcatcc agaaaaaaaa    1260
agaatcccag caccaaaata ttgttttctt caccaaccat cagttcatag gtccattctc    1320
ttagcgcaac tacacagaac aggggcacaa acaggcaaaa acgggcaca acctcaatgg    1380
agtgatgcaa cctgcttgga gtaaatgatg acacaaggca attgacctac gcatgtatct    1440
atctcatttt cttacaccct ctattacctt ctgctctctc tgatttggaa aaagctgaaa    1500
aaaaaggttg aaaccagttc cctgaaatta ttccccctatt tgactaataa gtatataaag    1560
acggtaggta ttgattgtaa ttctgtaaat ctatttctta aacttcttaa attctacttt    1620
tatagttagt ctttttttta gtttaaaaca ccaagaactt agtttcgaat aaacacacat    1680
aaacaaacaa atctagaatg attagattaa ccgtattcct cactgcagtt tttgcagcag    1740
tcgcttcctg tgttccagtt gaattggata agagaaatac aggccatttc caagcatatt    1800
ctggttacac cgtagctaga tcaaacttta ctcaatggat tcacgagcaa ccagccgtat    1860
catggtacta tttgcttcag aatatagact atccagaagg acaattcaag tctgccaagc    1920
caggggtcgt tgtggcttcc ccttctacat ccgaacctga ttacttctac caatggacta    1980
gagatactgc tatcaccttc ttgtcactta tcgcggaagt tgaggatcat tcttttttcaa    2040
atactacact agccaaggtg gttgaatact acatctctaa tacttacaca ttacaaagag    2100
tttccaaccc atctggtaac ttcgacagtc caaatcacga cggtttggga gaaccaaagt    2160
ttaatgttga tgatacagct tatactgcat cttggggtag accacaaaat gatggcccag    2220
```

```
cgttgagagc atacgcaatt tcaagatacc ttaacgcagt agcaaaacac aacaacggta   2280
agttactgct cgctggacaa aacggtattc cttactcttc agcttctgat atctactgga   2340
agattatcaa gccagatctt caacatgtgt caacccattg gtctacatct ggttttgatt   2400
tgtgggaaga gaatcaggga acacatttct ttactgcgtt ggtccagcta aaagcactta   2460
gttacggcat tcctttaagt aagacctaca acgatcctgg tttcactagt tggctagaaa   2520
agcaaaagga tgctttaaac tcttatatca acagctctgg tttcgtaaac tctggcaaaa   2580
agcatatagt ggagagccct caactatctt caagaggagg gttggatagc gccacataca   2640
ttgcagcctt aatcacacat gatattggcg acgacgacac ttacacacct tcaacgttg   2700
acaactccta tgtcttgaac tcactgtatt accttctagt cgataacaaa aaccgttaca   2760
aaatcaatgg taactacaag gccggtgctg ctgttggtag atacccagag gatgtttaca   2820
acggtgttgg gacatcagaa ggcaatccat ggcaattagc tacagcctac gccggccaaa   2880
cattttacac actggcttac aactcattga aaaacaaaaa aaacttagtg attgaaaagt   2940
tgaactacga cctctacaat tctttcatag cagatttatc caagatcgat agttcttacg   3000
catcaaaaga ctccttgact ttgacctacg gttctgacaa ctacaaaaac gtcataaagt   3060
cactattaca gtttggagat tcattcctga aggtcttgct cgatcacatt gatgataatg   3120
gacaattaac agaagagatc aatagataca cagggttcca ggctggtgct gttagtttga   3180
catggtcctc tggttcatta ctttcagcaa accgtgcgag aaataagttg attgaactat   3240
tgtagttaat taaacaggcc ccttttcctt tgtcgatatc atgtaattag ttatgtcacg   3300
cttacattca cgccctcctc ccacatccgc tctaaccgaa aaggaaggag ttagacaacc   3360
tgaagtctag gtccctattt atttttttat agttatgtta gtattaagaa cgttatttat   3420
atttcaaatt ttctttttt ttctgtacaa acgcgtgtac gcatgtaacg ggcagacggc   3480
cggccataac ttcgtataat gtatgctata cgaagttatg gcaacggttc atcatctcat   3540
ggatctgcac atgaacaaac accagagtca aacgacgttg aaattgaggc tactgcgcca   3600
attgatgaca atacagacga tgataacaaa ccgaagttat ctgatgtaga aaaggattag   3660
agatgctaag agatagtgat gatatttcat aaataatgta attctatata tgttaattac   3720
cttttttgcg aggcatattt atggtgaagg ataagttttg accatcaaag aaggttaatg   3780
tggctgtggt ttcagggtcc ataaagcttt tcaattcatc tttttttttt ttgttctttt   3840
ttttgattcc ggtttctttg aaattttttt gattcggtaa tctccgagca gaaggaagaa   3900
cgaaggaagg agcacagact tagattggta tatatacgca tatgtggtgt tgaagaaaca   3960
tgaaattgcc cagtattctt aacccaactg cacagaacaa aaacctgcag gaaacgaaga   4020
taaatcatgt cgaaagctac atataaggaa cgtgctgcta ctcatcctag tcctgttgct   4080
gccaagctat ttaatatcat gcacgaaaag caaacaaact tgtgtgcttc attggatgtt   4140
cgtaccacca aggaattact ggagttagtt gaagcattag gtcccaaaat tgtttacta   4200
aaaacacatg tggatatctt gactgatttt tccatggagg gcacagttaa gccgctaaag   4260
gcattatccg ccaagtacaa ttttttactc ttcgaagaca gaaaatttgc tgacattggt   4320
aatacagtca aattgcagta ctctgcgggt gtatacagaa tagcagaatg ggcagacatt   4380
acgaatgcac acggtgtggt gggcccaggt attgttagcg gtttgaagca ggcggcggaa   4440
gaagtaacaa aggaacctag aggccttttg atgttagcag aattgtcatg caagggctcc   4500
ctagctactg gagaatatac taagggtact gttgacattg cgaagagcga caagattttt   4560
```

-continued

```
gttatcggct ttattgctca aagagacatg ggtggaagag atgaaggtta cgattggttg    4620
attatgacac gc                                                        4632

<210> SEQ ID NO 17
<211> LENGTH: 4363
<212> TYPE: DNA
<213> ORGANISM: Artificial Sequence
<220> FEATURE:
<223> OTHER INFORMATION: pTAN30

<400> SEQUENCE: 17
ggccgctcca tggagggcac agttaagccg ctaaaggcat tatccgccaa gtacaatttt      60
ttactcttcg aagacagaaa atttgctgac attggtaata cagtcaaatt gcagtactct    120
gcgggtgtat acagaatagc agaatgggca gacattacga atgcacacgg tgtggtgggc    180
ccaggtattg ttagcggttt gaagcaggcg gcggaagaag taacaaagga acctagaggc    240
cttttgatgt tagcagaatt gtcatgcaag ggctccctag ctactggaga atatactaag    300
ggtactgttg acattgcgaa gagcgacaaa gattttgtta tcggctttat tgctcaaaga    360
gacatgggtg aagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaggaacc atccaatacc    780 tcgccagaac caagtaacag tattttacgg ggcacaaatc aagaacaata agacaggact    840
gtaaagatgg acgcattgaa ctccaaagaa caacaagagt tccaaaaagt agtggaacaa    900
aagcaaatga aggatttcat gcgtttgata acttcgtata atgtatgcta tacgaagtta    960
tctcgagggc cagaaaaagg aagtgtttcc ctccttcttg aattgatgtt accctcataa   1020
agcacgtggc tcttatcga gaagaaatt ccgtcgctc gtgatttgtt tgcaaaaaga   1080
acaaaactga aaaacccag acacgctcga cttcctgtct tcctgttgat gcagcttcc    1140 aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
cgtgtgacaa caacagcctg ttctcacaca ctctttctct ctaaccaagg gggtggttta   1380
gtttagtaga acctcgtgaa acttacattt acatatatat aaacttgcat aaattggtca   1440
atgcaagaaa tacatatttg gtcttttcta attcgtagtt tttcaagttc ttagatgctt   1500 tcttttctc ttttttacag atcatcaagg aagtaattat ctactttta caagtctaga   1560 atgatcagac ttcagttttt cctaacagcc gttttcgccg ccgttgcatc atgtgtccca   1620
gtagaattgg ataagagaaa caccggccat ttccaagcat attcaggata caccgttgca   1680
cgttctaatt tcacacaatg gattcatgag cagcctgctg tgtcctggta ctacttatta   1740
caaaacattg attatcctga gggacaattc aagtcagcga accaggcgt tgtggttgct   1800 tctccatcca cttcagaacc agactacttc taccagtgga cccgtgacac agcaataact   1860
ttcttatctt tgatagcaga agtagaagat cactcatttt caaatacaac tctagctaag   1920
gttgtcgaat actacatctc taacacatac accctacaaa gagtttctaa cccatctggt   1980
```

```
aatttcgata gcccaaatca cgatggtctg ggtgaaccaa agttcaacgt tgacgacact    2040
gcttacactg catcatgggg cagacctcaa acgacggtc cagccttaag agcttacgcg     2100
atctcaagat atttgaacgc agttgccaag cataacaacg gtaagctatt gctcgcgggt    2160
caaaatggta ttccttactc atctgcatca gatatctact ggaagattat caagccagat    2220
ttacaacatg taagtactca ctggagtaca tctggttttg acttatggga agagaatcaa    2280
ggtacacatt tctttactgc acttgtccag ttaaaagctc tttcatacgg tatacctttg    2340
tctaagacat ataacgatcc aggatttact tcttggttgg aaaagcagaa ggatgccttg    2400
aactcttaca tcaattccag cggcttcgtc aactccggga aaaagcacat tgtcgaatct    2460
cctcaattat ctagtagagg gggtcttgat agcgctactt acatcgctgc tctaattaca    2520
catgatattg gtgatgatga tacatacact cctttttaacg tagataattc ttatgtgctg    2580
aactctttat actatctgct tgtagacaac aaaaacagat acaagatcaa cgggaactac    2640
aaagcaggag ctgcagttgg tagatacccca gaagatgtgt acaatggagt gggaacctca    2700
gagggaaacc catggcaatt ggcgacagca tacgccggcc aaaccttta cacactggct     2760 tacaattctc tcaaaaacaa aaaaaatttg gttattgaga agttgaatta cgatctatac    2820
aactccttta tagctgactt aagtaagatt gactcctctt acgcttctaa ggattcattg    2880
acattgacct acggctcaga taactacaaa aatgtcatta agtcacttt acaattcggg     2940 gattcttct tgaaagtctt gttggaccat attgatgata atggtcagct aacagaggaa     3000
atcaacagat atacaggttt tcaagctggc gcagtttccc tcacttggag tagtggttca    3060
ctcttatctg caaacagagc cagaaacaag ttgatcgaat tgctttagtt aattaagaag    3120
ttttgttaga aaataaatca tttttttaatt gagcattctt attcctattt tatttaaata   3180
gttttatgta ttgttagcta catacaacag tttaaatcaa attttctttt tcccaagtcc    3240
aaaatggagg tttattttga tgacccgcat gcgattatgt tttgaaagta taagactaca    3300
tacatgtaca tatatttaaa catgtaaacc cgtccattat attgccgggc agacggccgg    3360
ccttatagcc tagctttaag gctactttaa aaacttttta tttattcata cacatatatt    3420
atcgaacatt cgtataactt aatatcattc aaaaaaaaa aaaaaaaaa aagaaaacat      3480 atacacatat atatttatgt ttatagagag agagagagaa aatttgaatt tttgaatcat    3540
ttgcaaagtt atatgttta tacattattt attcattttt tttggtgtcg aggacattgt     3600
gctgttcaga gaaccactta aaatacgcat cgttctgtaa atatccactt tcattaaaaa    3660
ccttattcac ttctaacttt gccttcaact ccttcttgga gttttctccc ttttttttct    3720
gaacaagctc aaccagatat aatggttcgt tcttttcgaa ctttgtcttt acatatattt    3780
cctcctttgt acctcttctc tttcccacat aaacagtccc cttttcaata aaacgagaga    3840
aataccagaa agtagcgag agaacaaaat atgcgcctac caaaagcttt tgatacgtaa     3900
caatctgatc tctctcaaat ttttatcca agaagaaact caaaccagct acaacagcta     3960
tggaataacc tatgtacaat ttagcatcga gtaaagcgta tgatctctcg taatttaatc    4020
tcgcgaaaac agaaggtagg gcttcatcta aagcttggtt caactccggg attgaatata    4080
cattaatagg tttagcagaa ctcatcttga acaggcgtct cttttcctta caataacttg    4140
tgcttttcct tctataattc cgtttcaacg tgtacaattg tcattttttg tctggtatga    4200
ttttgcagaa ctgaaaaaat ctcttaaatg ttccgcctca tcaagaaggc atattccttt    4260
acaaaagtac attgatctta caagaagcta gctaatggta ctatttaaaa aacaactaca    4320
```

```
ctccatcaat acataaaatt gttatgatag acttgaggga cgg            4363
```

<210> SEQ ID NO 18
<211> LENGTH: 5015
<212> TYPE: DNA
<213> ORGANISM: Artificial Sequence
<220> FEATURE:
<223> OTHER INFORMATION: pTAN37

<400> SEQUENCE: 18

```
cagagcctct tatattcact ctgttcctcc atcgcctatt gagaaacgtt ggaataaaac     60
tctaaaaata tcatctagtt ggttagtttt tattttacca gtacattgtc acttgcggag    120
ggaggatgac ataaagattg agacgcagtc atttaatgaa gtttaaacgc aggtatttga    180
taaagtaata cgatattgaa tcatgacgta taaagtgaaa tgaacaaatg attacgtaaa    240
aaatgtcgat tttctcttga gagactccca tagcctctaa gaggccttct actacgttcc    300
atatatctaa gaatggggcc atatccagtg gaatcccagc aattatttaa ggatcaccta    360
tttctcagcc gatattttag caaaatcact accaatatca gggggcaata gttgatcgcc    420
tactttaaca aaaatgttg ctcacgtatt aacacaggca acaaaaagga tattacgcaa    480
gaacgtagta tccacatgcc atcctccttg ttgcatcttt tttttccga aatgattccc    540
tttcctgcac aacacgagat ctttcacgca tacatcggaa ggatcacccc ccactcaagt    600
cgttgcattg ctaacatgtg gcattctgcc cattttttc acgaaaattc tctctctata    660
atgaagaccc ttgtgccctg gactctgtaa tacttgaaac tacttcctca ataatcgctt    720
ggagacctac ccccacgctt ttcaaacaag gcgctagcaa aaagcctgcc gatatctcct    780
tgccccctcc ttctgttcga gagaactacg acccgaccaa taataatgtc atacaagaac    840
cgccaagaac caactgctga acctagatc tccaatactt cagttggagt atgtgaatat    900
ataagtacct ggtcgactaa tcttcttgca tcttttcgta ttcttacatc ctatgtcgct    960
aatacagttc ccgcatagag aagaaagcaa acaaaagtag tcactcgaga tctcccgagt   1020
ttatcattat caatactgcc atttcaaaga atacgtaaat aattaatagt agtgattttc   1080
ctaactttat ttagtcaaaa aattggcctt taattctgc tgtaacccgt acatgcccaa   1140
aatagggggc gggttacaca gaatatataa catcataggt gtctgggtga acagtttatt   1200
cctggcatcc actaaatata atggagcccg ctttttttaa gctggcatcc agaaaaaaaa   1260
agaatcccag caccaaaata ttgttttctt caccaaccat cagttcatag gtccattctc   1320
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttcccctatt tgactaataa gtatataaag   1560
acggtaggta ttgattgtaa ttctgtaaat ctatttctta aacttcttaa attctacttt   1620
tatagttagt cttttttta gtttaaaaca ccaagaactt agtttcgaat aaacacacat   1680
aaacaaacaa atctagaatg atcagactta ctgttttcct cacagccgtt tttgcagcag   1740
tagcttcttg tgttccagtt gaattggata agagaaatac aggtcatttc caagcttact   1800
ctggttacac tgtggctaga tctaacttca cacaatggat tcatgaacag cctgccgtga   1860
gttggtacta tttgctacaa aacattgatt accctgaggg tcaattcaaa tcagctaagc   1920
caggtgttgt tgtcgcgagc ccatcaactt ctgaaccaga ttacttctac caatggacta   1980
gagataccgc aataaccttc ttatctctaa tcgcagaggt agaagatcac tctttttcaa   2040
```

```
atactaccct ggcaaaagtg gtcgagtact acatctcaaa cacatacacc ttgcagagag   2100
tctcaaaccc atcaggaaac ttcgattctc ctaatcatga cggcttagga gaaccaaagt   2160
ttaatgttga cgataccgct tatactgcat cttggggtag accacagaat gatggccctg   2220
ccttacgtgc atacgccatt tccagatatc tcaacgctgt agcgaagcac aacaacggta   2280
agctgctttt agctggtcaa aatgggatac catactcttc cgcttcagac atttactgga   2340
agattatcaa accagacttg cagcatgtca gtacacattg gtcaacttct ggttttgatt   2400
tgtgggaaga gaaccaaggc actcacttct ttacagcctt ggttcaacta aaggcattgt   2460
cttacggaat cccttttgtcc aagacataca atgatcctgg attcactagt tggctagaaa   2520
agcaaaagga tgcactgaac tcatacatta acagttcagg ctttgtgaac tccggtaaaa   2580
agcatattgt tgaaagccca caactatcta gcagaggtgg tttagattct gcaacctaca   2640
tagcagcctt gatcacacac gacattgggg atgacgatac atacacacca ttcaacgtcg   2700
acaattcata cgttttgaat agcttatact acctactggt agataacaaa aacagatata   2760
agatcaatgg caactacaag gccggtgctg ccgtaggaag atacccctgaa gatgtctaca   2820 acggagttgg tacatcagaa ggtaacccat ggcaattagc aacagcatat gcgggccaga   2880
cattttacac tttggcttac aattcattga aaaacaaaaa aaatttagtg atagaaaagc   2940
ttaactatga cctttacaac tctttcattg ccgatttatc caagattgat tcctcctacg   3000
catcaaagga ctccttgaca cttacatacg gttctgacaa ctacaaaaat gttatcaagt   3060
ctctcttgca atttggtgat tctttcttga aggtttact cgatcatatc gatgataatg   3120
gtcaactaac tgaggaaatc aacagataca ctgggttcca agctggagct gtctctttaa   3180
catggagttc agggagtttg ttatctgcta acagagcgcg taacaaactt attgagcttc   3240
tgtagttaat taaacaggcc ccttttcctt tgtcgatatc atgtaattag ttatgtcacg   3300
cttacattca cgccctcctc ccacatccgc tctaaccgaa aaggaaggag ttagacaacc   3360
tgaagtctag gtccctattt atttttttat agttatgtta gtattaagaa cgttatttat   3420
atttcaaatt tttctttttt ttctgtacaa acgcgtgtac gcatgtaacg ggcagacggc   3480
cggccataac ttcgtataat gtatgctata cgaagttatc cttacatcac acccaatccc   3540
ccacaagtga tcccccacac accatagctt caaaatgttt ctactccttt tttactcttc   3600
cagattttct cggactccgc gcatcgccgt accacttcaa acacccaag cacagcatac   3660 taaatttccc ctctttcttc ctctagggtg gcgttaatta cccgtactaa aggtttggaa   3720
aagaaaaaag agaccgcctc gtttcttttt cttcgtcgaa aaaggcaata aaaattttta   3780
tcacgtttct ttttcttgaa aaattttttt tttgattttt ttctctttcg atgacctccc   3840
attgatattt aagttaataa atggtcttca atttctcaag tttcagtttc gttttttcttg   3900 ttctattaca acttttttta cttcttgctc attagaaaga aagcatagca atctaatcta   3960
agttttaatt acaaaatgcc acaatcctgg gaagaattgg ccgccgacaa acgtgcccgt   4020
ttggctaaaa ccattcctga cgaatggaag gttcaaactt gcctgccgga agattccgtt   4080
attgatttcc caagaagtc cggtattttg tctgaggctg aattgaagat taccgaagcc   4140
tctgctgctg atttggtctc caagttggcc gctggtgagt tgacttctgt tgaagtcact   4200
ttggcttttt gtaagagagc tgctattgct caacaattaa ccaactgtgc tcacgaattc   4260
ttcccagatg ctgctttagc tcaagctaga gaattagatg aatactacgc taagcataag   4320
agaccagttg gtccattaca cggtttacca atctctttaa aggaccaatt gcgtgttaag   4380
```

| | |
|---|---|
| ggttacgaaa cctccatggg ttacatttcc tggttaaaca aatacgatga aggtgattcc | 4440 |
| gtcttaacca ccatgttgag aaaagctggt gctgttttct acgttaagac ctctgtccca | 4500 |
| caaaccttga tggtctgtga accgtcaac aacatcattg gtagaactgt caatccaaga | 4560 |
| aacaaaaatt ggtcctgtgg tggttcttct ggtggtgaag gtgctattgt tggtattaga | 4620 |
| ggtggtgtta ttggtgtcgg tactgacatt ggtggttcca ttagagtccc agctgctttc | 4680 |
| aacttttat acggtttgag accatctcac ggtagattgc catatgctaa aatggctaac | 4740 |
| tctatggaag gtcaagaaac cgttcactcc gtcgttggtc ctatcactca ctccgtcgaa | 4800 |
| gacttgagat tgttcaccaa atctgtcttg ggtcaagaac cttggaagta cgactctaag | 4860 |
| gtcatcccca tgccatggag acaatctgaa tctgacatca ttgcctctaa gattaagaat | 4920 |
| ggtggtttga acattggtta ttacaatttc gacggtaacg tcttgccaca cccaccaatt | 4980 |
| ttacgtggtg tcgaaactac cgttgccgct ttggc | 5015 |

<210> SEQ ID NO 19
<211> LENGTH: 4771
<212> TYPE: DNA
<213> ORGANISM: Artificial Sequence
<220> FEATURE:
<223> OTHER INFORMATION: pTAN39

<400> SEQUENCE: 19

| | |
|---|---|
| ggccgcgaag gtgctattgt tggtattaga ggtggtgtta ttggtgtcgg tactgacatt | 60 |
| ggtggttcca ttagagtccc agctgctttc aacttttat acggtttgag accatctcac | 120 |
| ggtagattgc catatgctaa aatggctaac tctatggaag gtcaagaaac cgttcactcc | 180 |
| gtcgttggtc ctatcactca ctccgtcgaa gacttgagat tgttcaccaa atctgtcttg | 240 |
| ggtcaagaac cttggaagta cgactctaag gtcatcccaa tgccatggag acaatctgaa | 300 |
| tctgacatca ttgcctctaa gattaagaat ggtggtttga acattggtta ttacaatttc | 360 |
| gacggtaacg tcttgccaca cccaccaatt ttacgtggtg tcgaaactac cgttgccgct | 420 |
| ttggccaagg ctggtcacac cgttactcca tggactccat acaagcatga tttcggtcat | 480 |
| gacttgattt cccacatcta tgctgctgat ggttctgccg acgtcatgag agacatttct | 540 |
| gcctctggtg agccagccat ccctaacatt aaggacttgt tgaacccaaa tattaaggct | 600 |
| gttaacatga acgaattgtg ggacactcat ttacaaaagt ggaactatca aatgaaatac | 660 |
| ttggaaaagt ggcgtgaagc tgaagaaaaa gctggtaagg aattggacgc tattatcgct | 720 |
| ccaattactc ctaccgccgc tgtcagacac gatcaattca gatactacgg ttacgcctcc | 780 |
| gttattaact tattggattt cacctctgtt gtcgtcccag tcactttcgc tgataagaat | 840 |
| attgataaga gaacgaatc ttttaaagct gtttccgaat tggatgcttt ggttcaagaa | 900 |
| gaatacgacc cagaggctta tcacggtgct cctgttgctg ttcaagttat tggtagaaga | 960 |
| ttgtccgaag agagaacttt ggctatcgcc gaagaagtcg gtaaattgtt gggtaacgtc | 1020 |
| gtcactccat aagcgaattt cttatgattt atgattttta ttattaaaata agttataaaa | 1080 |
| aaaataagtg tatacaaatt ttaaagtgac tcttaggttt taaaacgaaa attcttattc | 1140 |
| ttgagtaact ctttcctgta ggtcaggttg ctttctcagg tatagcatga ggtcgctctt | 1200 |
| attgaccaca cctctaccgg catgccgagc aaatgcctgc aaatcgctcc ccatttcacc | 1260 |
| caattgtaga tatgctaact ccagcaatga gttgatgaat ctcggtgtgt atttttatgtc | 1320 |
| ctcagaggac aacacataac ttcgtataat gtatgctata cgaagttatc tcgagggcca | 1380 |
| gaaaaaggaa gtgttttccct ccttcttgaa ttgatgttac cctcataaag cacgtggcct | 1440 |

```
cttatcgaga aagaaattac cgtcgctcgt gatttgtttg caaaaagaac aaaactgaaa    1500
aaacccagac acgctcgact tcctgtcttc ctgttgattg cagcttccaa tttcgtcaca    1560
caacaaggtc ctagcgacgg ctcacaggtt ttgtaacaag caatcgaagg ttctggaatg    1620
gcgggaaagg gtttagtacc acatgctatg atgcccactg tgatctccag agcaaagttc    1680
gttcgatcgt actgttactc tctctctttc aaacagaatt gtccgaatcg tgtgacaaca    1740
acagcctgtt ctcacacact cttttcttct aaccaagggg gtggtttagt ttagtagaac    1800
ctcgtgaaac ttacatttac atatatataa acttgcataa attggtcaat gcaagaaata    1860
catatttggt cttttctaat tcgtagtttt tcaagttctt agatgctttc ttttctctt     1920 ttttacagat catcaaggaa gtaattatct acttttttaca agtctagaat gattagatta   1980
acagtatttc ttacagccgt tttcgcagcc gtcgcatcct gtgttccagt agaattagat    2040
aagcgtaata caggacattt tcaagcttac tctggctata cagttgcgag atctaacttt    2100
acacaatgga ttcacgaaca gccagcagtt tcttggtact atttgctcca aaacatcgac    2160
taccctgaag gccaattcaa gtctgcaaag ccaggagtgg tcgtcgcttc tcctagtact    2220
tcagaaccag attacttcta ccagtggaca agagacactg ctattacctt cctgagctta    2280
atcgctgaag ttgaagatca ctctttttct aatacaacac tggccaaagt agttgagtac    2340
tacatctcta acacttacac tctacaaaga gtgtcaaacc cttctgggaa cttcgacagc    2400
ccaaaccatg atggtttggg ggagccaaaa ttcaacgttg atgatacagc ctacaccgca    2460
tcttggggta gaccacaaaa cgacggacca gctttaagag catacgcaat atctcgttac    2520
cttaatgctg ttgcaaagca caataatgga aagttgttgt tggctggtca aaacggtatt    2580
ccttactctt cagcatctga tatctactgg aagattatca agccagatct tcaaacgtat   2640
tccacacatt ggtcaacctc cggcttcgat ttatgggagg aaaatcaggg tacacatttc   2700
ttcaccgctc tagtgcaatt gaaggctttg agttacggca ttccattgtc taagacttac   2760
aacgatcctg gtttcacctc atggcttgaa aagcagaagg atgccctgaa tagctacatc   2820
aactcatctg gttttgttaa ctcagggaaa agcatatag ttgaatcccc acaactatca    2880
tcaagaggag gtttagactc cgccacatac attgctgcct tgattacaca tgatattggg   2940
gatgatgaca catatactcc atttaacgtc gataacagtt atgtccttaa ttccttatac   3000
tatttgttgg tcgataacaa aaatagatac aaaatcaacg gcaactacaa ggctggcgca   3060
gcggtgggta gataccctga ggatgtttac aatggtgtag gtacatctga aggcaatcca   3120
tggcaattag cgactgctta cgctggacaa actttctaca cacttgcgta caactcattg   3180
aaaaacaaaa aaacctagt cattgaaaag ttgaattacg atctgtacaa ctctttcatc     3240
gcagacctat caaagattga ctcatcttat gcaagtaaag attcactaac tttaacctac   3300
ggtagtgata actacaaaaa cgttatcaag tctttactcc agtttggtga ttcattcttg    3360
aaggtgttgt tagatcatat agacgacaat ggtcaactca cagaggagat aaacagatac    3420
actggttttc aagcaggagc tgtttcactt acttggtcaa gtggttcttt gctttccgcc    3480
aacagagcca gaaacaagct catcgaatta ctatagttaa ttaagaagtt ttgttagaaa    3540
ataaatcatt ttttaattga gcattcttat tcctatttta tttaaatagt tttatgtatt    3600
gttagctaca tacaacagtt taaatcaaat tttcttttc ccaagtccaa aatggaggtt     3660
tattttgatg acccgcatgc gattatgttt tgaaagtata agactacata catgtacata    3720
tatttaaaca tgtaaacccg tccattatat tgccgggcag acggccggcc ttatagccta    3780
```

```
gctttaaggc tactttaaaa acttttattt tattcataca catatattat cgaacattcg    3840
tataacttaa tatcattcaa aaaaaaaaaa aaaaaaaaaa gaaaacatat acacatatat    3900
atttatgttt atagagagag agagagaaaa tttgaatttt tgaatcattt gcaaagttat    3960
atgttttata cattatttat tcattttttt tggtgtcgag gacattgtgc tgttcagaga    4020
accacttaaa atacgcatcg ttctgtaaat atccactttc attaaaaacc ttattcactt    4080
ctaactttgc cttcaactcc ttcttggagt tttctccctt tttttctga acaagctcaa    4140 ccagatataa tggttcgttc ttttcgaact ttgtctttac atatatttcc tcctttgtac    4200
ctcttctctt tcccacataa acagtcccct tttcaataaa acgagagaaa taccagaaaa    4260
gtagcgagag aacaaaatat gcgcctacca aaagcttttg atacgtaaca atctgatctc    4320
tctcaaattt tttatccaag aagaaactca aaccagctac aacagctatg gaataaccta    4380
tgtacaattt agcatcgagt aaagcgtatg atctctcgta atttaatctc gcgaaaacag    4440
aaggtagggc ttcatctaaa gcttggttca actccgggat tgaatataca ttaataggtt    4500
tagcagaact catcttgaac aggcgtctct tttccttaca ataacttgtg cttttccttc    4560
tataattccg tttcaacgtg tacaattgtc attttttgtc tggtatgatt ttgcagaact    4620
gaaaaaatct cttaaatgtt ccgcctcatc aagaaggcat attcctttac aaaagtacat    4680
tgatcttaca agaagctagc taatggtact atttaaaaaa caactacact ccatcaatac    4740
ataaaattgt tatgatagac ttgagggacg g                                  4771
```